United States Patent
Stadlwieser et al.

(10) Patent No.: US 7,879,853 B2
(45) Date of Patent: Feb. 1, 2011

(54) 4,6-DISUBSTITUTED PYRIMIDINES AND THEIR USE AS PROTEIN KINASE INHIBITORS

(75) Inventors: Josef Stadlwieser, Constance (DE); Thomas Baer, Reichenau (DE); Thomas Maier, Stockach (DE); Thomas Beckers, Constance (DE); Thomas Ciossek, Ravensburg (DE); Armin Zuelch, Constance (DE); Ulrich Graedler, Heidelberg (DE)

(73) Assignee: Bayer Schering Pharma AG, Berlin (DE)

( * ) Notice: Subject to any disclaimer, the term of this patent is extended or adjusted under 35 U.S.C. 154(b) by 780 days.

(21) Appl. No.: 11/630,352

(22) PCT Filed: Jun. 28, 2005

(86) PCT No.: PCT/EP2005/053019

§ 371 (c)(1),
(2), (4) Date: Dec. 21, 2006

(87) PCT Pub. No.: WO2006/000589

PCT Pub. Date: Jan. 5, 2006

(65) Prior Publication Data

US 2007/0208034 A1     Sep. 6, 2007

(30) Foreign Application Priority Data

Jun. 28, 2004   (EP)   ................................ 04103011
Mar. 23, 2005   (EP)   ................................ 05102355

(51) Int. Cl.
C07D 405/04   (2006.01)
A61K 31/506   (2006.01)
(52) U.S. Cl. ............ 514/235.8; 514/252.2; 514/252.14; 514/256; 544/122; 544/295; 544/328; 544/329
(58) Field of Classification Search .................. 544/122, 544/295, 328, 329; 514/235.8, 252.2, 252.14, 514/256
See application file for complete search history.

(56) References Cited

U.S. PATENT DOCUMENTS

| | | | |
|---|---|---|---|
| 5,821,246 | A | 10/1998 | Brown et al. |
| 2003/0199511 | A1 | 10/2003 | Li et al. |

FOREIGN PATENT DOCUMENTS

| | | | |
|---|---|---|---|
| WO | 99/06378 | A1 | 2/1999 |
| WO | 99/24440 | A1 | 5/1999 |
| WO | 01/27089 | A1 | 4/2001 |
| WO | 01/47897 | A1 | 7/2001 |
| WO | 02/12198 | A2 | 2/2002 |
| WO | 02/094831 | A1 | 11/2002 |
| WO | 03/037869 | A1 | 5/2003 |
| WO | 03/037891 | A1 | 5/2003 |
| WO | 03/057165 | A2 | 7/2003 |
| WO | 2004/048365 | A1 | 6/2004 |
| WO | 2005/026129 | A1 | 3/2005 |
| WO | 2005/070900 | A1 | 8/2005 |

OTHER PUBLICATIONS

Simone, Oncology: Introduction, Cecil Textbook of Medicine, 20th Edition, vol. 1, pp. 1004-1010, 1996.*
Cheng et al., The Akt/PKB pathway: molecular target for cancer drug discovery, Oncogene Rev. (2005) 24, pp. 7482-7492.*
Ozes, O. N., et al., "NF-$_K$B activation by tumour necrosis factor requires the Akt serine-threonine kinase", Nature, vol. 401, pp. 82-85, (1999).
Reuveni, H., et al., "Toward a PKB Inhibitor: Modification of a Selective PKA Inhibitor by Rational Design", Biochemistry, vol. 41, pp. 10304-10314, (2002).
Stål, O., et al., "Akt kinases in breast cancer and the results of adjuvant therapy", Breast Cancer Res, vol. 5, pp. R37-R44, (2003).
Thakkar, H., et al., "Pro-survival Function of Akt/Protein Kinase B in Prostate Cancer Cells", The Journal of Biological Chemistry, vol. 276, No. 42, pp. 38361-38369, (2001).
Datta, S. R., et al., "Akt Phosphorylation of BAD Couples Survival Signals to the Cell-Intrinsic Death Machinery", Cell, vol. 91, pp. 231-241, (1997).
DeFeo-Jones, D., et al., "Tumor cell sensititzation to apoptotic stimuli by selective inhibition of specific Akt/PKB family members", Mol Cancer Ther, vol. 4, No. 2, pp. 271-273, (2005).
Datta, S. R., et al., "Cellular survival: a play in three Akts", Genes & Development, vol. 13, pp. 2905-2927, (1999).
Franke, T. F., et al., "The Protein Kinase Encoded by the Akt Proto-Oncogene Is a Target of the PDGF-Activated Phosphatidylinositol 3-Kinase", Cell, vol. 81, pp. 727-736, (1995).
Barnett, S. F., et al., "Identification and characterization of pleckstrin-homology-domain-dependent and isoenzyme-specific Akt inhibitors", Biochem J., vol. 385, pp. 399-408, (2005).
Cross, D. A. E., et al., "Inhibition of glycogen synthase kinase-3 by insulin mediated by protein kinase B", Nature, vol. 378, pp. 785-789, (1995).
Beresford, S. A., et al., "Differential Effects of Phosphatidylinositol-3/Akt-Kinase Inhibition on Apoptotic Sensitization to Cytokines in LNCaP and PC-3 Prostate Cancer Cells", Journal of Interferon and Cytokine Research, vol. 21, pp. 313-322, (2001).

(Continued)

Primary Examiner—Deepak Rao
(74) Attorney, Agent, or Firm—The Nath Law Group; Joshua B. Goldberg; Robert M. Joynes

(57) ABSTRACT

The invention relates to novel pyrimidine derivatives of Formula (1)

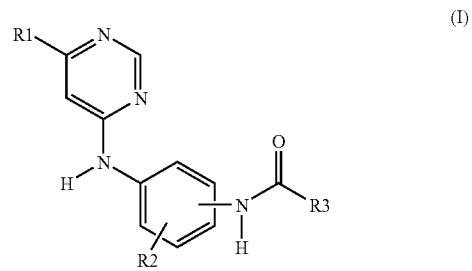

which are efficacious inhibitors of protein kinases, in particular of one or more isoforms of the protein kinase B/Akt.

8 Claims, No Drawings

OTHER PUBLICATIONS

Brunet, A., et al., "Akt Promotes Cell Survival by Phosphorylating and Inhibiting a Forkhead Transcription Factor", *Cell*, vol. 96, pp. 857-868, (1999).

Cohen, P., "Protein kinases—the major drug targets of the twenty-first century?", *Nature Reviews*, vol. 1, pp. 309-315, (2002).

Cardone, M. H., et al., "Regulation of Cell Death Protease Caspase-9 by Phosphorylation", *Science*, vol. 282, pp. 1318-1321, (1998).

Cross, T. G., et al., "Serine/Threonine Protein Kinases and Apoptosis", *Experimental Cell Research*, vol. 256, pp. 34-41.

Kulik, G., et al., "Antiapoptotic Signalling by the Insulin-Like Growth Factor I Receptor, Phosphatidylinositol 3-Kinase, and Akt", *Molecular and Cellular Biology*, vol. 17, No. 3, pp. 1595-1606, (1997).

Malik, S. N., et al., "Immunohistochemical Demonstration of Phospho-Akt in High Gleason Grade Prostate Cancer", *Clinical Cancer Research.*, vol. 8, pp. 1168-1171, (2002).

Nesterov, A., et al., "Elevated Akt Activity Protects the Prostate Cancer Cell Line LNCaP from TRAIL-induced Apoptosis", *The Journal of Biological Chemistry*, vol. 276, No. 14, pp. 10767-10774, (2001).

Testa et al., "AKT signaling in normal and malignant cells," *Oncogene* (2005) 24, pp. 7391-7393.

Mitsiades et al., Current Cancer Drug Targets, 4, 2004, 235-256.

Hill et al., Pharmacology & Therapeutics, 93, 2002, 243-251.

* cited by examiner

4,6-DISUBSTITUTED PYRIMIDINES AND THEIR USE AS PROTEIN KINASE INHIBITORS

This application was filed under 35 U.S.C. 371 as a national stage of PCT/EP2005/053019, filed Jun. 28, 2005.

FIELD OF APPLICATION OF THE INVENTION

The invention relates to novel pyrimidine derivatives as inhibitors of protein kinases, in particular of one or more isoforms of the protein kinase B (PKB)/Akt, which can be used in the pharmaceutical industry for the production of pharmaceutical compositions.

KNOWN TECHNICAL BACKGROUND

Protein kinases are key regulators in many cellular process like signal transduction, proliferation, cell cycle regulation, differentiation and survival/apoptosis as well as pathophysiological alterations within these processes causing diseases. Thus, protein kinases constitute an important target class for therapeutic intervention (P. Cohen, Nature Rev Drug Discovery 1, 309, 2002; T. G. Cross, et al., Exp. Cell Res. 256, 34-41, 2000). They can be categorized regarding their substrate specificity, namely enzymes specific for tyrosine and/or serine/threonine residues. Many protein kinases specific for tyrosine residues are membrane associated or membrane spanning enzymes, like the epidermal growth factor receptor (EGFR/HER1). In contrast, many serine/threonine specific protein kinases are intracellular kinases involved in signal transduction processes within the cell. Regarding cancer therapy, Gilvec (Imatinib®) for treating chronic myelogenous leukemia (CML) inhibiting the bcr-abl kinase fusion protein and Iressa (Gefitinib®) inhibiting the EGFR kinase for treatment of late stage non-small-cell lung cancer (NSCLC) patients have been approved recently. Cancer is a complex disease arising after a selection process for cells with acquired functional capabilities like enhanced survival/resistance towards apoptosis and limitless proliferative potential. Thus, it is preferred to develop drugs for cancer therapy targeting several features of an established tumor. Kinase inhibitors with a defined, pathophysiological inhibition profile are preferred. As an example, Glivec potently inhibits not only the bcr-abl kinase, but also the platelet-derived growth factor receptor (PDGF-R) kinase and the c-kit receptor kinase. Other examples for kinases causally involved in tumor biology and cancer as a disease are the various vascular endothelial growth factor (VEGF) receptors, the insulin-like growth factor receptor (IGF1R) and downstream signalling kinases like phosphatidylinositol kinase (PI3K) and phosphoinositide-dependent kinase 1 (PDK1), the EGFR family including HER2, HER3 and HER4, the family of mitotic kinases including polo-like kinases (PLK) and Aurora kinase isoenzymes and raf isoenzymes including B-raf.

Within the class of serine-threonine specific signalling kinases, Akt (protein kinase B; PKB) with the isoenzmyes Akt1 (PKBα), Akt2 (PKB β) and Akt3 (PKB γ) is of high interest for therapeutic intervention. One pathway that has been shown to mediate important survival signals for mammalian cells comprises receptor tyrosine kinases like platelet-derived growth factor receptor (PDGF-R; Franke et al., Cell. 1995 Jun. 2; 81(5):727-36) or the insulin-like growth factor 1 receptor (IGF-1R; Kulik et al., Mol Cell Biol. 1997 March; 17(3):1595-606). After activation by ligand, these receptors activate the PI3K pathway. One aspect of PI3K activation is to protect cells from programmed cell death ("apoptosis") and is hence considered to transduce a survival signal to a cell. This signal is counteracted by the lipid phosphatase PTEN (phosphatase and tensin homolog), cleaving the PI3K product PI(3, 4, 5)P$_3$ by removing the 3' phosphate. PTEN is deleted or functionally inactivated in many cancer cells, leading to a constitutive survival signal. The phosphatidylinositide lipid produced by PI3K can stimulate multiple kinases, including protein kinase B/Akt, which is a central downstream mediator of anti-apoptotic signals transmitted by PI3K (Datta et al., Genes Dev. 1999 Nov. 15; 13(22):2905-27. Review). The amino terminus of the Akt enzymes contains a PH domain that recruits the protein to the cell membrane by binding to the PI3K product PI(3, 4, 5)P$_3$ and PI(3, 4,)P$_2$ leading to a conformational change. This conformational change allows Akt to be phosphorylated at threonine 308 and serine 473 (numbering of residues according to human Akt1) by the kinase PDK1 and a postulated kinase PDK2. A number of potential substrates within the apoptotic machinery have been identified that are phosphorylated by Akt within the consensus sequence RXRXXS/T. The first Akt substrate identified was glycogen synthase kinase 3 (GSK3; Cross et al., Nature. 1995 Dec. 21-28; 378(6559):785-9) and phosphorylation of GSK3 at serine 9 results in its inactivation. Besides regulating glycogen synthesis, GSK3 is involved in the regulation of several intracellular signaling pathways including adaptor protein complex 1 (AP1), cAMP-response-element-binding protein (CREB), and the tumor suppressor gene product anaphase promoting complex (APC). Phosphorylation of the pro-apoptotic protein Bcl2 antagonist of cell death (Bad) at serine 136 by Akt creates a binding site for 14-3-3 proteins and thereby prevents Bad from binding and inhibiting the anti-apoptotic protein Bcl-xL (Datta et al., Cell. 1997 Oct. 17; 91(2):231-41). Similarly, phosphorylation of the forkhead transcription factor Forkhead in rhabdomyosarcoma-like 1 (FKHRL1) by Akt at threonine 32 and serine 253 creates a binding motif for 14-3-3 proteins resulting in cytoplasmic retention of FKHRL1 (Brunet et al., Cell. 1999 Mar. 19; 96(6):857-68); resulting in downregulation of the pro-apoptotic Fas ligand. Caspases are intracellular proteases that function as initiators and effectors of apoptosis. Akt directly phosphorylates caspase-9 at serine 196 and inhibits its protease activity (Cardone et al., Science. 1998 Nov. 13; 282(5392):1318-21). Activation of the nuclear factor kappa B (NFκB) pathway by Akt has been demonstrated by the direct association of Akt with inhibitor of nuclear factor kappa B kinase (Ikk). In vitro phosphorylation of Ikk by Akt is supposed to enhance the degradation of IκB and consequently the translocation of NFκB into the nucleus (Ozes et al., Nature. 1999 Sep. 2; 401(6748):82-5).

Constitutive activation of Akt is frequently found in human ovarian, breast (Stal et al., Breast Cancer Res., 2003, 5, R37-44), and prostate carcinomas (Malik et al., Clinc. Cancer Res., 2002, 8, 1168-1171; Thakkar et al., J. Biol. Chem., 2001, 276, 38361-38369). It is due to a complete loss of the lipid phosphatase PTEN, a negative regulator of the PI3 kinase pathway (Nesterov et al., J. Biol. Chem., 2001, 276, 10767-10774). Inhibitors of Akt are therefore promising drugs for cancer therapy as effective sensitizers or inducers of apoptosis (Beresford et al., J. Interferon Cytokine Res., 2001, 21, 313-322).

By acting as a modulator of anti-apoptotic signalling in tumor cells, the protein kinase B (PKB)/Akt is a target for cancer therapy. Compounds interfering selectively with Akt isoenzmyes have been described recently (Barneft et al. Biochem. J 2005, 385:399-408). These Akt inhibitors, particular inhibitors of Akt 1 and Akt 2, selectively sensitized tumor cells to apoptotic stimuli like Trail, Camptothecin and Doxorubicin (DeFeo-Jones et al. Mol Cancer Therap 2005, 4:271-279). Akt inhibitors therefore are expected to shift the apoptotic threshold, resensitizing tumor cells towards apoptotic stimuli of eg chemotherapeutic agents or agonists of death receptor pathways, eg Trail or agonistic DR4/5 antibodies. Nevertheless, dependent on the genetic background/molecular apperations of the tumor, Akt inhibitors might induce apoptotic cell death in monotherapy as well.

PRIOR ART

The International Application WO 03/037891 contains notionally inter alia generically disclosed N-acylated meta-phenylenediamine derivatives which are said to be glycogen synthase kinase 3 (GSK3) inhibitors. WO 02/094831 describes pyridylmethylaminopyrimidines which have activity against *Helicobacter* bacteria. WO 01/47897 relates to N-heterocyclic compounds that are said to be effective in blocking cytokine production, and in particular the expression of TNF-alpha (TNF-α), via inhibition of p38 kinase. Hadas Reuveni et al., Biochemistry 2002, 41, 10304-10314 describes a screening method for inhibitors of the protein kinase B/Akt (PKB). WO 2004/048365 discloses pyrimidine based compounds which are said to inhibit the phosphotidylinositol (PI) 3-kinase.

DESCRIPTION OF THE INVENTION

It has now been found that the pyrimidine derivatives, which are described in greater details below, differ from prior art compounds by unanticipated specific structural features and have surprising and particularly advantageous properties. Thus, e.g. these pyrimidine derivatives act as inhibitors of protein kinases, in particular one or more isoforms of the protein kinase B (PKB)/Akt.

The invention thus relates in one embodiment (embodiment 1) of a first aspect (aspect a) to compounds of formula I

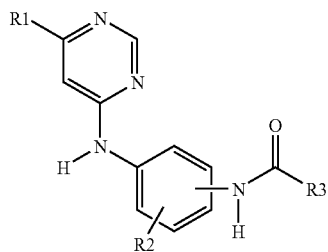

(I)

in which
R1 is Ar1, Har1, Aa1, Hh1, Ah1, or Ha1, in which
Ar1 is phenyl, R11- and/or R12-substituted phenyl, naphthyl, R13-substituted naphthyl, or fluorenyl, in which
R11 is 1-4C-alkoxy, 1-4C-alkoxy-2-4C-alkoxy, halogen, phenoxy, 1-4C-alkylcarbonyl or phenyl-1-4C-alkoxy,
R12 is 1-4C-alkoxy,
R13 is 1-4C-alkoxy,
Har1 is optionally substituted by R14 and is a monocyclic, fused bi- or tricyclic 5- to 14-membered heteroaryl radical comprising one to three heteroatoms, each of which is selected from the group consisting of nitrogen, oxygen and sulfur, in which
R14 is 1-4C-alkyl or phenylsulphonyl,
Aa1 is optionally substituted by R15 and is a bisaryl radical made up of two aryl groups, which are selected independently from a group consisting of phenyl and naphthyl, and which are linked together via a single bond, and in which
R15 is halogen,
Hh1 is a bisheteroaryl radical made up of two heteroaryl groups,
which are selected independently from a group consisting of monocyclic 5- or 6-membered heteroaryl radicals comprising one or two heteroatoms, each of which is selected from the group consisting of nitrogen, oxygen and sulfur, and
which are linked together via a single bond,
Ah1 is an arylheteroaryl radical made up of an aryl group selected from a group consisting of phenyl and naphthyl, and a heteroaryl group selected from a group consisting of monocyclic 5- or 6-membered heteroaryl radicals comprising one or two heteroatoms, each of which is selected from the group consisting of nitrogen, oxygen and sulfur, whereby said aryl and heteroaryl groups are linked together via a single bond,
Ha1 is a heteroarylaryl radical made up of a heteroaryl group selected from a group consisting of monocyclic 5- or 6-membered heteroaryl radicals comprising one or two heteroatoms, each of which is selected from the group consisting of nitrogen, oxygen and sulfur, and an aryl group selected from a group consisting of phenyl and naphthyl, whereby said heteroaryl and aryl groups are linked together via a single bond,
R2 is hydrogen, halogen or 1-4C-alkyl,
R3 is —U—Ar2, or —V—Har2, in which
U is a bond, 1-4C-alkylene, or 1-4C-alkylene substituted with amino-1-4C-alkyl,
Ar2 is phenyl, or R31- and/or R32- and/or R321-substituted phenyl, in which
R31 is 1-C-alkyl, 1-4C-alkoxy, halogen, nitro, trifluoromethyl, cyano, amidino, or —W—R311, in which W is a bond or 1-4C-alkylene,
R311 is —N(R312)R313, halogen, or Het1, in which
R312 is hydrogen, 1-4C-alkyl, 1-4C-alkoxycarbonyl or 1-4C-alkoxy-2-4C-alkyl,
R313 is hydrogen, 1-4C-alkyl or 1-4C-alkoxy-2-4C-alkyl,
Het1 is optionally substituted by R314 and is a monocylic 3- to 7-membered saturated heterocyclic ring,
which comprises one or two heteroatoms selected from a group consisting of oxygen, nitrogen and sulfur, and
which is bonded to the moiety W via a ring carbon atom or via a ring nitrogen atom, and in which
R314 is 1-4C-alkyl or 1-4C-alkoxycarbonyl,
R32 is 1-4C-alkoxy or halogen, or
R31 and R32 bonded to the phenyl ring in ortho position to each other form together a 1-2C-alkylenedioxy group,
R321 is 1-4C-alkoxy,
V is a bond,
Har2 is optionally substituted by R33 and/or R34 and is a monocyclic or fused bicyclic 5- to 10-membered unsaturated or partially saturated heteroaryl radical comprising one to three heteroatoms, each of which is selected from the group consisting of nitrogen, oxygen and sulfur, in which
R33 is 1-4C-alkyl, trifluoromethyl, cyano, or —W—R311,
R34 is 1-4C-alkyl, and the salts of these compounds.

The invention further relates in another embodiment (embodiment 2) of a first aspect (aspect a) to compounds of formula I in which R1 is Ar1 or Har1, in which Ar1 is fluorenyl, Har1 is optionally substituted by R14 and is a fused tricyclic 13- or 14-membered heteroaryl radical comprising one to three heteroatoms, each of which is selected from the group consisting of nitrogen, oxygen and sulfur, in which R14 is 1-4C-alkyl or phenylsulphonyl, R2 is hydrogen, halogen or 1-4C-alkyl, R3 is —U—Ar2, or —V—Har2, in which U is a bond, 1-4C-alkylene, or 1-4C-alkylene substituted with amino-1-4C-alkyl, Ar2 is phenyl, or R31- and/or R32- and/or R321-substituted phenyl, in which R31 is 1-4C-alkyl, 1-4C-alkoxy, halogen, nitro, trifluoromethyl, cyano, amidino, or —W—R311, in which W is a bond or 1-4C-alkylene, R311 is —N(R312)R313, halogen, or Het1, in which R312 is hydrogen, 1-4C-alkyl, 1-4C-alkoxycarbonyl or 1-4C-alkoxy-2-4C-alkyl, R313 is hydrogen, 1-4C-alkyl or 1-4C-alkoxy-2-4C-alkyl, Het1 is optionally substituted by R314 and is a monocylic 3- to 7-membered saturated heterocyclic ring,
which comprises one or two heteroatoms selected from a group consisting of oxygen, nitrogen and sulfur, and
which is bonded to the moiety W via a ring carbon atom or via a ring nitrogen atom, and in which R314 is 1-4C-alkyl or 1-4C-alkoxycarbonyl, R32 is 1-4C-alkoxy or halogen, or R31 and R32 bonded to the phenyl ring in ortho position to each other form together a 1-2C-alkylenedioxy group, R321 is 1-4C-alkoxy, V is a bond, Har2 is optionally substituted by R33 and/or R34 and is a monocyclic or fused bicyclic 5- to 10-membered unsaturated or partially saturated heteroaryl radical comprising one to three heteroatoms, each of which is selected from the group consisting of nitrogen, oxygen and sulfur, in which R33 is 1-4C-alkyl, trifluoromethyl, cyano, or —W—R311, R34 is 1-4C-alkyl, and the salts of these compounds.

1-4C-Alkyl represents a straight-chain or branched alkyl radical having 1 to 4 carbon atoms. Examples which may be mentioned are the butyl, isobutyl, sec-butyl, tert-butyl, propyl, isopropyl and preferably the ethyl and methyl radicals.

2-4C-Alkyl represents a straight-chain or branched alkyl radical having 2 to 4 carbon atoms. Examples which may be mentioned are the butyl, isobutyl, sec-butyl, tert-butyl, propyl, isopropyl and preferably the ethyl and propyl radicals.

1-4C-Alkylene is a straight or branched chain alkylene radical having 1 to 4 carbon atoms. Examples which may be mentioned as straight chain alkylene radicals are methylene (—$CH_2$—), ethylene (—$CH_2$—$CH_2$—), trimethylene (—$CH_2$—$CH_2$—$CH_2$—) and the tetramethylene (—$CH_2$—$CH_2$—$CH_2$—$CH_2$—) radical. An example which may be mentioned as branched chain alkylene radical is the 1,1-dimethyl-methylene radical.

1-4C-Alkoxy represents radicals which, in addition to the oxygen atom, contain a straight-chain or branched alkyl radical having 1 to 4 carbon atoms. Examples which may be mentioned are the butoxy, isobutoxy, sec-butoxy, tert-butoxy, propoxy, isopropoxy and preferably the ethoxy and methoxy radicals.

2-4C-Alkoxy represents radicals which, in addition to the oxygen atom, contain a straight-chain or branched alkyl radical having 2 to 4 carbon atoms. Examples which may be mentioned are the butoxy, isobutoxy, sec-butoxy, tert-butoxy, propoxy, isopropoxy and preferably the ethoxy radicals.

1-4C-Alkoxy-2-4C-alkoxy represents one of the abovementioned 2-4C-alkoxy radicals, which is substituted by one of the abovementioned 1-4C-alkoxy radicals. Examples which may be mentioned are the 2-methoxyethoxy, 2-ethoxyethoxy and the 2-isopropoxyethoxy radicals.

Phenyl-1-4C-alkoxy represents one of the abovementioned 1-C-alkoxy radicals, which is substituted by a phenyl radical. Examples which may be mentioned are the phenethoxy and the benzyloxy radicals.

1-4-C-Alkoxy-2-4C-alkyl represents one of the abovementioned 2-4C-alkyl radicals, which is substituted by one of the abovementioned 1-4C-alkoxy radicals. Examples which may be mentioned are the 2-methoxyethyl, 2-ethoxyethyl and the 2-isopropoxyethyl radicals.

1-2C-Alkylenedioxy represents, for example, the methylenedioxy [—O—$CH_2$—O—] and the ethylenedioxy [—O—$CH_2$—$CH_2$—O—] radicals.

Amino-1-4C-alkyl represents one of the abovementioned 1-4C-alkyl radicals, which is substituted by an amino radical. Examples which may be mentioned are the aminomethyl, 2-aminoethyl and the 3-aminopropyl radicals.

"1-4C-Alkylene substituted with amino-1-4C-alkyl" may include, for example, one of the abovementioned 1-4C-alkylene radicals, particularly one of the abovementioned straight chain alkylene radicals, such as, for example, the amino-1-4C-alkyl-methylene radicals, e.g. the aminomethyl-methylene radical.

Halogen within the meaning of the invention is bromine, chlorine or fluorine.

1-4C-Alkylcarbonyl represents a radical which, in addition to the carbonyl group, contains one of the abovementioned 1-4C-alkyl radicals. An example which may be mentioned is the acetyl radical.

1-4C-Alkoxycarbonyl represents a radical which, in addition to the carbonyl group, contains one of the abovementioned 1-4C-alkoxy radicals. Examples which may be mentioned are the methoxycarbonyl, the ethoxycarbonyl and the tertbutoxycarbonyl radicals.

In the meaning of the present invention, it is to be understood, that, when two structural portions of the compounds according to this invention are linked via a constituent which has the meaning "bond", then said two portions are directly attached to another via a single bond.

Har1 is optionally substituted by R14 and is a monocyclic, fused bi- or tricyclic 5- to 14-membered heteroaryl radical comprising one to three heteroatoms, each of which is selected from the group consisting of nitrogen, oxygen and sulfur. In more detail, Har1 is attached to the pyrimidine moiety via a ring carbon atom. Preferably, Har1 is optionally substituted by R14 on a ring nitrogen atom.

A first embodimental subdetail of Har1 according to this invention includes the monocyclic radicals such as, without being restricted thereto, furanyl, thiophenyl, pyrrolyl, oxazolyl, isoxazolyl, thiazolyl, isothiazolyl, imidazolyl, pyrazolyl, triazolyl, thiadiazolyl, oxadiazolyl, pyridinyl, pyrimidinyl, pyrazinyl or pyridazinyl.

A second embodimental subdetail of Har1 according to this invention includes the bicyclic radicals such as, without being restricted thereto, benzo-fused analogues of the aforementioned monocyclic radicals like e.g. quinazolinyl, quinoxalinyl, cinnolinyl, quinolinyl, isoquinolinyl, indolyl, isoindolyl, indazolyl, phthalazinyl, benzothiophenyl, benzofuranyl, isobenzofuranyl, benzoxazolyl, benzothiazolyl or benzimidazolyl, or naphthyridinyl, indolizinyl or purinyl.

A third embodimental subdetail of Har1 according to this invention includes the tricyclic radicals such as, without being restricted thereto, carbazolyl, phenanthridinyl, acridinyl, carbolinyl, phenazinyl, dibenzofuranyl, dibenzothiophenyl, phenothiazinyl, phenoxazinyl, phenoxathiinyl or thianthrenyl.

As further examples for Har1 according to this invention may be mentioned, without being restricted thereto, R14-substituted derivatives of the abovementioned exemplary Har1 radicals, notably Har1 radicals, which are substituted by R14 on a ring nitrogen atom and which are selected from a group consisting of pyrrolyl, imidazolyl, pyrazolyl, triazolyl, thiadiazolyl, oxadiazolyl, indolyl, isoindolyl, indazolyl, benzoxazolyl, benzimidazolyl, carbazolyl, carbolinyl, purinyl, phenothiazinyl or phenoxazinyl.

As exemplary Har1 radicals may be more precisely mentioned, for example, dibenzofuranyl, indolyl, quinolinyl, pyridinyl, benzothiophenyl, thianthrenyl, dibenzothiophenyl, N-phenylsulphonylindolyl or N-methylindolyl.

As exemplary Har1 radicals may be further more precisely mentioned, for example, dibenzofuran-4-yl, indol-2-yl, indol-5-yl, indol-6-yl, benzothiophen-2-yl, benzothiophen-3-yl, thianthren-1-yl, dibenzothiophen-4-yl, N-phenylsulphonylindol-2-yl, or quinolin-3-yl.

As exemplary suitable Har1 radicals may be explicitly mentioned, for example, thianthren-1-yl, dibenzothiophen-4-yl, or, especially, dibenzofuran-yl.

Aa1 is optionally substituted by R15 and is a bisaryl radical made up of two aryl groups, which are selected independently from a group consisting of phenyl and naphthyl, and which are linked together via a single bond.

Aa1 may include, without being restricted thereto, the biphenyl radical (e.g. the 1,1'-biphen-4-yl radical) and the R15-substituted derivatives thereof (e.g. 4'-fluoro-1,1'-biphen-4-yl).

Hh1 is a bisheteroaryl radical made up of two heteroaryl groups, which are selected independently from a group consisting of monocyclic 5 or 6-membered heteroaryl radicals comprising one or two heteroatoms, each of which is selected from the group consisting of nitrogen, oxygen and sulfur, and which are linked together via a single bond.

Hh1 may include, without being restricted thereto, the bithiophenyl radical.

Ah1 is an arylheteroaryl radical made up of an aryl group selected from a group consisting of phenyl and naphthyl, and a heteroaryl group selected from a group consisting of monocyclic 5- or 6-membered heteroaryl radicals comprising one or two heteroatoms, each of which is selected from the group consisting of nitrogen, oxygen and sulfur, whereby said aryl and heteroaryl groups are linked together via a single bond, and whereby Ah1 is bonded via said heteroaryl moiety to the pyrimidine scaffold.

Ah1 may include, without being restricted thereto, the phenylthiophenyl radical.

Ha1 is a heteroarylaryl radical made up of a heteroaryl group selected from a group consisting of monocyclic 5- or 6-membered heteroaryl radicals comprising one or two heteroatoms, each of which is selected from the group consisting of nitrogen, oxygen and sulfur, and an aryl group selected from a group consisting of phenyl and naphthyl, whereby said heteroaryl and aryl groups are linked together via a single bond, and whereby Ha1 is bonded via said aryl moiety to the pyrimidine scaffold.

Ha1 may include, without being restricted thereto, the thiophenylphenyl radical.

It is to be understood, that each of the radicals Har1, Hh1 and Ah1 is bonded to the pyrimidine scaffold via a ring carbon atom.

Het1 is optionally substituted by R314 and is a monocylic 3- to 7-membered saturated heterocyclic ring, which comprises one or two heteroatoms selected from a group consisting of oxygen, nitrogen and sulfur, and which is bonded to the moiety W via a ring carbon atom or via a ring nitrogen atom.

In more detail, Het1 is optionally substituted by R314 on a ring nitrogen atom.

Het1 may include, without being restricted thereto, aziridin-1-yl, azetidin-1-yl, pyrrolidin-1-yl, piperidin-1-yl, homopiperidin-1-yl, pyrazolidin-1-yl, imidazolidin-1-yl, piperazin-1-yl, homopiperazin-1-yl, morpholin-4-yl, thiomorpholin-yl, piperidin-3-yl or piperidinyl.

As further examples for Het1 according to this invention may be mentioned, without being restricted thereto, R314-substituted derivatives of the abovementioned exemplary Het1 radicals, notably Het1 radicals, which are substituted by R314 on a ring nitrogen atom and which are selected from a group consisting of pyrazolidin-1-yl, imidazolidin-1-yl, piperazin-1-yl, homopiperazin-1-yl, piperidin-3-yl and piperidin-4-yl.

As exemplary Het1 radicals may be more precisely mentioned, for example, morpholin-4-yl, pyrrolidin-1-yl, 4-N-methyl-piperazin-1-yl or piperidin-3-yl.

As exemplary suitable Het1 radicals may be explicitly mentioned, for example, pyrrolidin-1-yl or piperidin-3-yl.

Har2 is optionally substituted by R33 and/or R34 and is a monocyclic or fused bicyclic 5- to 10-membered unsaturated or partially saturated heteroaryl radical comprising one to three heteroatoms, each of which is selected from the group consisting of nitrogen, oxygen and sulfur. In more detail, Har2 is attached to the moiety V via a ring carbon atom. Preferably, Har2 is optionally substituted by R33 and/or R34 on a ring carbon atom.

One embodiment of Har2 according to this invention includes the unsaturated radicals, such as e.g., without being restricted thereto, furanyl, thiophenyl, pyrrolyl, oxazolyl, isoxazolyl, thiazolyl, isothiazolyl, imidazolyl, pyrazolyl, triazolyl, thiadiazolyl, oxadiazolyl, pyridinyl, pyrimidinyl, pyrazinyl, pyridazinyl, benzo-fused analogues thereof such as, for example, quinazolinyl, quinoxalinyl, cinnolinyl, quinolinyl, isoquinolinyl, indolyl, isoindolyl, indazolyl, phthalazinyl, benzothiophenyl, benzofuranyl, isobenzofuranyl, benzoxazolyl, benzothiazolyl or benzimidazolyl, or naphthyridinyl, indolizinyl or purinyl.

Har2 may also include in another embodiment the partially hydrogenated derivatives of the ring systems enumerated above, particularly the partially hydrogenated derivatives of the abovementioned benzo-fused radicals, such as, for example, without being restricted thereto, indolinyl, isoindolinyl, 1,2,3,4-tetrahydroquinolinyl or 1,2,3,4-tetrahydroisoquinolinyl.

As further examples for Har2 according to this invention may be mentioned, without being restricted thereto, R33- and/or R34-substituted derivatives of the abovementioned exemplary Har2 radicals.

As exemplary Har2 radicals may be more precisely mentioned, for example, furanyl, dimethylfuranyl, dimethylisoxazolyl, methylisoxazolyl, pyridinyl, trifluoromethylpyridinyl, aminopyridinyl, chloropyridinyl, fluoropyridinyl, (aminomethyl)pyridinyl, 1,2,3,4-tetrahydroisoquinolinyl, aminomethylfuranyl, (morpholinyl)pyridinyl or cyanopyridinyl.

As exemplary Har2 radicals may be further more precisely mentioned, for example, furan-2-yl, 2,5-dimethylfuran-3-yl, 3,5-dimethylisoxazol-4-yl, 5-methylisoxazol-3-yl, 6-trifluoromethylpyridin-3-yl, pyridin-4-yl, 6-(aminomethyl)-pyridin-2-yl, 6-(aminomethyl)-pyridin-3-yl, 5-(aminomethyl)-pyridin-3-yl, 2-(aminomethyl)-pyridin-4-yl, 4-(aminomethyl)-pyridin-2-yl, 5-(aminomethyl)-pyridin-2-yl, 1,2,3,4-tetrahydroisoquinolinyl, 6-(morpholin-4-yl)-pyridin-3-yl, 5-cyano-pyridin-3-yl, or 6-cyano-pyridin-3-yl.

As exemplary suitable Har2 radicals may be explicitely mentioned, for example, (aminomethyl)pyridinyl, such as e.g. 6-(aminomethyl)-pyridin-2-yl, 6-(aminomethyl)-pyridin-3-yl, 5-(aminomethyl)-pyridin-3-yl, 2-(aminomethyl)-pyridin-4-yl, 4-(aminomethyl)-pyridin-2-yl, 5-(aminomethyl)-pyridin-2-yl, or 1,2,3,4-tetrahydroisoquinolin-7-yl or 1,2,3,4-tetrahydroisoquinolin-6-yl.

Unless otherwise noted, the cyclic radicals mentioned herein refers to all possible and stable positional isomers. Thus, for example, pyridinyl or pyridyl includes pyridin-2-yl, pyridin-3-yl and pyridin-4-yl.

Suitable salts for compounds of the formula I—depending on substitution—are all acid addition salts or all salts with bases. Particular mention may be made of the pharmacologically tolerable inorganic and organic acids and bases customarily used in pharmacy. Those suitable are, on the one hand, water-insoluble and, particularly, water-soluble acid addition salts with acids such as, for example, hydrochloric acid, hydrobromic acid, phosphoric acid, nitric acid, sulphuric acid, acetic acid, citric acid, D-gluconic acid, benzoic acid, 2-(4-hydroxybenzoyl)benzoic acid, butyric acid, sulphosalicylic acid, maleic acid, lauric acid, malic acid, fumaric acid, succinic acid, oxalic acid, tartaric acid, embonic acid, stearic acid, toluenesulphonic acid, methanesulphonic acid or 3-hydroxy-2-naphthoic acid, the acids being employed in salt preparation—depending on whether a mono- or polybasic acid is concerned and depending on which salt is desired—in an equimolar quantitative ratio or one differing therefrom.

On the other hand, salts with bases are—depending on substitution—also suitable. As examples of salts with bases are mentioned the lithium, sodium, potassium, calcium, aluminium, magnesium, titanium, ammonium, meglumine or guanidinium salts, here, too, the bases being employed in salt preparation in an equimolar quantitative ratio or one differing therefrom.

Pharmacologically intolerable salts, which can be obtained, for example, as process products during the preparation of the compounds according to the invention on an industrial scale, are converted into pharmacologically tolerable salts by processes known to the person skilled in the art.

According to expert's knowledge the compounds of formula I of the invention as well as their salts may contain, e.g. when isolated in crystalline form, varying amounts of solvents. Included within the scope of the invention are therefore all solvates and in particular all hydrates of the compounds of formula I as well as all solvates and in particular all hydrates of the salts of the compounds of formula I.

Constituents which are described herein as substituted, may be substituted, unless otherwise noted, at any possible position.

In general, unless otherwise noted, the carbocydic groups, alone or as part of other groups, mentioned herein may be substituted by their given substituents or parent molecular groups at any substitutable ring carbon atom.

Unless otherwise noted, the heterocyclic groups, alone or as part of other groups, mentioned herein may be substituted by their given substituents or parent molecular groups at any possible position, such as e.g. at any substitutable ring carbon or ring nitrogen atom.

Rings containing quaternizable imino-type ring nitrogen atoms (—N═) may be preferably not quaternized on these imino-type ring nitrogen atoms by the mentioned substituents or parent molecular groups.

The substituents R2 and —N(H)C(O)R3 of compounds of formula I can be attached in the ortho, meta or para position with respect to the binding position in which the phenyl ring is bonded to the pyrimidine-amino moiety, whereby preference is given to the attachment of —N(H)C(O)R3 in the meta or, particularly, in the para position.

The substituents R11 and R12 of compounds of formula I can be attached in the ortho, meta or para position with respect to the binding position in which the phenyl ring is bonded to the pyrimidine moiety, whereby preference is given to the attachment in the meta or in the para position.

The substituents R31, R32 and R321 of compounds of formula I can be attached in the ortho, meta or para position with respect to the binding position in which the phenyl ring is bonded to the moiety U, whereby emphasis is given to the attachment in the meta or in the para position.

As exemplary Ar1 radicals may be mentioned, without being restricted thereto, 3-benzyloxy-phenyl, 4-benzyloxy-phenyl, phenyl, 3-methoxy-phenyl, 4-methoxy-phenyl, 3,4-dimethoxy-phenyl, 3,5-dimethoxy-phenyl, 3-fluoro-phenyl, 4-fluoro-phenyl, 3-acetyl-phenyl, 4-acetyl-phenyl, 3-phenoxy-phenyl or 4-phenoxy-phenyl, or 6-methoxy-naphthalen-2-yl.

Illustrative exemplary Ar1 radicals may include, without being restricted thereto, 3-benzyloxy-phenyl, 4-benzyloxy-phenyl, phenyl, 3-methoxy-phenyl, 4-methoxy-phenyl, 3,4-dimethoxy-phenyl, 3-fluoro-phenyl, 3-acetyl-phenyl, 4-acetyl-phenyl or 4-phenoxy-phenyl, or 6-methoxy-naphthalen-2-yl.

As exemplary Ar2 radicals may be mentioned, without being restricted thereto, 4-dimethylamino-phenyl, 3-dimethylamino-phenyl, 2-dimethylamino-phenyl, 4-(morpholin-4-yl)-phenyl, 3-(morpholin-4-yl)-phenyl, 4-(pyrrolidin-1-yl)-phenyl, 3-(pyrrolidin-1-yl)-phenyl, 4-(4-methylpiperazin-1-yl-methyl)-phenyl, 3-(4-methylpiperazin-1-yl-methyl)-phenyl, phenyl, 4-tert-butyl-phenyl, 3,4-dichlorophenyl, 2,6-difluoro-phenyl, 4-aminomethyl-phenyl, 3-aminomethyl-phenyl, 2-aminomethyl-phenyl, 4-(2-aminoethyl)-phenyl, 3-(2-aminoethyl)-phenyl, 4-dimethylaminomethyl-phenyl, 3-dimethylaminomethyl-phenyl, 4-methylaminomethyl-phenyl, 3-methylaminomethyl-phenyl, 2-amino-phenyl, 3-amino-phenyl, 4-amino-phenyl, 4-(piperidin-3-yl)-phenyl, 3-(piperidin-3-yl)-phenyl, 4-(morpholin-4-ylmethyl)-phenyl, 3-(morpholin-4-ylmethyl)-phenyl, 4-{[bis-(2-methoxyethyl)]amino}-phenyl, 3-{[bis-(2-methoxyethyl)]amino}-phenyl, 4-[(2-methoxyethyl)amino]-phenyl, 3-[(2-methoxyethyl)amino]-phenyl, 4-(2-chloroethyl)-phenyl, 3-(2-chloroethyl)-phenyl, 4-bromomethyl-phenyl, 3-bromomethyl-phenyl, 3-cyano-phenyl, 4-cyano-phenyl, 3-amidino-phenyl, 4-amidino-phenyl, 4-aminomethyl-2-fluoro-phenyl, 4-(1-amino-1-methyl-ethyl)-phenyl, 3-(1-amino-1-methyl-ethyl)-phenyl, 3,4-methylenedioxy-phenyl, 3,4-ethylenedioxy-phenyl, 4-fluorophenyl, 3-fluorophenyl, 2-fluorophenyl, 3-methoxyphenyl, 4-methoxyphenyl, 2-methoxyphenyl, 3,4,5-trimethoxy-phenyl, 3,5-dimethoxyphenyl, 3,4-dimethoxy-phenyl, 4-fluoro-3-trifluoromethyl-phenyl, 4-chloro-2-fluoro-phenyl, or 3-chloro-4-fluoro-phenyl.

Illustrative exemplary Ar2 radicals may include, without being restricted thereto, 4-dimethylamino-phenyl, 3-dimethylamino-phenyl, 2-dimethylamino-phenyl, 4-(morpholin-4-yl)-phenyl, 3-(pyrrolidin-1-yl)-phenyl, 4-(4-methylpiperazin-1-yl-methyl)-phenyl, phenyl, 4-tert-butyl-phenyl, 3,4-dichlorophenyl, 4-aminomethyl-phenyl, 3-aminomethyl-phenyl, 3-(2-aminoethyl)-phenyl, 4-(2-aminoethyl)-phenyl, 3-dimethylaminomethyl-phenyl, 4-dimethylaminomethyl-phenyl, 4-methylaminomethyl-phenyl, 2-amino-phenyl, 3-amino-phenyl, 4-amino-phenyl, 4-(piperidin-3-yl)-phenyl, 4-(morpholin-4-ylmethyl)-phenyl, 3-{[bis-(2-methoxy-ethyl)]amino}-phenyl, 4-[(2-methoxyethyl)amino]-phenyl, 4-(2-chloroethyl)-phenyl, 4-bromomethyl-phenyl, 3-cyano-phenyl, 4-cyano-phenyl, 3-amidino-phenyl, 4-amidino-phenyl, 4-aminomethyl-2-fluoro-phenyl, 4-(1-amino-1-methyl-ethyl)-phenyl, 3,4-methylenedioxy-phenyl, 4-fluorophenyl, 3-fluorophenyl, 2-fluorophenyl, 3-methoxyphenyl, 4-methoxyphenyl, 3,4,5-trimethoxy-phenyl, 3,5-dimethoxy-phenyl, 3,4-dimethoxy-phenyl, 4-fluoro-3-trifluoromethyl-phenyl, 2,6-difluoro-phenyl, 4-chloro-2-fluoro-phenyl, or 3-chloro-4-fluoro-phenyl.

Compounds according to embodiment 1 of aspect a of this invention more worthy to be mentioned include those compounds of formula I, in which
R1 is Ar1, Har1, or Aa1, in which
Ar1 is phenyl, R11- and/or R12-substituted phenyl, naphthyl, or R13-substituted naphthyl, in which
R11 is 1-4C-alkoxy, halogen, phenoxy, 1-C-alkylcarbonyl or phenyl-1-4C-alkoxy,
R12 is 1-4C-alkoxy,
R13 is 1-4C-alkoxy,
Har1 is optionally substituted by R14 and is a monocyclic, fused bi- or tricyclic 5- to 14-membered heteroaryl radical comprising one to three heteroatoms, each of which is selected from the group consisting of nitrogen, oxygen and sulfur, in which
R14 is phenylsulphonyl,
Aa1 is optionally substituted by R15 and is a bisaryl radical made up of two aryl groups, which are selected independently from a group consisting of phenyl and naphthyl, and which are linked together via a single bond, and in which
R15 is halogen,
Hh1 is a bisheteroaryl radical made up of two heteroaryl groups,
which are selected independently from a group consisting of monocyclic 5- or 6-membered heteroaryl radicals comprising one or two heteroatoms, each of which is selected from the group consisting of nitrogen, oxygen and sulfur, and
which are linked together via a single bond,
Ah1 is an arylheteroaryl radical made up of an aryl group selected from a group consisting of phenyl and naphthyl, and a heteroaryl group selected from a group consisting of monocyclic 5- or 6-membered heteroaryl radicals comprising one or two heteroatoms, each of which is selected from the group consisting of nitrogen, oxygen and sulfur, whereby said aryl and heteroaryl groups are linked together via a single bond,
Ha1 is a heteroarylaryl radical made up of a heteroaryl group selected from a group consisting of monocyclic 5- or 6-membered heteroaryl radicals comprising one or two heteroatoms, each of which is selected from the group consisting of nitrogen, oxygen and sulfur, and an aryl group selected from a group consisting of phenyl and naphthyl, whereby said heteroaryl and aryl groups are linked together via a single bond,
R2 is hydrogen or 1-4C-alkyl,
R3 is —U—Ar2, or —V—Har2, in which
U is a bond, straight chain 1-4C-alkylene, or straight chain 1-4C-alkylene substituted with amino-1-4C-alkyl,
Ar2 is phenyl, or R31- and/or R32- and/or R321-substituted phenyl, in which
R31 is 1-4C-alkyl, 1-4C-alkoxy, halogen, nitro, trifluoromethyl, cyano, amidino, —W—R311, or Het1, in which
W is a bond or 1-4C-alkylene,
R311 is —N(R312)R313, or halogen, in which
R312 is hydrogen, 1-4C-alkyl, 1-4C-alkoxycarbonyl or 1-4C-alkoxy-2-4C-alkyl,
R313 is hydrogen, 1-4C-alkyl or 1-4C-alkoxy-2-4C-alkyl,
Het1 is optionally substituted by R314 and is a monocylic 3- to 7-membered saturated heterocyclic ring,
which comprises one or two heteroatoms selected from a group consisting of oxygen, nitrogen and sulfur, and
which is bonded to the moiety W via a ring carbon atom or via a ring nitrogen atom, and in which
R314 is 1-4C-alkyl or 1-4C-alkoxycarbonyl,
R32 is 1C-alkoxy or halogen, or
R31 and R32 bonded to the phenyl ring in ortho position to each other form together a 1-2C-alkylenedioxy group,
R321 is 1-4C-alkoxy,
V is a bond,
Har2 is optionally substituted by R33 and/or R34 and is a monocyclic or fused bicyclic 5 to 10-membered unsaturated or partially saturated heteroaryl radical comprising one to three heteroatoms, each of which is selected from the group consisting of nitrogen, oxygen and sulfur, in which
R33 is 1-4C-alkyl, trifluoromethyl, cyano, or —W—R311,
R34 is 1-4C-alkyl, and the salts of these compounds.

Compounds according to embodiment 1 of aspect a of this invention in particular worthy to be mentioned include those compounds of formulae I or, particularly, Ia as defined below, in which
R1 is dibenzofuran-4-yl, dibenzothiophen-4-yl, 4-benzyloxy-phenyl, 4-phenoxy-phenyl, or thianthren-1-yl,
R2 is hydrogen, or methyl,
R3 is —U—Ar2, —V—Har2, or 2-amino-phenyl, in which U is a bond, and
Ar2 is 3-(R31)-phenyl, 4-(R31)-phenyl, or 3-(R31)- or 4-(R31)-fluorophenyl, in which
R31 is 1-4C-alkoxy, 1-4C-alkyl, cyano, chlorine, amidino, —W—R311, pyrrolidin-1-yl, or piperidin-3-yl, in which
either
W is a bond, and
R311 is —N(R312)R313, in which
R312 is hydrogen, 1-4C-alkyl, 1-4C-alkoxy-ethyl, or tertbutoxycarbonyl,
R313 is hydrogen, or 1-4C-alkyl, or
W is methylene, ethylene, or 1,1-dimethyl-methylene,
R311 is —N(R312)R313, or bromine, in which
R312 is hydrogen, 1-4C-alkyl, or tertbutoxycarbonyl,
R313 is hydrogen, or 1-4C-alkyl, or
U is methylene, or ethylene, and
Ar2 is phenyl, or 3-(R31)- or 4-(R31)-phenyl, in which
R31 is fluorine, 1-4C-alkoxy, or aminomethyl, or
U is a bond, or aminomethyl-methylene, and
Ar2 is 3,4-dichlorophenyl,
V is a bond,
Har2 is 1,2,3,4-tetrahydroisoquinolinyl, isoindolinyl, or R33-substituted pyridyl, in which
R33 is aminomethyl, or trifluoromethyl, and the salts of these compounds.

Compounds according to embodiment 1 of aspect a of this invention in more particular worthy to be mentioned include those compounds of formula Ia as defined below, in which
R1 is dibenzothiophen-4-yl, 4-benzyloxy-phenyl, thianthren-1-yl, or, in particular, dibenzofuran-4-yl,
R2 is hydrogen, or methyl,
R3 is —U—Ar2, —V—Har2, or 2-amino-phenyl, in which
U is a bond, and
Ar2 is 3-(R31)-phenyl, 4-(R31)-phenyl, or 3-(R31)- or 4-(R31)-fluorophenyl, in which
R31 is amidino, —W—R311, pyrrolidin-1-yl, or piperidin-3-yl, in which
either
W is a bond,
R311 is —N(R312)R313, in which
R312 is hydrogen, methyl, or 2-methoxyethyl,
R313 is methyl, or
W is methylene, ethylene, or 1,1-dimethyl-methylene,
R311 is —N(R312)R313, in which
R312 is hydrogen, or methyl,
R313 is hydrogen, or
U is methylene, and
Ar2 is 4-(aminomethyl)-phenyl, or
U is aminomethyl-methylene, and
Ar2 is 3,4-dichlorophenyl,
V is a bond,
Har2 is 1,2,3,4-tetrahydroisoquinolinyl, isoindolinyl, or R33-substituted pyridyl, in which
R33 is aminomethyl, and the salts of these compounds.

Compounds according to embodiment 1 of aspect a of this invention to be emphasized are compounds of formula Ia as defined below, in which
R1 is dibenzofuran-4-yl,
R2 is hydrogen,
R3 is —U—Ar2, or —V—Har2, in which
U is a bond,
Ar2 is 3-(R31)-phenyl, 4-(R31)-phenyl, or 2-fluoro-4-(R31)-phenyl, in which
R31 is amidino, or —W—R311, in which
W is methylene, ethylene, or 1,1-dimethyl-methylene,
R311 is —N(R312)R313, in which
R312 is hydrogen, or methyl,
R313 is hydrogen,
V is a bond,
Har2 is 1,2,3,4-tetrahydroisoquinolin-7-yl, 1,2,3,4-tetrahydroisoquinolin-6-yl, or R33-substituted pyridyl, in which
R33 is aminomethyl, and the salts of these compounds.

In a first embodiment, compounds according to embodiment 1 of aspect a of this invention to be more emphasized are compounds of formula Ia as defined below, in which
R1 is dibenzofuran-4-yl,
R2 is hydrogen,
R3 is —U—Ar2, in which
U is a bond,
Ar2 is 3-(R31)-phenyl, or 4-(R31)-phenyl, in which
R31 is amidino, or —W—R311, in which
W is methylene,
R311 is —N(R312)R313, in which
R312 is hydrogen,
R313 is hydrogen, and the salts of these compounds.

In a second embodiment, compounds according to embodiment 1 of aspect a of this invention to be more emphasized are compounds of formula Ia as defined below, in which
R1 is dibenzofuran-4-yl,
R2 is hydrogen,
R3 is —V—Har2, in which
V is a bond,
Har2 is 1,2,3,4-tetrahydroisoquinolin-7-yl, 1,2,3,4-tetrahydroisoquinolin-6-yl, or R33-substituted pyridyl, in which
R33 is aminomethyl;

whereby, more precisely,
R1 is dibenzofuran-4-yl,
R2 is hydrogen,
R3 is —V—Har2, in which
V is a bond,
Har2 is 1,2,3,4-tetrahydroisoquinolin-7-yl, 1,2,3,4-tetrahydroisoquinolin-6-yl, 6-(R33)-pyrid-3-yl, 6-(R33)-pyrid-2-yl, 2-(R33)-pyrid-4-yl, 4-(R33)-pyrid-2-yl, or 5-(R33)-pyrid-2-yl, in which
R33 is aminomethyl;

and the salts of these compounds.

Compounds according to embodiment 2 of aspect a of this invention more worthy to be mentioned include those compounds of formula I, in which
R1 is Har1, in which
Har1 is carbazolyl, phenanthridinyl, acridinyl, carbolinyl, phenazinyl, dibenzofuranyl, dibenzothiophenyl, phenothiazinyl, phenoxazinyl, phenoxathiinyl, thianthrenyl, N-methyl-carbazolyl or N-methylcarbolinyl,
R2 is hydrogen or 1-4C-alkyl,
R3 is —U—Ar2, or —V—Har2, in which
U is a bond, straight chain 1-4C-alkylene, or straight chain 1-4C-alkylene substituted with amino-1-4C-alkyl,
Ar2 is phenyl, or R31- and/or R32- and/or R321-substituted phenyl, in which
R31 is 1-4C-alkyl, 1-4C-alkoxy, halogen, nitro, trifluoromethyl, cyano, amidino, —W—R311, or Het1, in which
W is a bond or 1-4C-alkylene,
R311 is —N(R312)R313, or halogen, in which
R312 is hydrogen, 1-4C-alkyl, 1-4C-alkoxycarbonyl or 1-4C-alkoxy-2-4C-alkyl,
R313 is hydrogen, 1-4C-alkyl or 1-4C-alkoxy-2-4C-alkyl,
Het1 is optionally substituted by R314 and is a monocylic 3- to 7-membered saturated heterocyclic ring,
which comprises one or two heteroatoms selected from a group consisting of oxygen, nitrogen and sulfur, and
which is bonded to the moiety W via a ring carbon atom or via a ring nitrogen atom, and in which
R314 is 1-4C-alkyl or 1-4C-alkoxycarbonyl,
R32 is 1-4C-alkoxy or halogen, or
R31 and R32 bonded to the phenyl ring in ortho position to each other form together a 1-2C-alkylenedioxy group,
R321 is 1-4C-alkoxy,
V is a bond, Har2 is optionally substituted by R33 and/or R34 and is a monocyclic or fused bicyclic 5- to 10-membered unsaturated or partially saturated heteroaryl radical comprising one to three heteroatoms, each of which is selected from the group consisting of nitrogen, oxygen and sulfur, in which R33 is 1-4C-alkyl, trifluoromethyl, cyano, or —W—R311,
R34 is 1-4C-alkyl, and the salts of these compounds.

Compounds according to embodiment 2 of aspect a of this invention in particular worthy to be mentioned include those compounds of formulae I or, particularly, Ia as defined below, in which R1 is Har1, in which
Har1 is carbazolyl, phenanthridinyl, acridinyl, carbolinyl, phenazinyl, dibenzofuranyl, dibenzothiophenyl, phenothiazinyl, phenoxazinyl, phenoxathiinyl, thianthrenyl, N-methyl-carbazolyl or N-methylcarbolinyl,
R2 is hydrogen, or methyl,
R3 is —U—Ar2, —V—Har2, or 2-amino-phenyl, in which
U is a bond, and
Ar2 is 3-(R31)-phenyl, 4-(R31)-phenyl, or 3-(R31)- or 4-(R31)-fluorophenyl, in which
R31 is amidino, —W—R311, or piperidin-3-yl, in which either
W is a bond,
R311 is —N(R312)R313, in which
R312 is hydrogen, methyl, or 2-methoxyethyl,
R313 is methyl, or
W is methylene, ethylene, or 1,1-dimethyl-methylene,
R311 is —N(R312)R313, in which
R312 is hydrogen, or methyl,
R313 is hydrogen, or
U is methylene, and
Ar2 is 4-(aminomethyl)-phenyl, or
U is aminomethyl-methylene, and
Ar2 is 3,4-dichlorophenyl,
V is a bond,
Har2 is 1,2,3,4-tetrahydroisoquinolinyl, isoindolinyl, or R33-substituted pyridyl, in which
R33 is aminomethyl, and the salts of these compounds.

Compounds according to embodiment 2 of aspect a of this invention in more particular worthy to be mentioned include those compounds of formulae I or, particularly, Ia as defined below, in which R1 is Har1, in which
Har1 is carbazolyl, phenanthridinyl, acridinyl, carbolinyl, phenazinyl, dibenzofuranyl, dibenzothiophenyl, phenothiazinyl, phenoxazinyl, phenoxathiinyl, thianthrenyl, N-methyl-carbazolyl or N-methylcarbolinyl,
R2 is hydrogen,
R3 is —U—Ar2, or —V—Har2, in which
U is a bond,
Ar2 is 3-(R31)-phenyl, 4-(R31)-phenyl, or 2-fluoro-4-(R31)-phenyl, in which
R31 is amidino, or —W—R311, in which
W is methylene, ethylene, or 1,1-dimethyl-methylene,
R311 is —N(R312)R313, in which
R312 is hydrogen, or methyl,
R313 is hydrogen, V is a bond,
Har2 is 1,2,3,4-tetrahydroisoquinolin-7-yl, 1,2,3,4-tetrahydroisoquinolin-6-yl, or R33-substituted pyridyl, in which
R33 is aminomethyl, and the salts of these compounds.

In the context of aspect a, the invention also relates in a further aspect (aspect a1) to compounds according to aspect a, and the salts of these compounds, for use in the treatment or prevention of diseases, such as e.g. those diseases mediated by a dysregulated function of a single protein kinase, with PKB/Akt as an example, or multiple protein kinases within a defined pathway or signalling network.

In the context of aspect a, the invention also relates in a yet further aspect (aspect a2) to the use of compounds according to aspect a and the salts of these compounds, for the manufacture of pharmaceutical compositions for the prevention or treatment of diseases mediated by a dysregulated function of a single protein kinase, with PKB/Akt as an example, or multiple protein kinases within a defined pathway or signalling network.

In the context of aspect a, the invention also relates in a still yet further aspect (aspect a3) to the use of compounds according to aspect a and the salts of these compounds, for the manufacture of pharmaceutical compositions for the prevention or treatment of diseases mediated by a dysregulated function of a single protein kinase, with PKB/Akt as a particular example, or multiple protein kinases within a defined pathway or signalling network, whereby diseases mediated by glycogen synthase kinase 3 are thereof disclaimed.

In this connection, said diseases are in particular hyperproliferative diseases of benign or malignant behaviour, such as, for example, cellular neoplasia, e.g. cancer, and/or disorders responsive to the induction of apoptosis.

The invention further relates in a second aspect (aspect b) to compounds according to aspect a of formula I, and the salts of these compounds, under the provisio that 4-amino-N-[4-(6-pyridin-3-yl-pyrimidin-4-ylamino)-phenyl]-benzamide, 4-amino-N-[4-(6-benzofuran-2-yl-pyrimidin-4-ylamino)-phenyl]-benzamide, 4-amino-N-[4-(6-thiophen-3-yl-pyrimidin-4-ylamino)-phenyl]-benzamide, 4-amino-N-[4-(6-dibenzofuran-1-yl-pyrimidin-4-ylamino)-phenyl]-benzamide, 4-amino-N-[4-(6-benzo[b]thiophen-2-yl-pyrimidin-4-ylamino)-phenyl]-benzamide, 4-amino-N-[4-(6-quinolin-8-yl-pyrimidin-4-ylamino)-phenyl]-benzamide, 4-amino-N-[4-(6-naphthalen-2-yl-pyrimidin-4-ylamino)-phenyl]-benzamide, 4-amino-N-[4-(6-biphenyl-3-yl-pyrimidin-4-ylamino)-phenyl]-benzamide, 4-amino-N-[4-(6-biphenyl-4-yl-pyrimidin-4-ylamino)-phenyl]-benzamide, 4-amino-N-[4-(6-phenyl-pyrimidin-4-ylamino)-phenyl]-benzamide, 4-amino-N-[4-(6-naphthalen-1-yl-pyrimidin-4-ylamino)-phenyl]-benzamide, 4-amino-N-{4-[6-(2-phenoxy-phenyl)-pyrimidin-4-ylamino]-phenyl}-benzamide, 4-amino-N-{4-[6-(2-benzyloxy-phenyl)-pyrimidin-4-ylamino]-phenyl}-benzamide, 4-amino-N-{4-[6-(4-benzyloxy-phenyl)-pyrimidin-4-ylamino]-phenyl}-benzamide, 4-amino-N-{4-[6-(3,4-dimethoxy-phenyl)-pyrimidin-4-ylamino]-phenyl}-benzamide, and 4-amino-N-{4-[6-(2-methoxy-phenyl)-pyrimidin-4-ylamino]-phenyl}-benzamide are thereof disclaimed.

In the context of aspect b, the invention also relates in a further aspect (aspect b1) to compounds according to aspect b, and the salts of these compounds, for use in the treatment or prevention of diseases, such as e.g. those diseases mediated by a dysregulated function of a single protein kinase, with PKB/Akt as an example, or multiple protein kinases within a defined pathway or signalling network.

In the context of aspect b, the invention also relates in a yet further aspect (aspect b2) to the use of compounds according to aspect b, and the salts of these compounds, for the manufacture of pharmaceutical compositions for the prevention or treatment of diseases mediated by a dysregulated function of a single protein kinase, with PKB/Akt as a particular example, or multiple protein kinases within a defined pathway or signalling network, whereby diseases mediated by glycogen synthase kinase 3 are thereof disclaimed.

In this connection, said diseases are in particular hyperproliferative diseases of benign or malignant behaviour, such as, for example, cellular neoplasia, e.g. cancer, and/or disorders responsive to the induction of apoptosis in a mammal.

The invention further relates in a third aspect (aspect c) to compounds of formula I, wherein these compounds are
4-amino-N-[4-(6-pyridin-3-yl-pyrimidin-4-ylamino)-phenyl]-benzamide,
4-amino-N-[4-(6-benzofuran-2-yl-pyrimidin-4-ylamino)-phenyl]-benzamide,
4-amino-N-[4-(6-thiophen-3-yl-pyrimidin-4-ylamino)-phenyl]-benzamide,
4-amino-N-[4-(6-dibenzofuran-1-yl-pyrimidin-4-ylamino)-phenyl]-benzamide,
4-amino-N-[4-(6-benzo[b]thiophen-2-yl-pyrimidin-4-ylamino)-phenyl]-benzamide,
4-amino-N-[4-(6-quinolin-8-yl-pyrimidin-4-ylamino)-phenyl]-benzamide,
4-amino-N-[4-(6-naphthalen-2-yl-pyrimidin-4-ylamino)-phenyl]-benzamide,
4-amino-N-[4-(6-biphenyl-3-yl-pyrimidin-4-ylamino)-phenyl]-benzamide,
4-amino-N-[4-(6-biphenyl-4-yl-pyrimidin-4-ylamino)-phenyl]-benzamide,
4-amino-N-[4-(6-phenyl-pyrimidin-4-ylamino)-phenyl]-benzamide,
4-amino-N-[4-(6-naphthalen-1-yl-pyrimidin-4-ylamino)-phenyl]-benzamide,
4-amino-N-{4-[6-(2-phenoxy-phenyl)-pyrimidin-4-ylamino]-phenyl}-benzamide,
4-amino-N-{4-[6-(2-benzyloxy-phenyl)-pyrimidin-4-ylamino]-phenyl}-benzamide,
4-amino-N-{4-[6-(4-benzyloxy-phenyl)-pyrimidin-4-ylamino]-phenyl}-benzamide,
4-amino-N-{4-[6-(3,4-dimethoxy-phenyl)-pyrimidin-4-ylamino]-phenyl}-benzamide, and
4-amino-N-{4-[6-(2-methoxy-phenyl)-pyrimidin-4-ylamino]-phenyl}-benzamide, and the salts of these compounds.

In the context of aspect c, the invention also relates in a further aspect (aspect c1) to compounds according to aspect c, and the salts of these compounds, for use in the treatment or prevention of diseases, such as e.g. those diseases mediated by a dysregulated function of a single protein kinase, with PKB/Akt as an example, or multiple protein kinases within a defined pathway or signalling network.

In the context of aspect c, the invention also relates in a yet further aspect (aspect c2) to the use of compounds according to aspect c, and the salts of these compounds, for the manufacture of pharmaceutical compositions for the prevention or treatment of diseases mediated by a dysregulated function of a single protein kinase, with PKB/Akt as an example, or multiple protein kinases within a defined pathway or signalling network.

In this connection, said diseases are in particular hyperproliferative diseases of benign or malignant behaviour, such as, for example, cellular neoplasia, e.g. cancer, and/or disorders responsive to the induction of apoptosis in a mammal.

The invention further relates in a fourth aspect (aspect d) to compounds according to aspect a of formula I, under the provisio that R1 is not Har1, Ah1, or Hh1, when the substituent —N(H)C(O)R3 is attached in the meta position with respect to the binding position in which the phenyl ring is bonded to the pyrimidine-amino moiety, and the salts of these compounds.

In the context of aspect d, the invention also relates in a further aspect (aspect d1) to compounds according to aspect d, and the salts of these compounds, for use in the treatment or prevention of diseases, such as e.g. those diseases mediated by a dysregulated function of a single protein kinase, with PKB/Akt as an example, or multiple protein kinases within a defined pathway or signalling network.

In the context of aspect d, the invention also relates in a yet further aspect (aspect d2) to the use of compounds according to aspect d, and the salts of these compounds, for the manufacture of pharmaceutical compositions for the prevention or treatment of diseases mediated by a dysregulated function of a single protein kinase, with PKB/Akt as an example, or multiple protein kinases within a defined pathway or signalling network.

In this connection, said diseases are in particular hyperproliferative diseases of benign or malignant behaviour, such as, for example, cellular neoplasia, e.g. cancer, and/or disorders responsive to the induction of apoptosis in a mammal.

The invention also relates in a fifth aspect (aspect e) to compounds according to aspect a of formula I, in which R1 is Har1, Ah1, or Hh1, and the substituent —N(H)C(O)R3 is attached in the meta position with respect to the binding position in which the phenyl ring is bonded to the pyrimidine-amino moiety, and the salts of these compounds.

In the context of aspect e, the invention also relates in a further aspect (aspect e1) to compounds according to aspect e, and the salts of these compounds, for use in the treatment or prevention of diseases, such as e.g. those diseases mediated by a dysregulated function of a single protein kinase, with PKB/Akt as an example, or multiple protein kinases within a defined pathway or signalling network.

In the context of aspect e, the invention also relates in a yet further aspect (aspect e2) to the use of compounds according to aspect e, and the salts of these compounds, for the manufacture of pharmaceutical compositions for the prevention or treatment of diseases mediated by a dysregulated function of a single protein kinase, with PKB/Akt as a particular example, or multiple protein kinases within a defined pathway or signalling network, whereby diseases mediated by glycogen synthase kinase 3 are thereof disclaimed.

In this connection, said diseases are in particular hyperproliferative diseases of benign or malignant behaviour, such as, for example, cellular neoplasia, e.g. cancer, and/or disorders responsive to the induction of apoptosis in a mammal.

The invention also relates in a sixth aspect (aspect f) to compounds according to aspect a of formula I, under the first provisio that R1 is not Har1, Ah1, or Hh1, when the substituent —N(H)C(O)R3 is attached in the meta position with respect to the binding position in which the phenyl ring is bonded to the pyrimidine-amino moiety, and under the second provisio that 4-amino-N-[4-(6-pyridin-3-yl-pyrimidin-4-ylamino)-phenyl]-benzamide,
4-amino-N-[4-(6-benzofuran-2-yl-pyrimidin-4-ylamino)-phenyl]-benzamide,
4-amino-N-[4-(6-thiophen-3-yl-pyrimidin-4-ylamino)-phenyl]-benzamide,
4-amino-N-[4-(6-dibenzofuran-1-yl-pyrimidin-4-ylamino)-phenyl]-benzamide,
4-amino-N-[4-(6-benzo[b]thiophen-2-yl-pyrimidin-4-ylamino)-phenyl]-benzamide,
4-amino-N-[4-(6-quinolin-8-yl-pyrimidin-4-ylamino)-phenyl]-benzamide,
4-amino-N-[4-(6-naphthalen-2-yl-pyrimidin-4-ylamino)-phenyl]-benzamide,
4-amino-N-[4-(6-biphenyl-3-yl-pyrimidin-4-ylamino)-phenyl]-benzamide,
4-amino-N-[4-(6-biphenyl-4-yl-pyrimidin-4-ylamino)-phenyl]-benzamide,
4-amino-N-[4-(6-phenyl-pyrimidin-4-ylamino)-phenyl]-benzamide,
4-amino-N-[4-(6-naphthalen-1-yl-pyrimidin-4-ylamino)-phenyl]-benzamide,
4-amino-N-{-[6-(2-phenoxy-phenyl)-pyrimidin-4-ylamino]-phenyl}-benzamide,
4-amino-N-{4-[6-(2-benzyloxy-phenyl)-pyrimidin-4-ylamino]-phenyl}-benzamide,
4-amino-N-{4-[6-(4-benzyloxy-phenyl)-pyrimidin-4-ylamino]-phenyl}-benzamide,
4-amino-N-{4-[6-(3,4-dimethoxy-phenyl)-pyrimidin-4-ylamino]-phenyl}-benzamide, and
4-amino-N-{-[6-(2-methoxy-phenyl)-pyrimidin-4-ylamino]-phenyl}-benzamide are thereof disclaimed, and the salts of these compounds.

In the context of aspect f, the invention also relates in a further aspect (aspect f1) to compounds according to aspect f, and the salts of these compounds, for use in the treatment or prevention of diseases, such as e.g. those diseases mediated by a dysregulated function of a single protein kinase, with PKB/Akt as an example, or multiple protein kinases within a defined pathway or signalling network.

In the context of aspect f, the invention also relates in a yet further aspect (aspect f2) to the use of compounds according to aspect f, and the salts of these compounds, for the manufacture of pharmaceutical compositions for the prevention or treatment of diseases mediated by a dysregulated function of a single protein kinase, with PKB/Akt as an example, or multiple protein kinases within a defined pathway or signalling network.

In this connection, said diseases are in particular hyperproliferative diseases of benign or malignant behaviour, such as, for example, cellular neoplasia, e.g. cancer, and/or disorders responsive to the induction of apoptosis in a mammal.

A special interest in the compounds according to this invention refers to those compounds of formula I according to aspect a which are included—within the scope of this invention—by one or, when possible, by more of the following interesting and/or special embodiments:

An interesting embodiment (embodiment a) of the compounds according to aspect a of the present invention refers to those compounds of formula I wherein said compounds are compounds from formula Ia:

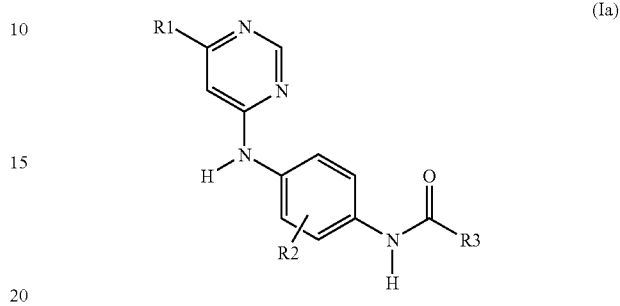

(Ia)

Embodiment a refers to those compounds of formula I, in which the substituent —N(H)C(O)R3 is attached in the para position with respect to the binding position in which the phenyl ring is bonded to the pyrimidine-amino moiety.

Another interesting embodiment (embodiment b) of the compounds according to aspect a of the present invention refers to those compounds of formula I Wherein said compounds are compounds from formula Ib:

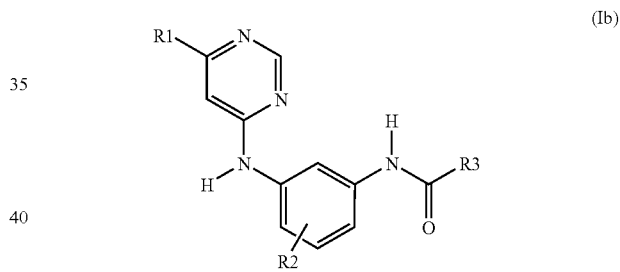

(Ib)

Embodiment b refers to those compounds of formula I, in which the substituent —N(H)C(O)R3 is attached in the meta position with respect to the binding position in which the phenyl ring is bonded to the pyrimidine-amino moiety.

A special embodiment (embodiment 1') of the compounds of formula I according to aspect a of this invention refers to those compounds of formulae I, Ia or Ib, in which the moiety U is a bond.

Another special embodiment (embodiment 2') of the compounds of formula I according to aspect a of this invention refers to those compounds of formulae I, Ia or Ib, in which the moiety U is methylene.

Another special embodiment (embodiment 3') of the compounds of formula I according to aspect a of this invention refers to those compounds of formulae I, Ia or Ib, in which the moiety U is ethylene.

Another special embodiment (embodiment 4') of the compounds of formula I according to aspect a of this invention refers to those compounds of formulae I, Ia or Ib, in which the moiety U is 1-2C-alkylene substituted with amino-1-2C-alkyl, in particular, methylene substituted with amino-1-2C-alkyl, in more particular, methylene substituted with aminomethyl.

Another special embodiment (embodiment 5') of the compounds of formula I according to aspect a of this invention refers to those compounds of formulae I, Ia or Ib, in which R1 is Ar1.

Another special embodiment (embodiment 6') of the compounds of formula I according to aspect a of this invention refers to those compounds of formulae I, Ia or Ib, in which R1 is Aa1.

Another special embodiment (embodiment 7') of the compounds of formula I according to aspect a of this invention refers to those compounds of formulae I, Ia or Ib, in which R1 is Har1.

Another special embodiment (embodiment 8') of the compounds of formula I according to aspect a of this invention refers to those compounds of formula Ib according to embodiment b, in which R1 is Ar1, Aa1 or Ha1, particularly Ar1 or Aa1.

Another special embodiment (embodiment 9') of the compounds of formula I according to aspect a of this invention refers to those compounds of formula Ib according to embodiment b, in which R1 is Har1, Hh1 or Ah1, particularly Har1.

Another special embodiment (embodiment 10') of the compounds of formula I according to aspect a of this invention refers to those compounds of formula Ia according to embodiment a, in which R1 is Ar1, Aa1, Ha1, Har1, Hh1 or Ah1, particularly Ar1, Aa1 or Har1.

Another special embodiment (embodiment 11') of the compounds of formula I according to aspect a of this invention refers to those compounds of formulae I, Ia or Ib, in which R2 is hydrogen.

A special embodiment (embodiment 12') more worthy to be mentioned of the compounds of formula I according to aspect a of this invention includes those compounds of formula Ia according to embodiment a, in which R1 is Ar1.

Another special embodiment (embodiment 13') more worthy to be mentioned of the compounds of formula I according to aspect a of this invention refers to those compounds of formula Ia according to embodiment a, in which R1 is Aa1.

Another special embodiment (embodiment 14') more worthy to be mentioned of the compounds of formula I according to aspect a of this invention refers to those compounds of formula Ia according to embodiment a, in which R1 is Har1.

A more detailed special embodiment (embodiment 15') of the compounds of formula I according to aspect a of this invention refers to those compounds of formulae I, Ia or Ib, in which R1 is phenoxy-phenyl or benzyloxy-phenyl; especially 4-phenoxy-phenyl or, in particular, 4-benzyloxy-phenyl.

Another more detailed special embodiment (embodiment 16') of the compounds of formula I according to aspect a of this invention refers to those compounds of formulae I, Ia or Ib, in which R1 is a fused tricyclic 13- or 14-membered heteroaryl radical comprising one to three heteroatoms selected independently from the group consisting of nitrogen, oxygen and sulfur, and which heteroaryl radical is attached to the pyrimidine moiety via a ring carbon atom, such as, for example, carbazolyl, phenanthridinyl, acridinyl, carbolinyl, phenazinyl, dibenzofuranyl, dibenzothiophenyl, phenothiazinyl, phenoxazinyl, phenoxathiinyl or thianthrenyl; especially, thianthren-1-yl, dibenzothiophen-4-yl or, in particular, dibenzofuran-4-yl.

Another more detailed special embodiment (embodiment 17') of the compounds of formula I according to aspect a of this invention refers to those compounds of formulae I, Ia or Ib, in which R1 is dibenzofuran-4-yl.

Another more detailed special embodiment (embodiment 18') of the compounds of formula I according to aspect a of this invention refers to those compounds of formulae I, Ia or Ib, in which R3 is —U—Ar2, or —V—Har2, in which U is a bond, straight chain 1-4C-alkylene, or straight chain 1-4C-alkylene substituted with amino-1-4C-alkyl, Ar2 is R31- and/or R32-substituted phenyl, in which R31 is halogen, cyano, amidino, —W—R311, or Het1, in which W is a bond or 1-4C-alkylene, R311 is —N(R312)R313, or Het1, in which R312 is hydrogen, 1-4C-alkyl, 1-4C-alkoxycarbonyl, or 1-4C-alkoxy-2-4C-alkyl, R313 is hydrogen, or 1-4C-alkyl, Het1 is optionally substituted by R314 and is a monocylic 3- to 7-membered saturated heterocyclic ring,
which comprises one or two heteroatoms selected from a group consisting of oxygen, nitrogen and sulfur, and
which is bonded to the moiety W via a ring carbon atom or via a ring nitrogen atom, and in which R314 is 1-4C-alkyl or 1-4C-alkoxycarbonyl, R32 is halogen, V is a bond, Har2 is 1,2,3,4-tetrahydroisoquinolin-7-yl, or R33-substituted pyridyl, in which R33 is —W—R311;

or in which, more precisely,

R3 is —U—Ar2, or —V—Har2, in which

U is a bond, straight chain 1-2C-alkylene, or straight chain 1-2C-alkylene substituted with amino-1-2C-alkyl, Ar2 is R31- and/or R32-substituted phenyl, in which R31 is fluorine, chlorine, cyano, amidino, —W—R311, or Het1, in which W is a bond, or 1-4C-alkylene, R311 is —N(R312)R313, in which R312 is hydrogen, 1-2C-alkyl, 1-2C-alkoxy-ethyl, R313 is hydrogen, or 1-2C-alkyl, Het1 is pyrrolidinyl, piperidinyl, morpholinyl, piperazinyl, or N-(1-4C-alkyl)-piperazinyl, especially pyrrolidin-1-yl or piperidin-3-yl, R32 is fluorine or chlorine, V is a bond, Har2 is 1,2,3,4-tetrahydroisoquinolin-7-yl, or R33-substituted pyridyl, in which R33 is —W—R311, in which W is 1-2C-alkylene, R311 is —N(R312)R313, in which R312 is hydrogen, or 1-2C-alkyl, R313 is hydrogen;

or in which, further more precisely,

R3 is —U—Ar2, —V—Har2, or 2-amino-phenyl, in which

U is a bond, and

Ar2 is 3-(R31)-phenyl, 4-(R31)-phenyl, or 3-(R31)- or 4-(R31)-fluorophenyl, in which R31 is amidino, —W—R311, pyrrolidin-1-yl, or piperidin-3-yl, in which W is a bond, methylene, ethylene, or 1,1-dimethyl-methylene, R311 is —N(R312)R313, or (2-methoxyethyl)-amino, in which R312 is hydrogen, or methyl, R313 is hydrogen, or methyl, or
U is methylene, and
Ar2 is 4-(aminomethyl)-phenyl, or
U is aminomethyl-methylene, and
Ar2 is 3,4-dichlorophenyl, and
V is a bond,
Har2 is 1,2,3,4-tetrahydroisoquinolin-7-yl, or R33-substituted pyridyl, in which
R33 is aminomethyl;

or in which, in particular,
R3 is —U—Ar2, —V—Har2, or 2-amino-phenyl, in which U is a bond, and
Ar2 is 3-(R31)-phenyl, 4-(R31)-phenyl, or 3-(R31)- or 4-(R31)-fluorophenyl, in which
R31 is amidino, —W—R311, pyrrolidin-1-yl, or piperidin-3-yl, in which either
W is a bond, and
R311 is —N(R312)R313, or (2-methoxyethyl)-amino, in which
R312 is hydrogen, or methyl,
R313 is methyl,
or, especially,
W is methylene, ethylene, or 1,1-dimethyl-methylene, and
R311 is —N(R312)R313, in which
R312 is hydrogen, or methyl,
R313 is hydrogen, or
U is methylene, and
Ar2 is 4-(aminomethyl)-phenyl, or
U is aminomethyl-methylene, and
Ar2 is 3,4-dichlorophenyl, and
V is a bond,
Har2 is 1,2,3,4-tetrahydroisoquinolin-7-yl, or R33-substituted pyridyl, in which
R33 is aminomethyl;

or in which, in more particular,
R3 is —U—Ar2, or —V—Har2, in which
U is a bond,
Ar2 is 3-(R31)-phenyl, 4-(R31)-phenyl, or 2-fluoro-4-(R31)-phenyl, in which
R31 is amidino, or —W—R311, in which
W is methylene, ethylene, or 1,1-dimethyl-methylene,
R311 is —N(R312)R313, in which
R312 is hydrogen, or methyl,
R313 is hydrogen,
V is a bond,
Har2 is 1,2,3,4-tetrahydroisoquinolin-7-yl, 6-(R33)-pyrid-3-yl, 6-(R33)-pyrid-2-yl, 2-(R33)-pyrid-4-yl, or 4-(R33)-pyrid-2-yl, in which
R33 is aminomethyl.

Respective another more detailed special embodiment of the compounds of formula I according to aspect a of this invention refers to each and every of the embodiments 1' to 10', or, especially, 12' to 18', in each of which R2 is hydrogen.

An in particular detailed special embodiment (embodiment 19') of the compounds of formula I according to aspect a of this invention refers to those compounds of the formulae I, Ia or Ib, which are included from both embodiment 15' and embodiment 18', and in which R2 is hydrogen.

Another in particular detailed special embodiment (embodiment 20') of the compounds of formula I according to aspect a of this invention refers to those compounds of the formulae I, Ia or Ib, which are included from both embodiment 16' and embodiment 18', and in which R2 is hydrogen.

Another in more particular detailed special embodiment (embodiment 21') of the compounds of formula I according to aspect a of this invention refers to those compounds of the formulae I, Ia or Ib, which are included from both embodiment 17' and embodiment 18', and in which R2 is hydrogen.

An embodiment to be emphasized of the compounds of formula I according to aspect a of the present invention is embodiment a. Thus, compounds according to aspect a of this invention, which are from formula Ia, are to be emphasized within the meaning of this invention. Accordingly, within the embodiments 1' to 21', compounds, which are from formula Ia, are to be emphasized.

As it is apparent from the foregoing references, it is to be understood that the abovementioned embodiments of the compounds according to aspect a of the present invention refer not only to aspect a but also to any or all of the aspects b to f.

A particular embodiment of the compounds according to the present invention relates to those compounds of formula Ia as defined herein, in which
R1 is dibenzofuran-4-yl,
R2 is hydrogen,
R3 is —V—Har2, in which
V is a direct bond,
Har2 is pyridyl substituted by aminomethyl, and the salts thereof.

Another particular embodiment of the compounds according to the present invention relates to those compounds of formula Ia as defined herein, in which
R1 is dibenzofuran-4-yl,
R2 is hydrogen,
R3 is —V—Har2, in which
V is a direct bond,
Har2 is 1,2,3,4-tetrahydroisoquinolinyl or isoindolinyl, whereby
Har2 is bound via a ring carbon atom of the benzene ring portion to the moiety V of the group —V—Har2, and the salts thereof.

Another particular embodiment of the compounds according to the present invention relates to those compounds of formula Ia as defined herein, in which
R1 is dibenzofuran-4-yl
R2 is hydrogen,
R3 is —U—Ar2, in which
U is a direct bond,
Ar2 is 3-(aminomethyl)-phenyl, 4-(aminomethyl)-phenyl, 3-amidino-phenyl or 4-amidino-phenyl, and the salts thereof.

The compounds according to the invention can be prepared, for example, as shown in the reaction scheme 1 below and according to the following specified reaction steps, or, particularly, in a manner as described by way of example in the following examples, or analogously or similarly thereto according to preparation procedures or synthesis strategies known to the person skilled in the art.

Compounds of formula I, in which R1, R2 and R3 have the meanings mentioned above, can be obtained as described as follows.

In the first reaction step of the synthesis route shown in scheme 1, compounds of the formula V, in which R2 has the meanings mentioned above and X is —NO$_2$ or —N(H)PG1, in which PG1 is a suitable protective group, such as for example tertbutoxycarbonyl (Boc) or one of those mentioned in "Protective Groups in Organic Synthesis" by T. Greene and P. Wuts (John Wiley & Sons, Inc. 1999, 3$^{rd}$ Ed.) or in "Protecting Groups (Thieme Foundations Organic Chemistry Series N Group" by P. Kocienski (Thieme Medical Publishers, 2000), are reacted in a nucleophilic substitution reaction with 4,6-dichloropyrimidine to give corresponding compounds of formula IV. Said reaction can be carried out in a manner known to the skilled person or as described in the following examples.

Compounds of formula IV are reacted with compounds of formula R1-M, in which R1 has the meanings mentioned above and M is a group or an atom suitable to react with compounds of formula IV via a CC-bond formation reaction to give corresponding compounds of formula III. Said CC-bond formation reaction may be, for example, a Kumada coupling, a Negishi coupling, a Hiyama coupling, a Sonogashira coupling, a Stille reaction or, preferably, a Suzuki coupling reaction. Thus, in the case of a Suzuki coupling reaction, compounds of formula III are boronic acid esters or, in particular, boronic acids, in which M is —B(OH)$_2$.

Suitably, the Suzuki reaction is carried out as it is known to the person of ordinary skill in the art and/or in a manner as it is described below and specified by way of example in the following examples or analogously or similarly thereto.

Reaction scheme 1:

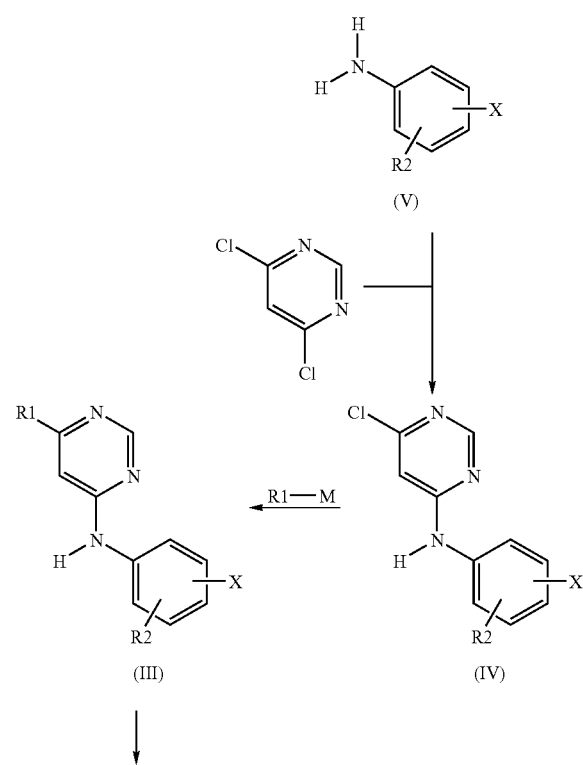

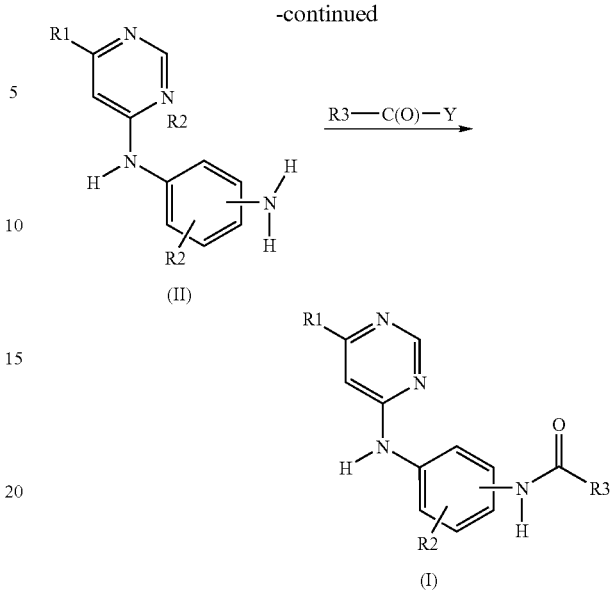

In more detail, the Suzuki reaction mentioned can be carried out in organic solvents alone, for example in toluene, benzene, dimethylformamide or in ethereal (e.g. dimethoxyethane or dioxane) or alcohol solvents or in a mixture thereof, or preferably in a mixture comprising an organic solvent (e.g. dimethoxyethane) and water, with organic (e.g. triethylamine) or preferably inorganic base (e.g. potassium hydroxide, thallium hydroxide, sodium bicarbonate, cesium carbonate, cesium fluoride or, in particular, potassium or sodium carbonate) in the presence of a transition metal catalyst, for example, a nickel or, in particular, palladium catalyst (e.g. Pd(OAc)$_2$, PdCl$_2$(PPh$_3$)$_2$ or Pd(PPh$_3$)$_4$), and, optionally, lithium chloride. The reaction is carried out at a temperature in the range from 20° to 160° C., usually 600 to 130° C. for 10 minutes to 5 days, usually 30 minutes to 24 hours. Advantageously, the solvents used are degassed and the reaction is carried out under protective gas. In the next reaction step, the nitro group of compounds of formula III, in which X is —NO$_2$, is reduced to the amino group of the corresponding compounds of the formula II. Said reduction is carried out in a manner known to the person skilled in the art or as described in the following examples. In more detail, the reduction can be carried out, for example, by catalytic hydrogenation, e.g. in the presence of Raney nickel or a noble metal catalyst such as palladium or, in particular, platinum on active carbon, in a suitable solvent.

Compounds of formula III, in which X is —N(H)PG1, can be also converted to corresponding compounds of formula II. Said conversion can be obtained by deprotection of the protecting group PG1 in a manner habitual per se to the skilled person or as described in the following examples.

Compounds of formula II, in which R1 and R2 have the meanings mentioned above, can be reacted with compounds of formula R3-C(O)—Y, in which Y is a suitable leaving group, preferably a chlorine atom, and R3 stands for the substituents given above, which can be, if necessary, protected by temporary protective groups known to the person skilled in the art (such as e.g. the tertbutoxycarbonyl protective group), to give, after optional removal of said temporary protective groups, compounds of formula I, in which R1, R2 and R3 have the meanings mentioned above.

Alternatively, compounds of formula I, in which R1, R2 and R3 have the meanings mentioned above, can be also obtained from compounds of formula II, in which R1 and R2 have the meanings indicated above, and compounds of formula R3-C(O)—Y, in which Y is hydroxyl and R3 stands for the substituents given above, which can be, if necessary, protected by temporary protective groups known to the person skilled in the art (such as e.g. the tertbutoxycarbonyl protective group), by reaction with amide bond linking reagents known to the person skilled in the art and subsequential optional removal of said temporary protective groups. Exemplary amide bond linking reagents known to the person skilled in the art which may be mentioned are, for example, the carbodiimides (e.g. dicyclohexylcarbodiimide or, preferably, 1-ethyl-3-(3-dimethylaminopropyl)carbodiimide hydrochloride), azodicarboxylic acid derivatives (e.g. diethyl azodicarboxylate), uronium salts [e.g. O-(benzotriazol-1-yl)-N,N,N',N'-tetramethyluronium tetrafluoroborate or O-(benzotriazol-1-yl)-N,N,N',N'-tetramthyl-uronium-hexafluorophosphate] and N,N'-carbonyldiimidazole. In the scope of this invention preferred amide bond linking reagents are uronium salts and, particularly, carbodiimides, preferably, 1-ethyl-3-(3-dimethylaminopropyl)carbodiimide hydrochloride.

Said reaction of compounds of formula I with compounds of formula R3-C(O)—Y can be carried out in an art-known manner or as described in the following examples.

Compounds of formulae V, R1-M or R3-C(O)—Y are known or can be obtained in a known manner or analogously or similarly to art-known compounds, or they are accessible as described in the following examples or analogously or similarly thereto.

Optionally, compounds of the formula I can be also converted into further compounds of the formula I by methods known to one of ordinary skill in the art. More specifically, for example, from compounds of the formula I in which
a) R312 is hydrogen, the corresponding ester compounds can be obtained by esterification reactions;
b) R312 or R313 is hydrogen, the corresponding ether compounds can be obtained by etherification reactions;
c) R312 or R314 is an 1-4C-alkoxycarbonyl group, such as e.g. a tertbutoxycarbonyl group, the corresponding free amino compounds can be obtained by removal of the 1-4C-alkoxycarbonyl group;
d) R31 is a cyano group, the corresponding amidino group can be obtained by imidoester formation and subsequential amination.

The methods mentioned under a), b), c) and d) are expediently carried out analogously to the methods known to the person skilled in the art or as described by way of example in the following examples.

Optionally, compounds of the formula I can be converted into their salts, or, optionally, salts of the compounds of the formula I can be converted into the free compounds.

It is moreover known to the person skilled in the art that if there are a number of reactive centers on a starting or intermediate compound it may be necessary to block one or more reactive centers temporarily by protective groups in order to allow a reaction to proceed specifically at the desired r-action center. A detailed description for the use of a large number of proven protective groups is found, for example, in "Protective Groups in Organic Synthesis" by T. Greene and P. Wuts (John Wiley & Sons, Inc. 1999, 3$^{rd}$ Ed.) or in "Protecting Groups (Thieme Foundations Organic Chemistry Series N Group" by P. Kocienski (Thieme Medical Publishers, 2000).

The substances according to the invention are isolated and purified in a manner known per se, for example by distilling off the solvent under reduced pressure and recrystallizing the residue obtained from a suitable solvent or subjecting it to one of the customary purification methods, such as, for example, column chromatography on a suitable support material.

Salts are obtained by dissolving the free compound in a suitable solvent (e.g. a ketone, such as acetone, methyl ethyl ketone or methyl isobutyl ketone, an ether, such as diethyl ether, tetrahydrofuran or dioxane, a chlorinated hydrocarbon, such as methylene chloride or chloroform, or a low-molecular-weight aliphatic alcohol, such as ethanol or isopropanol) which contains the desired acid or base, or to which the desired acid or base is then added. The salts are obtained by filtering, reprecipitating, precipitating with a nonsolvent for the addition salt or by evaporating the solvent. Salts obtained can be converted into the free compounds, which can in turn be converted into salts, by alkalization or by acidification. In this manner, pharmacologically unacceptable salts can be converted into pharmacologically acceptable salts.

Suitably, the conversions mentioned in this invention can be carried out analogously or similarly to methods which are familiar per se to the person skilled in the art.

The person skilled in the art knows on the basis of his/her knowledge and on the basis of those synthesis routes, which are shown and described within the description of this invention, how to find other possible synthesis routes for compounds of formula I. All these other possible synthesis routes are also part of this invention.

Having described the invention in detail, the scope of the present invention is not limited only to those described characteristics or embodiments. As will be apparent to persons skilled in the art, modifications, analogies, variations, derivations, homologisations and adaptations to the described invention can be made on the base of art-known knowledge and/or, particularly, on the base of the disclosure (e.g. the explicdte, implicite or inherent disclosure) of the present invention without departing from the spirit and scope of this invention as defined by the appended claims.

The following examples serve to illustrate the invention further without restricting it. Likewise, further compounds of formula I, whose preparation is not explicitly described, can be prepared in an analogous or similar manner or in a manner familiar per se to the person skilled in the art using customary process techniques.

Any or all of the compounds of formula I according to the present invention which are mentioned, particularly which are specified as final compounds, in the following examples, as well as the salts or salt-free forms thereof, are a particularly interesting subject of the present invention.

In the examples, mp stands for melting point, h for hour(s), min for minutes, conc. for concentrated, Boc for the tertbutoxycarbonyl group, and other abbreviations have their meanings customary per se to the skilled person.

EXAMPLES

Final Compounds

1. N-[4-(6-Dibenzofuran-4-yl-pyrimidin-4-ylamino)-phenyl]-4-morpholin-4-yl-benzamide 4-Morpholin-4-yl-benzoic acid (228 mg, 1.1 mmol) and 1-hydroxybenzotriazole (148 mg, 1.1 mmol) are dissolved in N,N-dimethylformamide (DMF) (5 mL) and N'-(3-dimethylamino)propyl-N-ethylcarbodiimide hydrochloride (632 mg, 3.3 mmol) and triethylamine (0.46 mL, 3.3 mmol) are added. The mixture is stirred for 1 h at ambient temperature.

N-(6-Dibenzofuran-4-yl-pyrimidin-4-yl)-benzene-1,4-diamine trifluoroacetate (compound A1) (500 mg, 1.1 mmol) is dissolved in DMF (5 mL), further triethylamine (0.15 mL, 1.1 mmol) is added and the above mixture is added at 0° C. The resulting mixture is stirred overnight at room temperature and chloroform (30 mL) is added. The resulting solid is filtered, washed and dried.

Yield: 257 mg (48%)

mp: 335-345° C.

$^1$H-NMR (DMSO-$d_6$): δ/ppm=3.25 (4H, m, N($CH_2$)$_2$); 3.76 (4H, m, O($CH_2$)$_2$); 7.93 (1H, s, $C_5$—H); 8.29 (1H, d, $C_{benzofurane}$—H); 8.31 (1H, d, $C_{benzofurane}$—H); 8.35 (1H, d, $C_{benzofurane}$—H); 8.77 (1H, s, $C_2$—H); 9.87 (1H, s, NH); 9.96 (1H, s, NH).

$^{13}$C-NMR (DMSO-$d_6$): δ/ppm=47.26 (N($\underline{C}H_2$)$_2$); 65.81 (O($CH_2$)$_2$); 105.25 ($C_5$); 152.79 ($C_2$); 155.02 ($C_6$); 156.82 ($C_{benzofurane}$); 157.98 ($C_4$); 160.61 ($C_{benzofurane}$); 164.38 ($\underline{C}O$—NH).

2. N-[4-(6-Dibenzofuran-4-yl-pyrimidin-4-ylamino)-phenyl]-4-dimethylamino-benzamide To a solution of N-(6-dibenzofuran-4-yl-pyrimidin-4-yl)-benzene-1,4-diamine trifluoroacetate (compound A1) (500 mg, 1.1 mmol) in pyridine (10 mL) is added at 10° C. 4-dimethylaminobenzoyl chloride (288 mg, 1.21 mmol) portion wise. After 14 h at ambient temperature the mixture is evaporated and the crude product is purified by crystallization.

Yield: 47% mp: 285-300° C.

$^1$H-NMR (DMSO-$d_6$): δ/ppm=3.01 (6H, m, N($CH_3$)$_2$); 7.97 (1H, s, $C_5$—H); 8.20 (1H, d, $C_{benzofurane}$—H); 8.25 (1H, d, $C_{benzofurane}$—H); 8.40 (1H, d, $C_{benzofurane}$—H); 8.92 (1H, s, $C_2$—H); 10.02 (1H, s, NH); 11.40 (1H, s, NH).

$^{13}$C-NMR (DMSO-$d_6$): δ/ppm=39.71 (N($\underline{C}H_3$)$_2$); 105.65 ($C_5$); 151.89 ($C_2$); 152.43 ($C_6$); 154.29 ($C_{benzofurane}$); 155.09 ($C_4$); 160.79 ($C_{benzofurane}$); 164.73 ($\underline{C}O$—NH).

Unless otherwise noted, the following compounds are prepared analogously to the amide coupling example above (Example 1) starting from compound A1 and the appropriate art-known benzoic acid derivatives.

3. N-[4-(6-Dibenzofuran-4-yl-pyrimidin-4-ylamino)-phenyl]-4-(4-methyl-piperazin-1-ylmethyl)-benzamide mp: 270-274° C.

$^1$H-NMR (DMSO-$d_6$): δ/ppm=2.26 (3H, s, $CH_3$); 2.45 (s); 3.30 (2H, s), 3.56 (2H, s), 7.94 (1H, s, $C_5$—H); 8.25 (1H, d, $C_{benzofurane}$—H); 8.32 (1H, d, $C_{benzofurane}$—H); 8.38 (1H, d, $C_{benzofurane}$—H); 8.78 (1H, s, $C_2$—H); 9.88 (1H, s, NH); 10.20 (1H, s, NH).

$^{13}$C-NMR (DMSO-$d_6$): δ/ppm=45.09 ($\underline{C}H_3$); 51.96, 54.28, 61.30 (N$\underline{C}H_2$); 105.51 ($C_5$); 152.93 ($C_2$); 155.02 ($C_6$); 156.86 ($C_{benzofurane}$); 157.96 ($C_4$); 160.59 ($C_{benzofurane}$); 164.74 ($\underline{C}O$—NH).

4. N-[4-(6-Dibenzofuran-4-yl-pyrimidin-4-ylamino)-phenyl]-2-(4-dimethyl-amino-phenyl)-acetamide mp: >260° C.

$^1$H-NMR (DMSO-$d_6$): δ/ppm=2.86 (6H, s, N($CH_3$)$_2$); 3.49 (2H, s, $CH_2$); 7.88 (1H, s, $C_5$—H); 8.22 (1H, d, $C_{benzofurane}$—H); 8.30 (1H, d, $C_{benzofurane}$—H); 8.36 (1H, d, $C_{benzofurane}$—H); 8.75 (1H, s, C—H); 9.80 (1H, s, NH); 10.01 (1H, s, NH).

$^{13}$C-NMR (DMSO-$d_6$): δ/ppm=40.25 (N($\underline{C}H_3$)$_2$); 42.42 ($\underline{C}H_2$); 105.41 ($C_5$); 152.91 ($C_2$); 154.99 ($C_6$); 156.82 ($C_{benzofurane}$); 157.95 ($C_4$); 160.60 ($C_{benzofurane}$); 169.12 ($\underline{C}O$—NH).

5. N-[4-(6-Dibenzofuran-4-yl-pyrimidin-4-ylamino)-phenyl]-2-dimethylamino-benzamide mp: 246-249° C.

$^1$H-NMR (DMSO-$d_6$): δ/ppm=2.81 (6H, m, N($CH_3$)$_2$); 7.92 (1H, s, $C_5$—H); 8.24 (1H, d, $C_{benzofurane}$—H); 8.36 (1H, d, $C_{benzofurane}$—H); 8.39 (1H, d, $C_{benzofurane}$—H); 8.77 (1H, s, $C_2$—H); 9.86 (1H, s, NH); 11.27 (1 H, s, NH).

$^{13}$C-NMR (DMSO-$d_6$): δ/ppm=43.81 (N($\underline{C}H_3$)$_2$); 105.45 ($C_5$); 152.94 ($C_2$); 155.01 ($C_6$); 156.86 ($C_{benzofurane}$); 157.97 ($C_4$); 160.63 ($C_{benzofurane}$); 165.09 ($\underline{C}O$—NH).

6. N-[4-(6-Dibenzofuran-4-yl-pyrimidin-4-ylamino)-phenyl]-3-pyrrolidin-1-ylbenzamide mp: 250-255° C.

$^1$H-NMR (DMSO-$d_6$): δ/ppm=2.00 (4H, m, ($CH_2$)$_2$); 3.30 (4H, m, N($CH_2$)$_2$); 7.92 (1H, s, $C_5$—H); 8.23 (1H, d, $C_{benzofurane}$—H); 8.32 (1H, d, $C_{benzofurane}$—H); 8.38 (1H, d, $C_{benzofurane}$—H); 8.78 (1H, s, $C_2$—H); 9.86 (1H, s, NH); 10.08 (1H, s, NH).

$^{13}$C-NMR (DMSO-$d_6$): δ/ppm=24.93 (($\underline{C}H_2$)$_2$); 47.31 (N($CH_2$)$_2$); 105.50 ($C_5$); 152.92 ($C_2$); 155.01 ($C_6$); 156.86 ($C_{benzofurane}$); 157.97 ($C_4$); 160.58 ($C_{benzofurane}$); 165.63 ($\underline{C}O$—NH).

7. N-[4-(6-Dibenzofuran-4-yl-pyrimidin-4-ylamino)-phenyl]-benzamide mp: 323-325° C.

$^1$H-NMR (DMSO-$d_6$): δ/ppm=7.92 (1H, s, $C_5$—H); 8.24 (1H, d, $C_{benzofurane}$—H); 8.30 (1H, d, $C_{benzofurane}$—H); 8.37 (1H, d, $C_{benzofurane}$—H); 8.78 (1H, s, $C_2$—H); 9.87 (1H, s, NH); 10.24 (1H, s, NH).

$^{13}$C-NMR (DMSO-$d_6$): δ/ppm=105.51 ($C_5$); 152.93 ($C_2$); 155.02 ($C_6$); 156.88 ($C_{benzofurane}$); 157.96 ($C_4$); 160.58 ($C_{benzofurane}$); 164.89 ($\underline{C}O$—NH).

8. 4-tert-Butyl-N-[4-(6-dibenzofuran-4-yl-pyrimidin-4-ylamino)-phenyl]-benzamide mp: 261-263° C.

$^1$H-NMR (DMSO-$d_6$): δ/ppm=1.34 (9H, s, C($CH_3$)$_3$); 7.92 (1H, s, $C_5$—H); 8.25 (1H, d, $C_{benzofurane}$—H); 8.36 (1H, d, $C_{benzofurane}$—H); 8.38 (1H, d, $C_{benzofurane}$—H); 8.78 (1H, s, $C_2$—H); 9.86 (1H, s, NH); 10.16 (1H, s, NH).

$^{13}$C-NMR (DMSO-$d_6$): δ/ppm=30.92 (C($\underline{C}H_3$)$_3$); 105.51 ($C_5$); 153.95 ($C_2$); 155.02 ($C_6$); 156.86 ($C_{benzofurane}$); 157.97 ($C_4$); 160.59 ($C_{benzofurane}$); 164.84 ($\underline{C}O$—NH).

9. 3,4-Dichloro-N-[4-(6-dibenzofuran-4-yl-pyrimidin-4-ylamino)-phenyl]-benzamide mp: 317-321° C.

$^1$H-NMR (DMSO-$d_6$): δ/ppm=7.93 (1H, s, $C_5$—H); 8.23 (1H, d, $C_{benzofurane}$—H); 8.32 (1H, d, $C_{benzofurane}$—H); 8.38 (1H, d, $C_{benzofurane}$—H); 8.79 (1H, s, $C_2$—H); 9.90 (1H, s, NH); 10.39 (1H, s, NH).

$^{13}$C-NMR (DMSO-$d_6$): δ/ppm=105.63 ($C_5$); 152.94 ($C_2$); 155.02 ($C_6$); 156.92 ($C_{benzofurane}$); 157.96 ($C_4$); 160.55 ($C_{benzofurane}$); 162.48 ($\underline{C}O$—NH).

10. N-[4-(6-Dibenzofuran-4-yl-pyrimidin-4-ylamino)-phenyl]-3-dimethylamino-benzamide To a solution of N-(6-dibenzofuran-4-yl-pyrimidin-4-yl)-benzene-1,4-diamine trifluoroacetic acid (compound A1) (500 mg, 1.1 mmol) in pyridine (10 mL) is added at 10° C. 3-dimethylaminobenzoyl chloride (288 mg, 1.21 mmol) portion wise. After 14 h at ambient temperature the mixture is evaporated and the crude product is purified by crystallization.

Yield: 32% mp: 225-232° C.

$^1$H-NMR (DMSO-d$_6$): δ/ppm=3.01 (6H, s, N(CH$_3$)$_2$); 7.92 (1H, s, C$_5$—H); 8.22 (1H, d, C$_{benzofurane}$—H); 8.38 (1H, d, C$_{benzofurane}$—H); 8.41 (1H, d, C$_{benzofurane}$—H); 8.92 (1H, s, C$_2$—H); 10.27 (1H, s, NH); 10.93 (1H, s, NH).

$^{13}$C-NMR (DMSO-d$_6$): δ/ppm=40.79 (N(CH$_3$)$_2$); 105.64 (C$_5$); 152.55 (C$_2$); 155.08 (C$_6$); 155.28 (C$_{benzofurane}$); 157.97 (C$_4$); 160.79 (C$_{benzofurane}$); 165.47 (CO—NH).

Unless otherwise noted, the following compounds are prepared analogously to the amide coupling example above (Example 1) starting from compound A1 and the appropriate art-known benzoic acid derivatives.

11. N-[4-(6-Dibenzofuran-4-yl-pyrimidin-4-ylamino)-phenyl]-isonicotinamide mp: 283-295° C.

$^1$H-NMR (DMSO-d$_6$): δ/ppm=7.93 (1H, s, C$_5$—H); 8.28 (1H, d, C$_{benzofurane}$,—H); 8.30 (1H, d, C$_{benzofurane}$—H); 8.36 (1H, d, C$_{benzofurane}$—H); 8.78 (1H, s, C$_2$—H); 9.92 (1H, s, NH); 10.50 (1H, s, NH).

$^{13}$C-NMR (DMSO-d$_6$): δ/ppm=105.64 (C$_5$); 152.94 (C$_2$); 155.02 (C$_6$); 156-92 (C$_{benzofurane}$); 157.95 (C$_4$); 160.54 (C$_{benzofurane}$); 163.28 (CO—NH).

12. N-[4-(6-Dibenzofuran-4-yl-pyrimidin-4-ylamino)-phenyl]-4-dimethylaminomethyl-benzamide mp: 299° C.

$^1$H-NMR (DMSO-d$_6$): δ/ppm=2.19 (6H, s, N(CH$_3$)$_2$); 3.49 (2H, s, CH$_2$); 7.93 (1H, s, C$_5$—H); 8.25 (1H, d, C$_{benzofurane}$—H); 8.32 (1H, d, C$_{benzofurane}$—H); 8.38 (1H, d, C$_{benzofurane}$—H); 8.78 (1H, s, C$_2$—H); 9.87 (1H, s, NH); 10.20 (1H, s, NH).

$^{13}$C-NMR (DMSO-d$_6$): δ/ppm=44.87 (N(CH$_3$)$_2$); 62.79 (CH$_2$); 105.52 (C$_5$); 152.93 (C$_2$); 155.02 (C$_6$); 156.87 (C$_{benzofurane}$); 157.97 (C$_4$); 160.59 (C$_{benzofurane}$); 164.73 (CO—NH).

13. N-[4-(6-Dibenzofuran-4-yl-pyrimidin-4-ylamino)-phenyl]-4-morpholin-4-ylmethyl-benzamide mp: >250° C.

$^1$H-NMR (DMSO-d$_6$): δ/ppm=2.37 (4H, d); 3.29 (2H, s); 3.58 (4H, m, OCH$_2$); 7.92 (1H, s, C$_5$—H); 8.23 (1H, d, C$_{benzofurane}$—H); 8.32 (1H, d, C$_{benzofurane}$-1H); 8.78 (1H, s, C$_2$—H); 9.87 (1H, s, NH); 10.20 (1H, s, NH).

$^{13}$C-NMR (DMSO-d$_6$): δ/ppm=53.10; 61.88; 66.08 105.55 (C$_5$); 152.94 (C$_2$); 155.03 (C$_6$); 156.89 (C$_{benzofurane}$); 157.99 (C$_4$); 160.60 (C$_{benzofurane}$); 164.76 (CO—NH).

14. N-[4-(6-Dibenzofuran-4-yl-pyrimidin-4-ylamino)-phenyl]-4-(4-methyl-piperazin-1-yl)-benzamide mp: 304-319° C.

$^1$H-NMR (DMSO-d$_6$): δ/ppm=2.22 (3H, s, CH$_3$); 2.45 (4H, m, CH$_2$); 7.02 (1H, d); 7.88 (1H, s); 8.24 (1H, d, C$_{benzofurane}$—H); 8.31 (1H, d, C$_{benzofurane}$—H); 8.38 (1H, d, C$_{benzofurane}$—H); 8.77 (1H, s, C$_2$—H); 9.85 (1H, s, NH); 9.93 (1H, s, NH).

$^{13}$C-NMR (DMSO-d$_6$): δ/ppm=45.67; 46.90; 54.29; 105.41 (C$_5$); 152.64 (C$_2$); 155.01 (C$_6$); 156.83 (C$_{benzofurane}$); 157.97 (C$_4$); 160.60 (C$_{benzofurane}$); 164.39 (CO—NH).

15. N-[4-(6-Dibenzofuran-4-yl-pyrimidin-4-ylamino)-phenyl]-6-morpholin-4-yl-nicotinamide mp: 310-312° C.

$^1$H-NMR (DMSO-d$_6$): δ/ppm=3.60 (4H, m, N(CH$_2$)$_2$); 3.72 (4H, m, O(CH$_2$)$_2$); 7.93 (1H, s, C$_5$—H); 8.24 (1H, d, C$_{benzofurane}$—H); 8.31 (1H, d, C$_{benzofurane}$—H); 8.36 (1H, d, C$_{benzofurane}$—H); 8.77 (1H, s, C$_2$—H); 9.87 (1H, s, NH); 10.04 (1H, s, NH).

$^{13}$C-NMR (DMSO-d$_6$): δ/ppm=44.65 (N—CH$_2$); 65.76 (O—CH$_2$); 105.35 (C$_5$); 152.92 (C$_2$); 155.02 (C$_6$); 156.84 (C$_{benzofurane}$); 157.97 (C$_4$); 159.69 (C$_{benzofurane}$); 163.37 (CO—NH).

16. N-[4-(6-Dibenzofuran-4-yl-pyrimidin-4-ylamino)-phenyl]-3-[3-methoxy-1-(2-methoxyethyl)-propyl]-benzamide mp: 186-188° C.

17. tert-Butyl N-{4-[4-(6-dibenzofuran-4-yl-pyrimidin-4-ylamino)-phenylcarbamoyl]-benzyl}-carbamate mp: 311-321° C.

18. tert-Butyl N-{2-[4-(6-Dibenzofuran-4-yl-pyrimidin-4-ylamino)-phenylcarbamoyl]-phenyl}-carbamate mp: >340° C.

19. tert-Butyl N{-[4-(6-dibenzofuran-4-yl-pyrimidin-4-ylamino)-phenylcarbamoyl]-phenyl}-carbamate mp: 215-218° C.

20. tert-Butyl 3-{4-[4-(6-Dibenzofuran-4-yl-pyrimidin-4-ylamino)-phenylcarbamoyl]-phenyl}-piperidin-1-carboxylate mp: 259-261° C.

21. tert-Butyl N-(4-{[4-(6-dibenzofuran-4-yl-pyrimidin-4-ylamino)-phenylcarbamoyl]-methyl}-phenyl)-carbamate mp: >320° C.

$^1$H-NMR (DMSO-d$_6$): δ/ppm=1.47 (9H, s, C(CH$_3$)$_3$); 3.56 (2H, s, (CH$_2$)); 7.88 (1H, s, C$_5$—H); 8.22 (1H, d, C$_{benzofurane}$—H); 8.30 (1H, d, C$_{benzofurane}$—H); 8.36 (1H, d, C$_{benzofurane}$—H); 8.75 (1H, s, C$_2$—H); 9.81 (1H, s, NH); 10.07 (1H, s, NH).

$^{13}$C-NMR (DMSO-d$_6$): δ/ppm=28.11 (C(CH$_3$)$_3$); 42.56 (CH$_2$); 78.74 (C(CH$_3$)$_3$); 105.45 (C$_5$); 152.46 (C$_2$); 155.00 (C$_6$); 156.82 (C$_{benzofurane}$); 157.59 (C$_4$); 160.59 (C$_{benzofurane}$); 168.63 (CO—NH).

22. tert-Butyl N-{3-[4-(6-Dibenzofuran-4-yl-pyrimidin-4-ylamino)-phenylcarbamoyl]-benzyl}-carbamate mp: 237° C.

$^1$H-NMR (DMSO-d$_6$): δ/ppm=1.41 (9H, s, C(CH$_3$)$_3$); 4.22 (2H, d, (CH$_2$)); 7.92 (1H, s, C$_5$—H); 8.23 (1H, d, C$_{benzofurane}$—H); 8.30 (1H, d, C$_{benzofurane}$—H); 8.36 (1H, d, C$_{benzofurane}$—H); 8.78 (1H, s, C$_2$—H); 9.87 (1H, s, NH); 10.23 (1H, s, NH).

$^{13}$C-NMR (DMSO-d$_6$): δ/ppm=28.22 (C(CH$_3$)$_3$); 43.23 (CH$_2$); 77.76 (C(CH$_3$)$_3$); 105.54 (C$_5$); 152.93 (C$_2$); 155.01 (C$_6$); 156.88 (C$_{benzofurane}$); 157.97 (C$_4$); 160.60 (C$_{benzofurane}$); 164.96 (CO—NH).

23. tert-Butyl N-(2-{4-[4-(6-Dibenzofurane-4-yl-pyrimidin-4-ylamino)-phenylcarbamoyl]phenyl}-ethyl)-carbamate mp: >250° C.

$^1$H-NMR (DMSO-d$_6$): δ/ppm=1.38 (9H, s, C(CH$_3$)$_3$); 2.77 (2H, t); 3.17 (2H, d, (N—CH$_2$)); 6.90 (1H, t, NH); 7.91 (1H, s, C$_5$—H); 8.23 (1H, d, C$_{Benzofurane}$—H); 8.31 (1H, d, C$_{Benzofurane}$—H); 8.37 (1H, d, C$_{Benzofurane}$—H); 8.78 (1H, s, C$_2$—H); 9.87 (1H, s, NH); 10.16 (1H, s, NH).

$^{13}$C-NMR (DMSO-d$_6$): δ/ppm=28.23 (C(CH$_3$)$_3$); 35.23 (CH$_2$); 41.17 (N—CH$_2$); 77.40 (C(CH$_3$)$_3$); 105.51 (C$_5$); 152.93 (C$_2$); 155.02 (C$_6$); 156.86 (C$_{Benzofurane}$); 157.97 (C$_4$); 160.59 (C$_{Benzofurane}$); 164.70 (CO—NH).

24. tert-Butyl N-{2-[4-(6-Dibenzofuran-4-yl-pyrimidin-4-ylamino)-phenylcarbamoyl]-pyridin-4-ylmethyl}-carbamate mp: 245° C.

$^1$H-NMR (DMSO-d$_6$): δ/ppm=1.41 (9H, s, C(CH$_3$)$_3$); 4.22 (2H, d, (CH$_2$)); 7.92 (1H, s, C$_5$—H); 8.23 (1H, d, C$_{Benzofurane}$—H); 8.30 (1H, d, C$_{Benzofurane}$—H); 8.36 (1H, d, C$_{Benzofurane}$—H); 8.78 (1H, s, C$_2$—H); 9.87 (1H, s, NH); 10.23 (1H, s, NH).

$^{13}$C-NMR (DMSO-d$_6$): δ/ppm=28.22 (C(CH$_3$)$_3$); 43.23 (CH$_2$); 77.76 (C(CH$_3$)$_3$); 105.54 (C$_5$); 152.93 (C$_2$); 155.01 (C$_6$); 156.88 (C$_{Benzofurane}$); 157.97 (C$_4$); 160.60 (C$_{Benzofurane}$); 164.96 (CO—NH).

Unless otherwise noted, the following compounds are prepared analogously to the amide coupling example above (Example 1) starting from compound A2 and the appropriate art-known benzoic acid derivatives.

25. tert-Butyl {4-[3-(6-dibenzofuran-4-yl-pyrimidin-4-ylamino)-phenylcarbamoyl]-benzyl}-carbamate mp: 233-236° C.

26. tert-Butyl N-(2-{4-[3-(6-dibenzofuran-4-yl-pyrimidin-4-ylamino)-phenylcarbamoyl]-phenyl}-ethyl)-carbamate mp: 239-241° C.

27. tert-Butyl N-{2-[3-(6-dibenzofuran-4-yl-pyrimidin-4-ylamino)-phenylcarbamoyl]-phenyl}-carbamate mp: amorpheous 28. tert-Butyl {3-[3-(6-dibenzofuran-4-yl-pyrimidin-4-ylamino)-phenylcarbamoyl]-phenyl}-carbamate mp: 160-163° C.

29. tert-Butyl N-{3-[3-(6-Dibenzofuran-4-yl-pyrimidin-4-ylamino)-phenylcarbamoyl]-benzyl}-carbamate mp: 216-219° C.

30. tert-Butyl N-{4-[3-(6-Dibenzofuran-4-yl-pyrimidin-4-ylamino)-phenylcarbamoyl]-phenyl}-carbamate mp: 214° C.

31. tert-Butyl N-{4-[4-(6-dibenzofuran-4-yl-pyrimidin-4-ylamino)-phenylcarbamoyl]-benzyl}-methylcarbamate The title compound is prepared analogously to the amide coupling example above (Example 1) starting from compound A1 and compound D1.

mp: 225-230° C.

32. tert-Butyl {5-[4-(6-dibenzofuran-4-yl-pyrimidin-4-ylamino)-phenylcarbamoyl]-pyridin-2-ylmethyl}-carbamate The title compound is prepared analogously to the amide coupling example above (Example 1) starting from compound A1 and compound D2.

33. tert-Butyl {4-[4-(6-dibenzofuran-4-yl-pyrimidin-4-ylamino)-phenylcarbamoyl]-pyridin-2-ylmethyl}-carbamate The title compound is prepared analogously to the amide coupling example above (Example 1) starting from compound A1 and compound D3.

34. tert-Butyl (4-{[4-(6-dibenzofuran-4-yl-pyrimidin-4-ylamino)-phenylcarbamoyl]-methyl}-benzyl)-carbamate The title compound is prepared analogously to the amide coupling example above (Example 1) starting from compound A1 and compound D4.

mp: 238-240° C.

35. tert-Butyl N-{4-[3-(6-dibenzofuran-4-yl-pyrimidin-4-ylamino)-4-methyl-phenylcarbamoyl]-benzyl}-carbamate The title compound is prepared analogously to the amide coupling example above (Example 1) starting from compound A3 and the appropriate art-known benzoic acid derivative.

mp: 200-205° C.

36. tert-Butyl N-(1-{4-[4-(6-dibenzofuran-4-yl-pyrimidin-4-ylamino)-phenylcarbamoyl]-phenyl}-1-methyl-ethyl)-carbamate The title compound is prepared analogously to the amide coupling example above (Example 1) starting from compound A1 and compound D5.

37. tert-Butyl N-(2-{3-[4-(6-dibenzofuran-4-yl-pyrimidin-4-ylamino)-phenylcarbamoyl]-phenyl}-ethyl)-carbamate The title compound is prepared analogously to the amide coupling example above (Example 1) starting from compound A1 and compound D6.
mp: 235-238° C.

38. tert-Butyl {-[4-(6-dibenzofuran-4-yl-pyrimidin-4-ylamino)-phenylcarbamoyl]-phenyl}-(2-methoxy-ethyl)carbamate The title compound is prepared analogously to the amide coupling example above (Example 1) starting from compound A1 and compound D7.
mp: 228-231° C. (decomposition)

39. tert-Butyl N-{4-[4-(6-dibenzofuran-4-yl-pyrimidin-4-ylamino)-phenylcarbamoyl]-3-fluorobenzyl}carbamate The title compound is prepared analogously to the amide coupling example above (Example 1) starting from compound A1 and compound D8.
Yield: 163 mg (25%)
mp: 255° C.

40. tert-Butyl {6-[4-(6-dibenzofuran-4-yl-pyrimidin-ylamino)-phenylcarbamoyl]-pyridin-2-ylmethyl}-carbamate The title compound is prepared analogously to the amide coupling example above (Example 1) starting from compound A1 and compound D9.
mp: 195-197° C.

41. tert-Butyl N-{[4-(6-dibenzofuran-4-yl-pyrimidin-4-ylamino)-phenylcarbamoyl]-pyridin-3-ylmethyl}-carbamate The title compound is prepared analogously to the amide coupling example above (Example 1) starting from compound A1 and compound D10.

42. N-[3-(6-Dibenzofuran-4-yl-pyrimidin-4-ylamino)-phenyl]-4-dimethylamino-benzamide To a solution of N-(6-dibenzofuran-4-yl-pyrimidinyl)-benzene-1,3-diamine trifluoroacetate (compound A2) (500 mg, 1.1 mmol) in pyridine (10 mL) is added at 10° C. 4-dimethylaminobenzoyl chloride (222 mg, 1.21 mmol) portion wise. After 2 days at ambient temperature the mixture is evaporated and the crude product is purified by crystallization.
Yield: 33%
mp: >250° C.

43. N-[3-(6-Dibenzofuran-4-yl-pyrimidin-4-ylamino)-phenyl]-4-dimethylaminomethyl-benzamide The title compound is prepared analogously to the amide coupling example above (Example 1) starting from compound A2 and the appropriate art-known benzoic acid derivative.
mp: 240-242° C.

44. 3-Cyano-N-[4-(6-dibenzofuran-4-yl-pyrimidin-4-ylamino)-phenyl]-benzamide The title compound is prepared analogously to the amide coupling example above (Example 1) starting from compound A1 and the appropriate art-known benzoic acid derivative.
mp: 285-290° C.

45. 3-Carbamimidoyl-N-[4-(6-dibenzofuran-4-yl-pyrimidin-4-ylamino)-phenyl]-benzamide 3-Cyano-N-[4-(6-dibenzofuran-4-yl-pyrimidin-4-ylamino)-phenyl]-benzamide (compound 44) (275 mg, 0.57 mmol) dissolved in dioxane (60 mL) and methanol (20 mL) is cooled to 0-5° C. and HCl-gas is added. After 0.5 h the mixture is evaporated, to the residue is added methanol (10 mL) and $(NH_4)_2CO_3$ (0.50 g, 0.52 mmol) and the mixture is stirred for 48 h. After neutralization with aqueous hydrochloric acid/isopropanol the product is purified with silica gel flash chromatography.
Yield: 56 mg
mp: 300-306° C.

46. 4-Cyano-N-[4-(6-dibenzofuran 4-yl-pyrimidin-4-ylamino)-phenyl]-benzamide The title compound is prepared analogously to the amide coupling example above (Example 1) starting from compound A1 and the appropriate art-known benzoic acid derivative.
mp: >250° C.

47. 4-Carbamimidoyl-N-[4-(6-dibenzofuran-4-yl-pyrimidin-4-ylamino)-phenyl]-benzamide The title compound is prepared analogously to the Example 45 starting from compound 46.
mp: 213-219° C.

48. N-[3-(6-Dibenzofuran-4-yl-pyrimidin-4-ylamino)-phenyl]-3-dimethylamino-benzamide To a solution of N-(6-dibenzofuran-4-yl-pyrimidin-4-yl)-benzene-1,3-diamine trifluoroacetate (compound A2) (500 mg, 1.1 mmol) in pyridine (10 mL) is added at 10° C. 3-dimethylaminobenzoyl chloride HCl (288 mg, 1.21 mmol) portion wise. After 48 h at ambient temperature the mixture is evaporated and the crude product is purified by flash chromatography.
Yield: 25%
mp: 245-251° C.

49. 4-Aminomethyl-N-[4-(6-dibenzofuran-4-yl-pyrimidin-4-ylamino)-phenyl]-benzamide trifluoroacetate tert-Butyl N-{4-[4-(6-dibenzofuran-4-yl-pyrimidin-4-ylamino)-phenylcarbamoyl]-benzyl}-carbamate (compound 17) (200 mg, 0.34 mmol) is stirred in a mixture of 0.5 ml trifluoroacetic acid (TFA)/dichloromethane (5 mL) overnight. The resulting solid is filtered, washed and dried. Yield: 40% mp: 155-165° C.

$^1$H-NMR (DMSO-$d_6$): δ/ppm=4.14 (2H, m, C$\underline{H}_2$—NH$_2$); 7.90 (1H, s, C$_5$—H); 8.26 (3H, m, C$_{benzofurane}$—H); 8.32 (2H, bs, CH$_2$—N$\underline{H}_2$); 8.82 (1H, s, C$_2$—H); 10.08 (1H, s, NH); 10.29 (1H, s, NH).

$^{13}$C-NMR (DMSO-$d_6$): δ/ppm=41.89 (CH$_2$—NH$_2$); 105.61 (C$_5$); 152.85 (C$_2$); 155.03 (C$_6$); 155.93 (C$_{benzofurane}$); 157.41 (C$_4$); 160.61 (C$_{benzofurane}$); 164.28 ($\underline{C}$O—NH).

Unless otherwise noted, the following compounds are prepared analogously to Example 49 starting from the appropriate Boc-protected compounds 17 to 41, or A4 to A6.

50. 2-Amino-N-[4-(6-dibenzofuran-4-yl-pyrimidin-4-ylamino)-phenyl]-benzamide trifluoroacetate mp: 136-138° C.

$^1$H-NMR (DMSO-$d_6$): δ/ppm=7.86 (1H, s, C$_5$—H); 8.24 (2H, dd, C$_{benzofurane}$—H); 8.37 (1H, d, C$_{benzofurane}$—H); 8.87 (1H, s, C$_2$—H); 10.09 (1H, s, NH); 10A0 (1H, s, NH).

$^{13}$C-NMR (DMSO-$d_6$): δ/ppm=105.41 (C$_5$); 152.69 (C$_2$); 155.05 (C$_6$); 156.26 (C$_{benzofurane}$); 158.05 (C$_4$); 160.76 (C$_{benzofurane}$); 167.13 ($\underline{C}$O—NH).

51. 3-Amino-N-[4-(6-Dibenzofuran-4-yl-pyrimidin-4-ylamino)-phenyl]-benzamide trifluoroacetate mp: 140-147° C.

$^1$H-NMR (DMSO-$d_6$): δ/ppm=7.86 (1H, s, C$_5$—H); 8.26 (2H, dd, C$_{benzofurane}$—H); 8.35 (1H, d, C$_{benzofurane}$—H); 8.68 (1H, s, C$_2$—H); 10.25 (1H, s, NH); 10.35 (1H, s, NH).

$^{13}$C-NMR (DMSO-$d_6$): δ/ppm=105.52 (C$_5$); 152.73 (C$_2$); 154.30 (C$_6$); 155.05 (C$_{benzofurane}$); 156.50 (C$_4$); 160.72 (C$_{benzofurane}$); 164.99 ($\underline{C}$O—NH).

52. N-[4-(6-Dibenzofuran-4-yl-pyrimidin-4-ylamino)-phenyl]-4-piperidin-3-yl-benzamide trifluoroacetate mp: 140-147° C.

$^1$H-NMR (DMSO-$d_6$): δ/ppm=1.81 (2H, m); 1.92 (2H, m); 3.08 (3H, m); 3.36 (2H, m); 7.89 (1H, s, C$_5$—H); 8.29 (1H, d, C$_{benzofurane}$—H); 8.31 (1H, d, C$_{benzofurane}$—H); 8.36 (1H, d, C$_{benzofurane}$—H); 8.84 (1H, s, C$_2$—H); 10.27 (2H, s, NH).

$^{13}$C-NMR (DMSO-$d_6$): δ/ppm=22.29; 29.35; 43.00; 47.59; 105.56 (CB); 152.80 (C$_2$); 155.05 (C$_6$); 155.20 (C$_{benzofurane}$); 157.02 (C$_4$); 160.67 (C$_{benzofurane}$); 164.60 ($\underline{C}$O—NH).

53. 2-(4-Amino-phenyl)-N-[4-(6-dibenzofuran-4-yl-pyrimidin-4-ylamino)-phenyl]-acetamide trifluoroacetate mp: 125-130° C.

$^1$H-NMR (DMSO-$d_6$): δ/ppm=3.68 (2H, s, CH$_2$); 7.85 (1H, s, C$_5$—H); 8.25 (1H, d, C$_{benzofurane}$—H); 8.29 (1H, d, C$_{benzofurane}$—H); 8.34 (1H, d, C$_{benzofurane}$—H); 8.82 (1H, s, C$_2$—H); 10.22 (2H, s, NH).

$^{13}$C-NMR (DMSO-$d_6$): δ/ppm=42.44 (CH$_2$); 105.51 (C$_5$); 152.73 (C$_2$); 155.05 (C$_6$); 156.59 (C$_{benzofurane}$); 160.70 (C$_{benzofurane}$); 168.26 ($\underline{C}$O—NH).

54. 3-Aminomethyl-N-[4-(6-dibenzofuran-4-yl-pyrimidin-4-ylamino)-phenyl]-benzamide trifluoroacetate mp: 238-240° C.

$^1$H-NMR (DMSO-$d_6$): δ/ppm=4.16 (2H, d, (CH$_2$)); 7.90 (1H, s, C$_5$—H); 8.30 (6H, m, C$_{Benzofurane}$—H); 8.83 (1H, s, C$_2$—H); 10.18 (1H, s, NH); 10.34 (1H, s, NH).

$^{13}$C-NMR (DMSO-$d_6$): δ/ppm (charakteristische Signale)=42.11 (CH$_2$); 105.61 (C$_5$); 152.83 (C$_2$); 155.05 (C$_6$); 155.51 (C$_{Benzofurane}$); 157.70 (C$_4$); 160.66 (C$_{Benzofurane}$); 164.54 ($\underline{C}$O—NH).

55. 4-(2-Amino-ethyl)-N-[4-(6-dibenzofuran-4-yl-pyrimidin-4-ylamino)-phenyl]-benzamide trifluoroacetate mp: 202° C.

$^1$H-NMR (DMSO-$d_6$): δ/ppm=2.94 (2H, m); 3.05 (2H, m, (N—CH$_2$)); 7.90 (1H, s, C$_5$—H); 8.19 (1H, d, C$_{Benzofurane}$—H); 8.35 (1H, d, C$_{Benzofurane}$—H); 8.86 (1H, s, C$_2$—H); 10.28 (1H, s, NH); 10.56 (1H, s, NH).

$^{13}$C-NMR (DMSO-$d_6$): δ/ppm=32.85 (CH$_2$); 39.62 (N—CH$_2$); 105.57 (C$_5$); 152.93 (C$_2$); 153.33; 155.08 (C$_6$); 155.97 (C$_{Benzofurane}$); 157.82 (C$_4$); 160.77 (C$_{Benzofurane}$); 164.65 ($\underline{C}$O—NH).

56. 4-Aminomethyl-pyridin-2-carbonsäure-[4-(6-dibenzofuran-4-yl-pyrimidin-4-ylamino)-phenyl]-amide trifluoroacetate mp: 211° C. (decomposition)

57. 4-Aminomethyl-N-[3-(6-dibenzofuran-4-yl-pyrimidin-4-ylamino)-phenyl]-benzamid trifluoroacetate mp: 114° C.

58. 4-(2-Amino-ethyl)-N-[3-(6-dibenzofuran-4-yl-pyrimidin-4-ylamino)-phenyl]-benzamide trifluoroacetate mp: 87-90° C.

59. 2-Amino-N-[3-(6-dibenzofuran-4-yl-pyrimidin-4-ylamino)-phenyl]-benzamide trifluoroacetate mp: 140-150° C.

60. 3-Amino-N-[3-(6-dibenzofuran-4-yl-pyrimidin-4-ylamino)-phenyl]-benzamide trifluoroacetate mp: 150-153° C.

61. 3-Aminomethyl-N-[3-(6-dibenzofuran-4-yl-pyrimidin-4-ylamino)-phenyl]-benzamide trifluoroacetate mp: 150-156° C.

62. 4-Amino-N-[3-(6-dibenzofuran-4-yl-pyrimidin-4-ylamino)-phenyl]-benzamide trifluoroacetate mp: 185-188° C.

63. N-[4-(6-Dibenzofuran-4-yl-pyrimidin-4-ylamino)-phenyl]-4-methylaminomethyl-benzamide trifluoroacetate mp: 130-140° C.

64. 6-Aminomethyl-N-[4-(6-dibenzofuran-4-yl-pyrimidin-4-ylamino)-phenyl]-nicotinamide trifluoroacetate mp: 145-150° C.

65. 2-Aminomethyl-N-[4-(6-dibenzofuran-4-yl-pyrimidin-4-ylamino)-phenyl]-isonicotinamide trifluoroacetate mp: 248-250° C.

66. 2-(4-Aminomethyl-phenyl)-N-[4-(6-dibenzofuran-4-yl-pyrimidin-4-ylamino)-phenyl]-acetamide trifluoroacetate mp: 251-255° C.

67. 4-Aminomethyl-N-[3-(6-dibenzofuran-4-yl-pyrimidin-4-ylamino)-4-methyl-phenyl]-benzamide trifluoroacetate mp: 180-185° C.

68. 1,2,3,4-Tetrahydro-isochinolin-7-carbonsäure-[4-(6-dibenzofuran-4-yl-pyrimidin-4-ylamino)-phenyl]-amide trifluoroacetate mp: 153-157° C.

69. 4-(1-Amino-1-methyl-ethyl)-N-[4-(6-dibenzofuran-4-yl-pyrimidin-4-ylamino)-phenyl]-benzamide trifluoracetate mp: foam 70. 3-(2-Amino-ethyl)-N-[4-(6-dibenzofuran-4-yl-pyrimidin-ylamino)-phenyl]-benzamide trifluoroacetate mp: 237-239° C.

71. N-[4-(6-Dibenzofuran-4-yl-pyrimidin-4-ylamino)-phenyl]-4-(2-methoxyethylamino)benzamide trifluoroacetate mp: >250° C.

72. 4-Aminomethyl-N-[4-(6-dibenzofuran-4-yl-pyrimidin-4-ylamino)-phenyl]-2-fluorobenzamide mp: >200° C. (decomposition)

73. 6-Aminomethyl-pyridin-2-carbonsäure-[4-(6-dibenzofuran-4-yl-pyrimidin-4-ylamino)-phenyl]-amide mp: 183-186° C.

74. 5-Aminomethyl-N-[4-(6-dibenzofuran-4-yl-pyrimidin-4-ylamino)-phenyl]-nicotinamide mp: 184° C. (decomposition)

75. 3-Amino-N-[4-(6-dibenzofuran-4-yl-pyrimidin-4-ylamino)-phenyl]-2-(3,4-dichloro-phenyl)-propionamide trifluoroacetate mp: 195-205° C.

76. 3-Amino-N-[3-(6-dibenzofuran-4-yl-pyrimidin-4-ylamino)-phenyl]-2-(3,4-dichlorophenyl)-propionamide trifluoroacetat mp: 138-145° C.

Starting from the appropriate starting compounds which are mentioned herein, which are known from the art or which are accessible in an art-known manner, the following examples can be prepared analogously or similarly to the described examples:

77. 5-Aminomethyl-pyridine-2-carboxylic acid [4-(6-dibenzofuran-4-yl-pyrimidin-4-ylamino)-phenyl]-amide trifluoroacetate mp: 164-170° C.

78. 1,2,3,4-Tetrahydro-isoquinoline-6-carboxylic acid [4-(6-dibenzofuran-4-yl-pyrimidin-4-ylamino)-phenyl]-amide trifluoroacetate mp: 146° C.

Starting Compounds

A1. N-(6-Dibenzofuran-4-yl-pyrimidin-4-yl)-benzene-1,4-diamine trifluoroacetate tert-Butyl N-[4-(6-dibenzofuran-4-yl-pyrimidin-4-ylamino)-phenyl]carbamate (compound B1) (5.0 g, 11.1 mmol) is stirred in a mixture of 5 ml trifluoroacetic acid (TFA) and 50 ml dichloromethane at ambient temperature for 6 h. The solid is filtered and washed with dichloromethane.

Yield: 3.8 g (77%)

mp: 215-220° C.

$^1$H-NMR (DMSO-d$_6$): δ/ppm=7.95 (1H, s, C$_5$—H); 8.24 (1H, d, C$_{benzofurane}$—H); 8.31 (1H, d, C$_{benzofurane}$—H); 8.35 (1H, d, C$_{benzofurane}$—H); 8.85 (1H, s, C$_2$—H); 10.43 (2H, s, NH$_2$).

$^{13}$C-NMR (DMSO-d$_6$): δ/ppm=105.17 (C$_5$); 111.53; 114.06; 116.94; 118.44; 119.68; 121.20; 122.76; 122.89; 123.33; 123.47; 124.71; 126.62; 127.49; 127.97; 138.04; 152.81; 154.89; 155.10; 157.92 (q, CF$_3$COOH); 161.02.

A2. N-(6-Dibenzofuran-4-yl-pyrimidin-4-yl)-benzen-1,3-diamine trifluoroacetate

The compound is prepared analogously to the para example above (Example A1).

mp: 142-146° C.

A3. N*3*-(6-Dibenzofuran-4-yl-pyrimidin-4-yl)-4-methyl-benzol-1,3-diamine (6-Dibenzofuran-4-yl-pyrimidin-4-yl)-(2-methyl-5-nitrophenyl)-amine (compound B3) (820 mg, 2.07 mmol) is dissolved in DMF (50 mL), Pt/C (164 mg, 10% Pt) is added and the mixture is hydrogenated for 20 h. After standard workup, the crude product is purified by flash chromatography.

Yield: 422 mg (56%)
mp: 255-257° C.

Unless otherwise noted, the following compounds A4 and A5 are prepared analogously to the amide coupling example above (Example 1) starting from compound A1 and the appropriate art-known benzoic acid derivatives.

A4. tert-Butyl 7-[4-(6-dibenzofuran-4-yl-pyrimidin-4-ylamino)-phenylcarbamoyl]-3,4-dihydro-1H-isochinolin-2-carboxylate mp: 235-238° C.

A5. tert-Butyl N-[2-[4-(6-dibenzofuran-4-yl-pyrimidin-4-ylamino)-phenylcarbamoyl]-2-(3,4-dichlorophenyl)-ethyl]-carbamate mp: 208-214° C.

A6. tert-Butyl N-[2-[3-(6-dibenzofuran-4-yl-pyrimidin-4-ylamino)-phenylcarbamoyl]-2-(3,4-dichlorophenyl)-ethyl]-carbamate The title compound is prepared analogously to the amide coupling example above (Example 1) starting from compound A2 and the appropriate art-known benzoic acid derivative.

mp: 90-95° C.

B1. tert-Butyl N-[4-(6-dibenzofuran-4-yl-pyrimidin-4-ylamino)-phenyl]carbamate tert-Butyl N-[4-(6-chloropyrimidin-4-ylamino)-phenyl]carbamate (compound C1) (10.1 g, 31 mmol) and 4-dibenzofurane boronic acid (9.96 g, 47 mmol) are heated in dimethoxyethane (500 mL) under an inert atmosphere with dichloro-bis(tricyclohexylphosphine)-palladium(II) (2.28 g, 3.1 mmol) and an aqueous $Na_2CO_3$-solution (32.8 g in 310 mL of water) for 4 h at 80° C. After evaporation and extraction of the residue, the product is purified by crystallization.

Yield: 9.5 g (67%)
mp: 222-226° C.
$^1$H-NMR (DMSO-$d_6$): δ/ppm=1.49 (9H, s, $(CH_3)_3$); 7.87 (1H, s, $C_5$—H); 8.24 (1H, d, $C_{benzofurane}$—H); 8.30 (1H, d, $C_{benzofurane}$—H); 8.35 (1H, d, $C_{benzofurane}$—H); 8.73 (1H, s, $C_2$—H); 9.27 (1H, s, NH); 9.73 (1H, s, NH).
$^{13}$C-NMR (DMSO-$d_6$): δ/ppm=28.15 ($C(CH_3)_3$); 78.70 ($C(CH_3)_3$); 105.17 ($C_5$); 111.39; 118.51; 120.71; 120.86; 121.30; 121.59; 122.85; 123.15; 123.29; 124.47; 126.52; 127.71; 133.86; 134.48; 152.56; 152.92; 155.00; 156.72; 157.95; 160.71.

B2. tert-Butyl [3-(6-dibenzofurane-4-yl-pyrimidin-4-ylamino)-phenyl]-arbamate

The compound is prepared analogously to the para example above (Example B1).

mp: 234-250° C.
$^1$H-NMR (DMSO-$d_6$): δ/ppm=1.52 (9H, s; $(C(CH_3)_3)$; 7.17 (2H, m); 8.22 (1H, d, $C_{Benzofurane}$—H); 8.27 (1H, d, $C_{Benzofurane}$—H); 8.45 (1H, d, $C_{Benzofurane}$—H); 8.76 (1H, s); 9.77 (1H, s, NH); 9.82 (1H, s, NH).
$^{13}$C-NMR (DMSO-$d_6$): δ/ppm=27.85 ($C(CH_3)_3$); 78.47 ($C(CH_3)_3$); 105.77 ($C_2$); 152.48; 153.25; 155.28 ($C_{Benzofurane}$); 156.99 ($C_{Benzofurane}$); 157.70; 160.99 ($C_{Benzofurane}$).

B3. (6-Dibenzofuran-4-yl-pyrimidin-4-yl)-(2-methyl-5-nitro-phenyl)-amine

An aqueous $Na_2CO_3$-solution (11.0 g, 104 mmol carbonate in 104 mL of water) is stirred with (6-chloropyrimidin-4-yl)-(2-methyl-5-nitro-phenyl)-amine (compound C3) (2.80 g, 10.6 mmol), 4-dibenzofuranboronic acid (3.36 g, 15.9 mmol) and bistriphenylphosphinpalladiumdichloride (0.74 g, 1.1 mmol) in ethylenglycoledimethylether (168 mL). The mixture is heated to 80° C. After 1 h the mixture is cooled and filtered. The product is purified by flash silica gel chromatography.

Yield: 2.00 g (48%)
mp: 210-213° C.

C1. tert-Butyl N-[4-(6-chloropyrimidin-4-ylamino)-phenyl]carbamate 4,6-Dichloropyrimidine (14.89 g, 0.1 mol), N-Boc-1,4-phenylenediamine (20.83 g, 0.1 mol) and diisopropylethylamine (17.11 mL, 0.1 mol) are heated in n-butanol (160 mL) for 20 h at 90° C. After evaporation, the residue is extracted and purified by crystallization.

Yield: 25.5 g (80%)
mp: 165-166° C.
$^1$H-NMR (DMSO-$d_6$): δ/ppm=1.47 (9H, s, $(CH_3)_3$); 6.89 (1H, s, $C_5$—H); 7A3 (4H, s, Ar); 8.40 (1H, s, $C_2$—H); 9.28 (1H, s, NH); 9.69 (1H, s, NH).
$^{13}$C-NMR (DMSO-$d_6$): δ/ppm=28.11 ($C(CH_3)_3$); 79.01 ($C(CH_3)_3$); 103.93 ($C_5$); 118.44; 121.30; 132.65; 135.22; 152.47; 157.52; 158.14; 161.02.

C2. tert-Butyl [3-(6-chloropyrimidin-4-ylamino)-phenyl]-arbamate

Starting from the appropriate starting compound, the title compound is prepared analogously to the Example C1.

mp: 107-111° C.
$^1$H-NMR (DMSO-$d_6$): δ/ppm=1.48 (9H, s; $(C(CH_3)_3)$; 6.80 (1H, s); 7.11 (1H, d); 7.22 (1H, t); 7.37 (1H, d); 7.68 (1H, s); 8.44 (1H, s); 9.37 (1H, s, NH); 9.81 (1H, s, NH).
$^{13}$C-NMR (DMSO-$d_6$): δ/ppm=28.09 ($C(CH_3)_3$); 78.89 ($C(CH_3)_3$); 104.56 ($C_2$); 110.08 113.23; 114.23; 128.67; 138.80; 139.76; 152.40; 157.63; 158.06; 160.97.

C3. (6-Chloropyrimidin-4-yl)-(2-methyl-5-nitro-phenyl)-amine 4,6-Dichloropyrimidine (5.37 g, 36.0 mmol) and 2-methyl-5-nitroaniline (5.48 g, 36.0 mmol) are heated in n-butanol (58 mL) with diisopropylethylamine (4.66 g, 36 mmol) for 3 days at 110° C. The mixture is evaporated and the product is purified by standard methods.

Yield: 3.1 g (27%)
mp: 128-130° C.

D1. 4-[(tert-Butoxycarbonyl-methyl-amino)-methyl]-benzoic Acid

To 4-methylaminomethyl-benzoic acid (compound E1) (2.55 g, 15.4 mmol) in tetrahydrofurane (THF) (93 mL) are added triethylamine (1.72 g, 17.0 mmol) und Boc-anhydride ($Boc_2O$) (4.04 g, 18.5 mmol). After 1 h at ambient temperature the residue is purified by flash chromatography.

Yield: 1.5 g (37%)
mp: 131-133° C.

D2. 6-(tert-Butoxycarbonylamino-methyl)-nicotinic Acid

To a solution of 6-aminomethyl-nicotinic acid hydrochloride (compound E2) (5.35 g, 28.3 mmol) in aqueous 1N NaOH (60 mL) and tert-butanol (40 mL) is added Boc-anhydride (Boc$_2$O) (6.20 g, 28.4 mmol) and the mixture is stirred overnight. After evaporation of the solvents the product is isolated by standard methods.
Yield: 3.57 g (50%)
mp: 145-147° C.

D3. 2-(tert-Butoxycarbonylamino-methyl)-isonicotinic Acid

Starting from compound E3, the title compound is prepared analogously to the Example D2.
mp: 207° C.

D4. [4-(tert-Butoxycarbonylamino-methyl)-phenyl]-acetic Acid

Starting from the appropriate art-known starting compound, the title compound is prepared analogously to the Example D2.
mp: 89-91° C.

D5. 4-(1-tert-Butoxycarbonylamino-1-methyl-ethyl)-benzoic Acid

Starting from compound E4, the title compound is prepared analogously to the Example D2.
mp: 205-208° C.

D6. 3-(2-tert-Butoxycarbonylamino-ethyl)-benzoic Acid

Ethyl 3-cyanomethyl-benzoate (compound E5) (7.15 g, 41 mmol) is dissolved in ethanol (200 mL) and concentrated hydrochloric acid (5 mL), Pd/C (2 g) is added and the mixture is hydrogenated at 3 bar hydrogen pressure for 24 h. Afterwards, the mixture is filtered, evaporated and the residue is treated with methanol (120 mL) and aqueous 2N NaOH (50 mL, 0.1 mol) and heated 6 h at 40° C., filtered and the filtrate treated with aqueous 2N hydrochloric acid (32 mL, 64 mmol). Boc-anhydride (Boc$_2$O) (9.81 g, 45 mmol) and tert-butanol are added and stirred for 16 h at ambient temperature. The mixture is evaporated, the residue is extracted with dichloromethane/ethyl acetate (1:1, 3×30 mL) and water. After evaporation the organic phase is purified by flash chromatography.
Yield: 1.73 g (16%)
mp: 121-123° C.

D7. 4-[tert-Butoxycarbonyl-(2-methoxyethyl)-amino]-benzoic Acid

To 2-methoxy-ethyl 4-[tert-butoxycarbonyl-(2-methoxyethyl)-amino]-benzoate (compound E6) (1.37 g, 3.9 mmol) in methanol (60 mL) is added aqueous 2N NaOH (30 mL, 60 mmol) and the solution is stirred 16 h at ambient temperature. By using an aqueous 2N hydrochloric acid solution the pH is adjusted to 4, methanol is evaporated and the water phase is extracted with CH$_2$Cl$_2$ (4×15 mL). After drying (MgSO$_4$) and evaporation the crude product is transferred to the next step without any further purification.
Yield: 1.11 g (49%), colorless oil

D8. 4-(tert-Butoxycarbonylamino-methyl)-2-fluorobenzoic Acid

4-Cyano-2-fluorobenzoic acid (1.965 g, 11.9 mmol) is dissolved in ethanol and chloroform, Pd/C (5%, 700 mg) is added and hydrogenated for 6 h. The mixture is filtered and evaporated. The residue is dissolved in aqueous 2N NaOH (12 mL, 24 mmol) and tertbutanol (15 mL) and Boc-anhydride (Boc$_2$O) (2.84 g, 13 mmol) is added. After reaction, the mixture is evaporated and after work up the resulting product is filtered.
Yield 2.27 g (71%)
mp: 125-127° C. (decomposition)

D9. 6-(tert-Butoxycarbonylamino-methyl)-pyridine 2-carboxylic Acid

Starting from compound E7 the title compound is prepared analogously to the Example D2.
mp: 238-240° C.

D10. 5-(tert-Butoxycarbonylamino-methyl)-nicotinic Acid

Starting from compound E8, the title compound is prepared analogously to the Example D2.

E1. 4-Methylaminomethyl-benzoic Acid

4-Bromomethyl-benzoic acid (5 g, 22.8 mmol) is treated with a methylamine solution (40%, 75 mL, 867 mmol) for 4 days at ambient temperature. The resulting mixture is evaporated and the residue purified by flash chromatography.
Yield: 66%
mp: 250-255° C.

E2. 6-Aminomethyl-nicotinic Acid Hydrochloride

6-Cyano-nicotinic acid (1 g, 6.7 mmol) is dissolved in ethanol (100 mL) and chloroform (2 mL) and hydrogenated at 3 bar hydrogen pressure for 5 h using palladium on charcoal as catalyst. After filtration of the catalyst the product is isolated by evaporation of the solvent.
Yield: 0.54 g (43%)

E3. 2-Aminomethyl-isonicotinic Acid Hydrochloride

Starting from the appropriate starting compound, the title compound is prepared analogously to the Example E2.

E4. 4-(1-Amino-1-methyl-ethyl)-benzoic Acid Hydrochloride

Ethyl 4-(1-formylamino-1-methyl-ethyl)-benzoate (2.97 g, 12.6 mmol) is added to a mixture of water (30 mL), dioxane (15 mL) and concentrated hydrochloric acid (3.01 mL, 36.1 mmol) and the mixture is heated to 100° C. for 12 h. The reaction mixture is evaporated and the residue is crystallized from ethanol.
Yield: 2.15 g (79%)
mp: 310-318° C.

E5. Methyl 3-cyanomethyl-benzoate

To methyl 3-bromomethyl-benzoate (25.28 g, 0.11 mol) in acetonitrile (230 mL) is added potassium cyanide (14.3 g, 0.22 mmol) and 18-crown-6 (1.00 g, 2.6 mmol) and the mixture is heated to reflux for 24 h. After filtration, the crude product is transferred to the next step without any further purification.

Yield: 18.5 g (96%)

E6. 2-Methoxyethyl 4-[tert-butoxycarbonyl-(2-methoxyethyl)-amino]-benzoate

To 2-methoxyethyl 4-(2-methoxy-ethylamino)-benzoate (compound F1) (1.93 g, 7.6 mmol) are added Boc-anhydride ($Boc_2O$) (2.28 g, 10.5 mmol) and the mixture is heated to 50° C. for 30 h. After cooling the mixture is chromatographed on silica gel.

Yield: 1.37 g (51%), colorless oil

E7. 6-Aminomethyl-pyridine-2-carboxylic Acid Hydrochloride

6-Cyano-pyridine-2-carboxylic acid (compound F2) (250 mg, 1.6 mmol) is dissolved in ethanol (100 mL), concentrated hydrochloric acid (1 mL) and Pd/C (150 mg) are added and the mixture is hydrogenated at 3 bar hydrogen pressure for 6 h. The catalyst is filtered of and the crude product is transferred to the next step without any purification.

Yield: 255 mg (85%)
mp: 214-221° C.

E8. 5-Aminomethyl-nicotinic Acid

A mixture of 5-carbamoyl-nicotinic acid (compound F3) (5.00 g) and phosphorus oxychloride (50 mL, 0.55 mol) is heated to 100° C. for 5 h. After usual workup the crude product is dissolved in ethanol acidified with hydrochloric acid and hydrogenated with the use of Pd/C (1.00 g, 5% Pd) at 4 bar hydrogen pressure for 16 h. After filtration of the catalyst, the mixture is evaporated, and the residue is treated with ethanol and extracted several times with chloroform.

Yield: 0.21 g (5%)

F1. Methoxyethyl 4-(2-methoxy-ethylamino)-benzoate

To 4-aminobenzoic acid (4.11 g, 30.0 mmol) and 2-chloroethyl-methyl-ether (17.01 g, 180 mmol) in DMF (60 mL) are added potassium carbonate (41.4 g, 0.30 mol) and potassium iodide (1.25 g, 7.5 mmol) and the mixture is heated to reflux for 24 h. After cooling the salt is filtered of and the filtrate is evaporated. The residue is extracted with water (30 mL) and TBME (100 mL), the TBME-phase is dried and evaporated. The resulting oil is purified by chromatography.

Yield: 4.60 g (60%), yellowish oil

F2. 6-Cyano-pyridine 2-carboxylic Acid

6-Carbamoyl-pyridine-2-carboxylic acid (compound G1) (500 mg, 3 mmol) and phosphorus oxychloride ($POCl_3$) (15 mL) are heated to reflux temperature for 2 h. The mixture is worked up in the usual manner and the crude product is further used without any purification.

Yield: 280 mg (63%)
mp: 180-181° C.

F3. 5-Carbamoyl-nicotinic Acid

Monobenzyl pyridine-3,5-dicarboxylate (compound G2) (1.92 g, 7.5 mmol) is heated in aqueous concentrated ammonia solution (40 mL, 25%) to 90° C. for 6 h. After cooling, the solution is evaporated and the residue is used as crude product without further purification.

Yield: 1.46 g
mp: 288° C.

G1. 6-Carbamoyl-pyridine-2-carboxylic Acid

Monobenzyl pyridine-2,6-dicarboxylate (compound H1) (1 g, 3.8 mmol) and aqueous 25-% ammonia solution (40 mL) are heated to 90° C. for 6 h. After cooling the mixture is evaporated and washed with ether.

Yield: 800 mg
mp: 231° C.

G2. Monobenzyl pyridine-3,5-dicarboxylate

A mixture of pyridine-3,5-dicarboxylic acid (10.0 g, 60 mmol), benzyl alcohol (69 mL, 0.67 mol), water (24 mL) and sulfuric acid (3.3 mL) is heated 2 h at reflux temperature. The mixture is added to aqueous saturated $NaHCO_3$-solution (600 mL) and the water-phase is extracted with dichloromethane (4×100 mL). The water phase is adjusted to pH 3.8 and the resulting solid is filtered.

Yield: 1.99 g (13%)

H1. Monobenzyl pyridine-2,6-dicarboxylate

Pyridine 2,6-dicarboxylic acid (16.7 g, 0.1 mol) and benzyl alcohol (115 mL, 1.0 mol) are heated in sulfuric acid (5.5 mL) and water (40 mL) for 2 h at reflux temperature. After cooling the solution is neutralized with aqueous $NaHCO_3$-Lösung (ca. 1 L) and extracted with chloroform. The water phase is acidified and extracted with chloroform (250 mL), the organic phase is dried and evaporated. The residue is treated with diethyl ether and the resulting solid is filtered.

Yield: 1.99 g (8%)
mp: 137-138° C.

Commercial Utility

The compounds according to the present invention have valuable pharmacological properties, which can make them commercially applicable.

Thus, for example, they inhibit protein kinases, in particular one or more isoforms of the protein kinase B (PKB)/Akt, and exhibit cellular activity; and they are expected to be commercially applicable in the therapy of diseases responsive to the inhibition thereof.

Protein kinase means an enzyme with an activity towards the hydroxyl group of tyrosine, serine or threonine residues within a substrate protein. In particular protein kinases catalyse the hydrolysis the γ phosphate of ATP and transfer of this phosphate on the hydroxyl group of tyrosine, serine or threonine residues forming a phosphate ester linkage.

Inhibition of protein kinases and analogous terms means inhibiting the activity and function of one or more protein kinases, in particular protein kinases selected from a group of kinases with pathophysiological importance for cancer treatment. Within this group of kinases, the protein kinase B (PKB)/Akt with the isoforms Akt1 (PKBα), Akt2 (PKB β) and Akt3 (PKB γ) is of particular importance. Inhibition of PKB/Akt activity and analogous terms means either a direct or indirect (pathway dependent) inhibition of the PKB/Akt kinase activity.

Particularly interesting in the meaning of this invention are also those compounds of this invention, which are selective in inhibition of the protein kinase B (PKB)/Akt or one or more isoforms thereof, or a selection of protein kinases most relevant or causative involved in a disease state, in particular in cancer; this means that those compounds exhibit greater inhibition against said protein kinase(s), when compared to the compounds inhibition of the activity of other protein kinases like protein kinase A (PKA).

Cellular activity and analogous terms of a protein kinase inhibitor means any cellular effect related to protein kinase inhibition, in particular dephosphorylation of defined substrate proteins causing, as an example, induction of apoptosis or chemosensitization. Chemosensitization and analogous terms is understood in a broad sense as sensitizing neoplastic cells for apoptotic stimuli in general. These stimuli include, for example, effectors of death receptor and survival pathways as well as cytotoxic/chemotherapeutic and targeted agents and finally also radiation. Induction of apoptosis and analogous terms are used to identify a compound which excecutes programmed cell death in cells contacted with that compound or in combination with other compounds routinely used for therapy. "Apoptosis" is defined by complex biochemical events within the contacted cell, such as the activation of cystein specific proteinases ("caspases") and the fragmentation of chromatin. Induction of apoptosis in cells contacted with the compound might not necessarily coupled with inhibition of cell proliferation. Preferably, the inhibition of proliferation and/or induction of apoptosis are specific to cells with aberrant cell growth.

Further on, the compounds according to the present invention inhibit protein kinase activity in cells and tissues, causing a shift towards dephosphorylated substrate proteins and as functional consequence, for example the induction of apoptosis, cell cycle arrest or sensitization towards chemotherapeutic or target-specific cancer drugs. In a preferred embodiment, specific inhibition of PKB/Akt induces cellular effects as mentioned herein alone or in combination with standard cytotoxic or targeted cancer drugs.

Compounds according to the present invention exhibit anti-proliferative and/or pro-apoptotic and/or chemosensitizing properties. Accordingly the compounds of the present invention are useful for treatment of malignant cells. Therefore the compounds of the present invention are expected for use in the production of an anti-proliferative and/or pro-apoptotic and/or chemosensitizing effect in mammals such as human being.

Thus, the compounds according to the present invention can be commercially applicable for treating, ameliorating or preventing diseases of benign or malignant behaviour as described herein, such as e.g. for inhibiting cellular neoplasia.

A "neoplasia" is defined by cells displaying aberrant cell proliferation and/or survival and/or a block in differentiation. A benign neoplasia is described by hyperproliferation of cells, incapable of forming an aggressive, metastasizing tumor in-vivo. In contrast, a malignant neoplasia is described by cells with multiple cellular and biochemical abnormalities, capable of forming a systemic disease, for example forming tumor metastasis in distant organs.

The compounds according to the present invention can be preferably used for the treatment of malignant neoplasia, also described as cancer, characterized by tumor cells finally metastasizing into distinct organs or tissues. Examples of malignant neoplasia treatable with the compounds according to the present invention include solid and haematological tumors. Solid tumors can be exemplified by tumors of the breast, bladder, bone, brain, central and peripheral nervus system, colon, endocrine glands (e.g. thyroid and adrenal cortex), esophagus, endometrium, germ cells, head and neck, kidney, liver, lung, larynx and hypopharynx, mesothelioma, ovary, pancreas, prostate, rectum, renal, small intestine, soft tissue, testis, stomach, skin, ureter, vagina and vulva. Malignant neoplasia include inherited cancers exemplified by Retinoblastoma and Wilms tumor. In addition, malignant neoplasia include primary tumors in said organs and corresponding secondary tumors in distant organs ("tumor metastases"). Hematological tumors can bee exemplified by aggressive and indolent forms of leukemia and lymphoma, namely non-Hodgkins disease, chronic and acute myeloid leukemia (CML/AML), acute lymphoblastic leukemia (ALL), Hodgkins disease, multiple myeloma and T-cell lymphoma. Also included are myelodysplastic syndrome, plasma cell neoplasia, paraneoplastic syndromes, cancers of unknown primary site as well as AIDS related malignancies.

It is to be noted that a cancer disease as well as a malignant neoplasia does not necessarily require the formation of metastases in distant organs. Certain tumors exert devastating effects on the primary organ itself through their aggressive growth properties. These can lead to the destruction of the tissue and organ structure finally resulting in failure of the assigned organ function.

Neoplastic cell proliferation might also effect normal cell behaviour and organ function. For example the formation of new blood vessels, a process described as neovascularization, is induced by tumors or tumor metastases. The compounds according to this invention will commercially applicable for treatment of pathophysiological relevant processes caused by benign or neoplastic cell proliferation, such as but not limited to neovascularization by unphysiological proliferation of vascular endothelial cells.

Drug resistance is of particular importance for the frequent failure of standard cancer therapeutics. This drug resistance is caused by various cellular and molecular mechanisms. One aspect of drug resistance is caused by constitutive activation of anti-apoptotic survival signals with PKB/Akt as a key signalling kinase. Inhibition of PKB/Akt might lead to a resensitization towards standard chemotherapeutic or target specific cancer therapeutics. As a consequence, the commercial applicability of the compounds according to the present invention is not limited to $1^{st}$ line treatment of cancer patients. In a preferred embodiment of this invention, cancer patients with resistance to cancer chemotherapeutics or target specific anti-cancer drugs are also amenable for treatment with these compounds for e.g. $2^{nd}$ or $3^{rd}$ line treatment cycles. In particular, the compounds according to the present invention might be used in combination with standard chemotherapeutic or targeted drugs to resensitize tumors towards these agents.

In the context of their properties, functions and usabilities mentioned herein, the compounds according to the present invention are expected to be distinguished by valuable and desirable effects related therewith, such as e.g. by low toxicity, superior bioavailability in general (such as e.g. good enteral absorption), superior therapeutic window, absence of significant side effects, and/or further beneficial effects related with their therapeutic and pharmaceutical suitability.

The present invention further includes a method for treating mammals, including humans, which are suffering from one of the abovementioned conditions, illnesses, disorders or diseases. The method is characterized in that a pharmacologically active and therapeutically effective and tolerable amount of one or more of compounds according to the present invention is administered to the subject in need of such treatment.

The present invention further includes a method for treating, preventing or ameliorating diseases responsive to inhibition of protein kinases, in particular PKB/Akt, in a mammal, including human, comprising administering a pharmacologically active and therapeutically effective and tolerable amount of one or more of compounds according to the present invention to said mammal.

The present invention further includes a method for treating (hyper)proliferative diseases of benign or malignant behaviour and/or disorders responsive to induction of apoptosis, such as e.g. cancer, particularly any of those cancer diseases described above, in a mammal, including human, comprising administering a pharmacologically active and therapeutically effective and tolerable amount of one or more of compounds according to the present invention to said mammal.

The present invention further includes a method for inhibiting cellular (hyper)proliferation or arresting aberrant cell growth in a mammal, including human, comprising administering a pharmacologically active and therapeutically effective and tolerable amount of one or more of compounds according to the present invention to said mammal.

The present invention further includes a method for inducing apoptosis in cells of aberrant cell growth in a mammal, including human, comprising administering a pharmacologically active and therapeutically effective and tolerable amount of one or more of compounds according to the present invention to said mammal.

The present invention further includes a method for modulating protein kinase activity, inhibiting cell proliferation and/or inducing apoptosis in vivo in the treatment of diseases which are responsive thereto, such as e.g. any of those diseases mentioned above, in a mammal, including human, comprising administering a pharmacologically active and therapeutically effective and tolerable amount of one or more of compounds according to the present invention to said mammal.

The present invention further includes a method for treating malignant neoplasia, such as e.g. cancer, by sensitising towards chemotherapeutic or target-specific anti-cancer drugs in a mammal, including human, comprising administering a pharmacologically active and therapeutically effective and tolerable amount of one or more of compounds according to the present invention to said mammal.

The present invention further relates to a method for treating benign and/or malignant neoplasia, such as, for example, any of those diseases mentioned herein, such as e.g. cancer, in a mammal, including human, comprising administering a pharmacologically active and therapeutically effective and tolerable amount of one or more of compounds according to the present invention to said mammal.

The present invention further includes a method for sensitizing towards chemotherapeutic or target-specific anti-cancer agents in a mammal, including human, comprising administering a pharmacologically active and therapeutically effective and tolerable amount of one or more of the compounds according to the present invention to said mammal.

The present invention further relates to the use of the compounds according to the present invention for the manufacture of pharmaceutical compositions which can be used in the treatment, prevention or amelioration of diseases responsive to protein kinase inhibitor treatment, in particular PKB/Akt inhibitor treatment, such as e.g. those diseases mentioned herein, in particular cancer.

The present invention further relates to the use of the compounds according to the present invention for the manufacture of pharmaceutical compositions which can be used in the treatment, prevention or amelioration of diseases responsive to arresting of aberrant cell growth and/or inducing of apoptosis, such as e.g. those diseases mentioned herein, in particular cancer.

The present invention further relates to the use of the compounds according to the present invention for the manufacture of pharmaceutical compositions which can be used in the treatment, prevention or amelioration of hyperproliferative diseases of benign or malignant behaviour and/or disorders responsive to the induction of apoptosis in a mammal, such as e.g. those diseases mentioned herein, in particular cancer.

The present invention further relates to the use of the compounds according to the present invention for the manufacture of pharmaceutical compositions which can be used in the treatment of benign and/or malignant neoplasia, such as e.g. cancer.

The present invention further relates to the use of compounds according to the present invention for the manufacture of pharmaceutical compositions which can be used for sensitizing towards chemotherapeutic or target specific anti-cancer agents.

The present invention further relates to the use of compounds according to the present invention for the manufacture of pharmaceutical compositions which can be used for sensitizing towards radiation therapy of those diseases mentioned herein, particularly cancer.

The present invention further relates to the use of the compounds according to the present invention for the manufacture of pharmaceutical compositions, which can be used in the treatment of diseases sensitive to protein kinase inhibitor therapy and different to cellular neoplasia. These non-malignant diseases include, but are not limited to benign prostate hyperplasia, neurofibromatosis, and dermatoses.

The present invention further relates to pharmaceutical compositions comprising one or more of the compounds according to this invention and a pharmaceutically acceptable carrier or diluent.

The present invention further relates to combinations comprising one or more of the compounds according to this invention and pharmaceutically acceptable auxiliaries, excipients or vehicles, e.g. for use in the treatment, prevention or amelioration of (hyper)proliferative diseases of benign or malignant behaviour and/or disorders responsive to the induction of apoptosis in a mammal, such as e.g. cancer.

The present invention further relates to a composition consisting essentially of a therapeutically effective and tolerable amount of one or more compounds according to this invention together with the usual pharmaceutically acceptable vehicles, diluents and/or excipients for use in therapy, e.g. for treating diseases sensitive to inhibition of protein kinases, in particular PKB/Akt.

The present invention further relates to compounds according to this invention for use in therapy, such as, for example, in the treatment, prevention or amelioration of diseases sensitive to inhibition of protein kinases, in particular PKB/Akt, such as e.g. (hyper)proliferative diseases of benign or malignant behaviour and/or disorders responsive to the induction of apoptosis, such as e.g. those diseases mentioned herein, particularly cancer.

The present invention further relates to compounds according to the present invention for use in therapy, in particular in the therapy of those diseases mentioned herein.

The present invention further relates to compounds according to this invention having protein kinases inhibiting properties, in particular PKB/Akt inhibiting properties.

The present invention further relates to compounds according to this invention having anti-proliferative and/or apoptosis inducing activity.

Additionally, the invention relates to an article of manufacture, which comprises packaging material and a pharmaceutical agent contained within said packaging material, wherein the pharmaceutical agent is therapeutically effective for inhibiting the effects of protein kinases, in particular inhibition the protein kinase B/Akt, ameliorating the symptoms of a protein kinase mediated disorder, and wherein the packaging material comprises a label or package insert which indicates that the pharmaceutical agent is useful for preventing or treating protein kinase mediated disorders, and wherein said pharmaceutical agent comprises one or more compounds according to the invention. The packaging material, label and package insert otherwise parallel or resemble what is generally regarded as standard packaging material, labels and package inserts for pharmaceuticals having related utilities.

The pharmaceutical compositions according to this invention are prepared by processes which are known per se and familiar to the person skilled in the art. As pharmaceutical compositions, the compounds of the invention (=active compounds) are either employed as such, or preferably in combination with suitable pharmaceutical auxiliaries and/or excipients, e.g. in the form of tablets, coated tablets, capsules, caplets, suppositories, patches (e.g. as TTS), emulsions, suspensions, gels or solutions, the active compound content advantageously being between 0.1 and 95% and where, by the appropriate choice of the auxiliaries and/or excipients, a pharmaceutical administration form (e.g. a delayed release form or an enteric form) exactly suited to the active compound and/or to the desired onset of action can be achieved.

The person skilled in the art is familiar with auxiliaries, vehicles, excipients, diluents, carriers or adjuvants which are suitable for the desired pharmaceutical formulations, preparations or compositions on account of his/her expert knowledge. In addition to solvents, gel formers, ointment bases and other active compound excipients, for example antioxidants, dispersants, emulsifiers, pre-servatives, solubilizers, colorants, complexing agents or permeation promoters, can be used.

Depending upon the particular disease, to be treated or prevented, additional therapeutic active agents, which are normally administered to treat or prevent that disease, may optionally be coadministered with the compounds according to this invention. As used herein, additional therapeutic agents that are normally administered to treat or prevent a particular disease are known as appropriate for the disease being treated.

For example, the compounds according to this invention may be combined with one or more standard therapeutic agents used for treatment of the diseases as mentioned before.

In one particular embodiment, the compounds according to the present invention may be combined with one or more art-known anti-cancer agents, such as e.g. with one or more chemotherapeutic and/or target specific anti-cancer agents.

Examples of known chemotherapeutic anti-cancer agents used in cancer therapy include, but not are limited to (i) alkylating/carbamylating agents such as Cyclophosphamid (Endoxan®), Ifosfamid (Holoxan®), Thiotepa (Thiothepa Lederle®), Melphalan (Alkeran®), or chloroethylnitrosourea (BCNU); (ii) platinum derivatives like cis-platin (Platinex® BMS), oxaliplatin or carboplatin (Carboplat® BMS); (iii) antimitotic agents/tubulin inhibitors such as vinca alkaloids (vincristine, vinblastine, vinorelbine, vinflunine), taxanes such as Taxol (Paclitaxel®), Taxotere (Docetaxel®) and analogs as well as new formulations and conjugates thereof, epothilones such as Epothilone B (Patupilone®), Azaepothilone (Ixabepilone®) or ZK-EPO, a fully synthetic epothilone B analog; (iv) topoisomerase inhibitors such as anthracyclines such as Doxorubicin (Adriblastin®), epipodophyllotoxines such as Etoposide (Etopophos®) and camptothecin analogs such as Topotecan (Hycamtin®); (v) pyrimidine antagonists such as 5-fluorouracil (5-FU), Capecitabine (Xeloda®), Arabinosylcytosine/Cytarabin (Alexan®) or Gemcitabine (Gemzar®); (vi) purin antagonists such as 6-mercaptopurine (Puri-Nethol®), 6-thioguanine or fludarabine (Fludara®) and finally (vii) folic acid antagonists such as methotrexate (Farmitrexat®) and pemetrexed (Alimta®).

Examples of target specific anti-cancer drug classes used in experimental or standard cancer therapy include but are not limited to (i) kinase inhibitors such as e.g. Glivec (Imatinib®), ZD-1839/Iressa (Gefitinib®), Bay43-9006 (Sorafenib®), SU11248 (Sutent®) or OSI-774/Tarceva (Eriotinib®); (ii) proteasome inhibitors such as PS-341 (Velcade®); (iii) heat shock protein 90 inhibitors like 17-allylaminogeldanamycin (17-AAG); (iv) vascular targeting agents (VTAs) like Cobretastatin A4 phosphate or AVE8062/AC7700 and anti-angiogenic drugs like the VEGF antibody Avastin (Bevacizumab®) or the KDR tyrosin kinase inhibitor PTK787/ZK222584 (Vatalanib®); (v) monoclonal antibodies such as Herceptin (Trastuzumab®), MabThera/Rituxan (Rituximab®), C225/Erbitux (Cetuximab®) or Avastin (see above) as well as mutants as well as conjugates of monoclonal antibodies and antibody fragments; (vi) oligonucleotide based therapeutics like G-3139/Genasense (Oblimersen®); (vii) protease inhibitors; (viii) hornonal therapeutics such as anti-estrogens (e.g. Tamoxifen), anti-androgens (e.g. Flutamide or Casodex), LHRH analogs (e.g. Leuprolide, Goserelin or Triptorelin) and aromatase inhibitors; (ix) Toll-like receptor 9 (TLR9) agonists like Promune® and (x) inhibitors of class I/II histone deacetylases (HDACs), namely SAHA, NVP-LBH589, Depsipeptide/FK228 or MS275.

Other known target specific anti-cancer agents which can be used for combination therapy include bleomycin, retinoids such as all-trans retinoic acid (ATRA), DNA methyltransferase inhibitors such as the 2-deoxycytidine derivative Decitabine (Docagen®), alanosine, cytokines such as interleukin-2 or interferons such as interferon α2 or interferon-γ, TRAIL, DR4/5 agonistic antibodies, FasL and TNF-R agonists.

As exemplary anti-cancer agents for use in the combination therapy according to the present invention the following drugs may be mentioned, without being restricted thereto, 5 FU, actinomycin D, ABARELIX, ABCIXIMAB, ACLARUBICIN, ADAPALENE, ALEMTUZUMAB, ALTRETAMINE, AMINOGLUTETHIMIDE, AMIPRILOSE, AMRUBICIN, ANASTROZOLE, ANCITABINE, ARTEMISININ, AZATHIOPRINE, BASILIXIMAB, BENDAMUSTINE, BEXXAR, BICALUTAMIDE, BLEOMYCIN, BROXURIDINE, BUSULFAN, CAPECITABINE, CARBOPLATIN, CARBOQUONE, CARMUSTINE, CETRORELIX, CHLORAMBUCIL, CHLORMETHINE, CISPLATIN, CLADRIBISNE, CLOMIFENE, CYCLOPHOSPHAMIDE, DACARBAZINE, DACLIZUMAB, DACTINOMYCIN, DAUNORUBICIN, DESLORELIN, DEXRAZOXANE, DOCETAXEL, DOXIFLURIDINE, DOXORUBICIN, DROLOXIFENE, DROSTANOLONE, EDELFOSINE, EFLORNITHINE, EMITEFUR, EPIRUBICIN, EPITIOSTANOL, EPTAPLATIN, ERBITUX, ESTRAMUSTINE, ETOPOSIDE, EXEMESTANE, FADROZOLE, FINASTERIDE, FLOXURIDINE, FLUCYTOSINE, FLUDARABINE, FLUOROURACIL, FLUTAMIDE, FORMESTANE, FOSCARNET, FOSFESTROL, FOTEMUSTINE, FULVESTRANT, GEFITINIB, GEMCITABINE, GLIVEC, GOSERELIN, GUSPERIMUS, HER- CEPTIN, IDARUBICIN, IDOXURIDINE, IFOSFAMIDE, IMATINIB, IMPROSULFAN, INFLIXIMAB, IRINOTECAN, LANREOTIDE, LETROZOLE, LEUPRORELIN, LOBAPLATIN, LOMUSTINE, MELPHALAN, MERCAPTOPURINE, METHOTREXATE, METUREDEPA, MIBOPLATIN, MIFEPRISTONE, MILTEFOSINE, MIRIMOSTIM, MITOGUAZONE, MITOLACTOL, MITOMYCIN, MITOXANTRONE, MIZORIBINE, MOTEXAFIN, NARTOGRASTIM, NEBAZUMAB, NEDAPLATIN, NILUTAMIDE, NIMUSTINE, OCTREOTIDE, ORMELOXIFENE, OXALIPLATIN, PACLITAXEL, PALIVIZUMAB, PEGASPARGASE, PEGFILGRASTIM, PENTETREOTIDE, PENTOSTATIN, PERFOSFAMIDE, PIPOSULFAN, PIRARUBICIN, PLICAMYCIN, PREDNIMUSTINE, PROCARBAZINE, PROPAGERMANIUM, PROSPIDIUM CHLORIDE, RALTITREXED, RANIMUSTINE, RANPIRNASE, RASBURICASE, RAZOXANE, RITUXIMAB, RIFAMPICIN, RITROSULFAN, ROMURTIDE, RUBOXISTAURIN, SARGRAMOSTIM, SATRAPLATIN, SIROLIMUS, SOBUZOXANE, SPIROMUSTINE, STREPTOZOCIN, TAMOXIFEN, TASONERMIN, TEGAFUR, TEMOPORFIN, TEMOZOLOMIDE, TENIPOSIDE, TESTOLACTONE, THIOTEPA, THYMALFASIN, TIAMIPRINE, TOPOTECAN, TOREMIFENE, TRASTUZUMAB, TREOSULFAN, TRIAZIQUONE, TRIMETREXATE, TRIPTORELIN, TROFOSFAMIDE, UREDEPA, VALRUBICIN, VERTEPORFIN, VINBLASTINE, VINCRISTINE, VINDESINE, VINORELBINE, VOROZOLE and ZEVALIN.

The person skilled in the art is aware on the base of his/her expert knowledge of the total daily dosage(s) and administration form(s) of the additional therapeutic agent(s) coadministered. Said total daily dosage(s) can vary within a wide range.

In practicing the present invention, the compounds according to this invention may be administered in combination therapy separately, sequentially, simultaneously or chronologically staggered (such as e.g. as combined unit dosage forms, as separate unit dosage forms, as adjacent discrete unit dosage forms, as fixed or non-fixed combinations, as kit-of-parts or as admixtures) with one or more standard therapeutics, in particular art-known anti-cancer agents, such as e.g. those mentioned above (e.g. chemotherapeutic and/or target specific anti-cancer agents).

In this context, the present invention further relates to a combination comprising a first active ingredient, which is at least one compound according to this invention, and a second active ingredient, which is at least one standard therapeutic, in particular at least one an art-known anti-cancer agent, such as e.g. one or more of those mentioned herein above, for separate, sequential, simultaneous or chronologically staggered use in therapy, such as e.g. to treat, prevent or ameliorate diseases responsive to protein kinase inhibitor treatment, in particular responsive to PKB/Akt inhibitor treatment, such as, for example, hyperproliferative diseases of benign or malignant behaviour and/or disorders responsive to the induction of apoptosis in a mammal, such as e.g. those diseases mentioned herein, in particular cancer.

The term "combination" according to this invention may be present as a fixed combination, a non-fixed combination or a kit-of-parts.

A "fixed combination" is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A "kit-of-parts" is defined as a combination wherein the said first active ingredient and the said second active ingredient are present in more than one unit. One example of a "kit-of-parts" is a combination wherein the said first active ingredient and the said second active ingredient are present separately. The components of the kit-of-parts may be administered separately, sequentially, simultaneously or chronologically staggered.

The present invention further relates to a pharmaceutical composition comprising a first active ingredient, which is at least one compound according to this invention, and a second active ingredient, which is at least one standard therapeutic agent, in particular an art-known anti-cancer agent, such as e.g. one or more of those mentioned herein above, and, optionally, a pharmaceutically acceptable carrier or diluent, for separate, sequential, simultaneous or chronologically staggered use in therapy.

The present invention further relates to a kit-of-parts comprising a preparation of a first active ingredient, which is a compound according to this invention, and a pharmaceutically acceptable carrier or diluent; a preparation of a second active ingredient, which is an standard therapeutic agent, in particular an art-known anti-cancer agent, such as one of those mentioned above, and a pharmaceutically acceptable carrier or diluent; for simultaneous, sequential, separate or chronologically staggered use in therapy. Optionally, said kit comprises instructions for its use in therapy, e.g. to treat benign and/or malignant neoplasia responsive to the inhibition of protein kinases, in particular the protein kinase B (PKB)/Akt.

The present invention further relates to a combined preparation comprising at least one compound according to the present invention and at least one known therapeutic agent, in particular at least one art-known anti-cancer agent for simultaneous, sequential or separate administration.

In addition, the present invention further relates to a method for treating diseases and/or disorders responsive to the inhibition of protein kinases, in particular the protein kinase B (PKB)/Akt, such as e.g. cancer, in a patient comprising administering in combination therapy separately, simultaneously, sequentially or chronologically staggered a pharmaceutically active and therapeutically effective and tolerable amount of a pharmaceutical composition, which comprises a compound according to this invention and a pharmaceutically acceptable carrier or diluent, and a pharmaceutically active and therapeutically effective and tolerable amount of one or more standard therapeutic agents, in particular one or more art-known anti-cancer agents, such as e.g. one or more of those mentioned herein, to said patient in need thereof.

In further addition, the present invention relates to a method for treating, preventing or ameliorating (hyper)proliferative diseases and/or disorders responsive to induction of apoptosis, such as e.g. benign or malignant neoplasia, particularly any of those cancer diseases mentioned herein, in a patient comprising administering a combination according to the present invention.

The present invention further relates to a commercial package comprising one or more compounds of the present invention together with instructions for simultaneous, sequential or separate use with one or more standard therapeutics, such as e.g. one or more chemotherapeutic and/or target specific anti-cancer agents, such as e.g. any of those mentioned herein.

The present invention further relates to a commercial package consisting essentially of one or more compounds of the present invention as sole active ingredient together with instructions for simultaneous, sequential or separate use with one or more standard therapeutics, such as e.g. art-known anti-cancer agents, such as e.g. any of those mentioned herein.

The present invention further relates to a commercial package comprising one or more art-known anti-cancer agents, such as e.g. any of those mentioned herein, together with instructions for simultaneous, sequential or separate use with one or more compounds according to the present invention.

The compositions, combinations, preparations, formulations, kits or packages mentioned in the context of the combination therapy according to this invention may also include more than one of the compounds according to this invention and/or more than one of the standard therapeutics, such as e.g. the art-known anti-cancer agents mentioned.

Additionally, the present invention further relates to pharmaceutical combinations or compositions according to this invention having protect kinase inhibiting, in particular PKB/Akt inhibiting, properties.

The present invention further relates to pharmaceutical combinations or compositions according to this invention having anti-(hyper)proliferative and/or apoptosis inducing activity.

The present invention further relates to a method for treating diseases and/or disorders responsive to the inhibition of protein kinases, such as e.g. cancer, in a patient comprising administering a combination, composition, formulation, preparation or kit as described herein to said patient in need thereof.

The present invention further relates to the use of a composition, combination, formulation, preparation or kit in the manufacture of a pharmaceutical product, such as e.g. a commercial package or a medicament, for treating, preventing or ameliorating diseases and/or disorders responsive to the inhibition of protein kinases, in particular the protein kinase B (PKB)/Akt, such as e.g. those diseases mentioned herein, in particular cancer.

The present invention further relates to the use of one or more of the compounds according to this invention for the manufacture of a medicament for use in combination with a chemotherapeutic or target-specific agent for the treatment of cancer, particularly for the treatment of one of those cancer diseases mentioned above, such as e.g. any of those anti-cancer agents mentioned herein.

The first and second active ingredient of a combination or kit-of-parts according to this invention may be provided as separate formulations (i.e. independently of one another), which are subsequently brought together for simultaneous, sequential, separate or chronologically staggered use in combination therapy; or packaged and presented together as separate components of a combination pack for simultaneous, sequential, separate or chronologically staggered use in combination therapy.

The type of pharmaceutical formulation of the first and second active ingredient of a combination or kit-of-parts according to this invention can be similar, i.e. both ingredients are formulated in separate tablets or capsules, or can be different, i.e. suited for different administration forms, such as e.g. one active ingredient is formulated as tablet or capsule and the other is formulated for e.g. intravenous administration.

The amounts of the first and second active ingredients of the combinations, compositions or kits according to this invention may together comprise a therapeutically effective amount for the treatment, prophylaxis or amelioration of a treatment, prophylaxis or amelioration of a (hyper)proliferative disease, particularly one of those diseases mentioned herein.

In addition, compounds according to the present invention can be used in the pre- or post-surgical treatment of cancer.

In further addition, compounds of the present invention can be used in combination with radiation therapy, in particular in sensitisation of cancer patients towards standard radiation therapy.

A combination according to this invention can refer to a composition comprising both the compound according to this invention and the other active anti-cancer agent in a fixed combination (fixed unit dosage form), or a medicament pack comprising the two active ingredients as discrete separate dosage forms (non-fixed combination). In case of a medicament pack comprising the two active ingredients, the active ingredients are preferably packed into blister cards which are suited for improving compliance.

Each blister card preferably contains the medicaments to be taken on one day of treatment. If the medicaments are to be taken at different times of day, the medicaments can be disposed in different sections on the blister card according to the different ranges of times of day at which the medicaments are to be taken (for example morning and evening or morning, midday and evening). The blister cavities for the medicaments to be taken together at a particular time of day are accommodated in the respective range of times of day. The various times of day are, of course, also put on the blister in a clearly visible way. It is also possible, of course, for example to indicate a period in which the medicaments are to be taken, for example stating the times.

The daily sections may represent one line of the blister card, and the times of day are then identified in chronological sequence in this column.

Medicaments which must be taken together at a particular time of day are placed together at the appropriate time on the blister card, preferably a narrow distance apart, allowing them to be pushed out of the blister easily, and having the effect that removal of the dosage form from the blister is not forgotten.

The administration of the pharmaceutical compositions or combinations according to the invention may be performed in any of the generally accepted modes of administration available in the art. Illustrative examples of suitable modes of administration include intravenous, oral, nasal, parenteral, topical, transdermal and rectal delivery. Oral and intravenous delivery are preferred.

For the treatment of dermatoses, the compounds of the invention are in particular administered in the form of those pharmaceutical compositions which are suitable for topical application. For the production of the pharmaceutical compositions, the compounds of the invention (=active compounds) are preferably mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, pastes, gels or solutions.

The pharmaceutical compositions according to the invention are prepared by processes known per se. The dosage of the active compounds is carried out in the order of magnitude customary for protein kinase inhibitors. Topical application forms (such as ointments) for the treatment of dermatoses thus contain the active compounds in a concentration of, for example, 0.1-99%. The customary dose in the case of systemic therapy (p.o.) is between 0.3 and 30 mg/kg per day, (i. v.) is between 0.3 and 30 mg/kg/h.

The choice of the optimal dosage regime and duration of medication, particularly the optimal dose and manner of administration of the active compounds necessary in each case can be determined by a person skilled in the art on the basis of his/her expert knowledge.

Biological Investigations

Expression and purification of ΔPHAkt1, Akt1 (active). Akt1 (inactive), PDK1, and PKA:

For the biochemical assay ΔPHAkt1 was used devoid of its PH domain as a GST fusion protein (named GST-deltaPH-Akt1; 107480aa; cloned in the pAcG1 vector (BD Biosciences Pharmingen)), co-expressed with PDK1 in SF9 insect cells. The protein was purified using glutathion-affinity chromatography by standard protocols.

For the biochemical Akt1 assay recombinant full-length human Akt1, containing N-terminal His6 tag was cloned and expressed in baculovirus infected Sf21 insect cells. Akt1 is activated with GST-MAPKAP-K2 and PDK1, and repurified on Ni2+/NTA-agrose and glutathioneagarose (Upstate, UK; #14-276).

For the biochemical Akt1 (inactive) assay recombinant full-length human Akt1 a containing N-terminal His6 tag was cloned and expressed in baculovirus infected Sf21 insect cells. The enzyme is purified using Ni2+/NTA-agarose (Upstate, UK; #14-279).

For the biochemical Akt1 (inactive) assay, recombinant full-length human PDK1, containing N-terminal His6 tag was cloned and expressed in baculovirus infected Sf21 insect cells. The enzyme is purified using Ni2+/NTA-agarose.

For the biochemical PKA assay the catalytic subunit of PKA was expressed in *E. coli* as a His-tagged human recombinant protein and purified accordingly (PanVera, USA; #R3791).

Biochemical ΔPH Akt1 Assay:

In order to study the inhibition of Akt according to the invention, a flashplate-based assay has been developed.

The Akt1 assay is a biochemical assay using Akt1 devoid of its PH domain and co-expressed with PDK1 in insect cells. The GST-ΔPH-Akt1 assay is run in 96 well plates by incubating 100 ng/well GST-ΔPH-Akt1, 100 ng/well histone 2B (Roche, #223514) as substrate, 10 µl of compound of invention (test compounds were dissolved as 10 mM solutions in dimethylsulfoxide (DMSO) and subsequently diluted) and 100 nM ATP (including $^{33}$P-ATP) in 100 µl of reaction buffer (50 nM HEPES, pH7.5; 3 mM $MgCl_2$; 3 mM $MnCl_2$; 3 µM Na-Orthovanadat; 1 mM DTT; 1 µg/ml PEG8000) for 80 minutes at 30° C. The reactions are terminated by adding 100 µl stopping buffer (2% $H_3PO_4$ for 5 minutes) and are washed 3 times by using washing buffer (0.9% NaCl). Relying on the incorporation of $^{33}$P into the protein substrate histone 2B, the detection is based on the adhesion of the phosphorylated protein to the surface of scintillator-coated flash plates (NEN, USA; #SMP-200). This phosphorylation is measured by counting the plate for 60 sec. using a plate reader (Wallac Microbeta; Perkin Elmer, USA). The analysis of the data is performed using a biostatistical program (GraphPad Prism, USA). Preferred compounds show an $IC_{50}$ of ΔPH-Akt1 inhibition below 5 µM.

Representative $IC_{50}$ values for inhibition of deltaPHAkt1 determined in the aforementioned assay follow from the following table A, in which the numbers of the compounds correspond to the numbers of the examples.

TABLE A

| Akt inhibition: | |
| --- | --- |
| Compounds | $IC_{50}$ (µmol/l) |
| 2, 10, 45, 47, 49, 50, 52, 54 to 56, 58, 63 to 66, 68 to 70, 73, 75 and 76 | The inhibitory values of these listed Examples are ≦2 |
| 6, 9, 11, 12, 42, 46, 51, 57, 59, 61, 62, 67, 71, 72, 74, 77 and 78 | The inhibitory values of these listed Examples are ≦5 |

Biochemical Akt1 (Active) Assay (Full-Length Akt1):

In order to study the inhibition of Akt1 (full-length version) according to the invention, a flashplate-based assay has been developed.

The full-length Akt1 assay is a biochemical assay using Akt1 N-terminally fused to GST and co-expressed with PDK1 in insect cells. The Akt1 assay is run in 96 well plates by incubating 500 ng/well GST-Akt1, 1 µM Crosstide (N-terminally biotinylated synthetic peptide (KGSGSGRPRTSS-FAEG) Upstate, #12-385) as substrate, 10 µl of test compound (test compounds were dissolved as 10 mM solutions in dimethylsulfoxide (DMSO) and subsequently diluted) and 100 nM ATP (including $^{33}$P-ATP) in 100 µl of reaction buffer (50 mM HEPES, pH7.5; 3 mM $MgCl_2$; 3 mM $MnCl_2$; 3 µM Na-Orthovanadat; 1 mM DTT; 1 µg/ml PEG8000) for 60 minutes at 30° C. in 96 well microtiter plates. The reactions are terminated by adding 100 µl stopping buffer (5M NaCl, 35 mM EDTA pH 8,0) for 5 minutes. 190 µl of the reaction mixture are transferred into streptavidin-coated Flashplates (Perkin Elmer, #SMP-103) and incubated for further 30 minutes at room temperature. The plates are washed 3 times by using washing buffer (0.9% NaCl). Relying on the incorporation of $^{33}$P into the peptide substrate crosstide, the detection is based on the specific binding of the biotinylated peptide to the streptavidin-coated surface of scintillator-coated flash plates (NEN, USA; #SMP-103). This phosphorylation is measured by counting the plate for 60 sec. using a plate reader (Wallac Microbeta; Perkin Elmer, USA). The analysis of the data is performed using a biostatistical program (GraphPad Prism, USA). Preferred compounds show an $IC_{50}$ of Akt1 inhibition below 2 µM.

Representative $IC_{50}$ values for inhibition of Akt1 (full-length Akt1, active) determined in the aforementioned assay follow from the following table B, in which the numbers of the compounds correspond to the numbers of the examples.

TABLE B

| Akt1 inhibition (full-length Akt1, active): | |
| --- | --- |
| Compounds | $IC_{50}$ (µmol/l) |
| 49, 57, 68, 69 and 73 | The inhibitory values of these listed Examples are ≦1.75 |

Biochemical Akt1 (Inactive) Assay (Full-Length Akt1):

In order to study the inhibition of Akt1 activation of the compounds according to the invention, an IMAP-based assay has been developed for the protein kinase B alpha, PKBα (fullAkt1, inactive). PDK1-dependent activation and subsequent enzymatic activity of Akt1: Activity of purified human Akt1 is routinely measured in an assay in which the enzyme is first activated by PDK1 in the presence of phosphatidylinositol-3,4,5-triphosphate (PIP3). Once activated, Akt1-dependent phosphorylation of a fluorescence labelled peptide substrate is measured by fluorescence polarisation using the IMAP technology (Molecular Devices).

This Akt-activation-assay uses inactive full length AKT1 (Upstate, #25675U), full length PDK1, a fluorescence labelled AKT1 substrate peptide (Thermo Electron GmbH, 5-Fluorescein-NH-RARTSSFAEPG-CONH$_2$), and phospholipid vesicles (PIP3, Biomol, Cat.# PH-107; DOPC/DOPS "Upstate Lipid Blend", Avanti Polar Lipids, Cat.# 790595P).

The phospholipids are prepared as follows: 5 mg DOPC/DOPS are solved in 200 µl 10 mM Tris (pH 7.4) and 300 µg PIP3 are resuspended in 950 µl 10 mM Tris (pH 7.4) by pipetting. 950 µl solved PIP3 are mixed with 50 µl solved DOPC/DOPS and incubated for 2 h at a temperature below 20° C. Then the mixture is subjected to sonification for 30 min. at max. power until a translucent phopholipid vesicle preparation is obtained. Aliquots of the vesicle suspension are frozen at −80° C. until needed, likewise the solved DOPC/DOPS.

Assays are performed in 384-well plates. Incubations are carried out for 60 min. at room temperature. The reaction buffer mixture contains in a final volume of 25 µl: 10 mM Tris pH 7.4, 10 mM MgCl$_2$. 1 mM DTT, and 0,1 mg/ml BSA. In contrast the activation buffer contains: 50 ng/well Akt1, 20 ng/well PDK1, 1.25 µM peptide substrat, 50 µM ATP, and phospholipid vesicles (1:20). Test compounds are added from stock solutions in DMSO before activation of Akt1 by PDK1. After the incubation the beads (IMAP binding reagent; Molecular Devices; 1:167) are added and the fluorescence polarization is measured (excitation 485 nm, emission 530 nm). The analysis of the data is performed using a biostatistical program. Preferred compounds show an IC$_{50}$ of Akt1 inhibition below 5 µM.

Representative IC$_{50}$ values for inhibition of Akt1 (full-length Akt1, inactive) determined in the aforementioned assay follow from the following table C, in which the numbers of the compounds correspond to the numbers of the examples.

TABLE C

| Inhibition of Akt1 activation(full-length Akt1, inactive): | |
|---|---|
| Compounds | IC$_{50}$ (µmol/l) |
| 49, 57, 68 and 69 | The inhibitory values of these listed Examples are ≦4.4 |

Biochemical PKA Assay:

In order to study the kinase inhibition activity of the compounds according to the invention, a flashplate-based assay has been developed for the serine/threonine kinase, PKA.

The assay is run in 96 well plates by incubating 1 ng/well His-PKA (PanVera, USA; #R3791), 0.5 µM/well PKA peptide (#12-394; Upstate, USA) as substrate, 10 µl of compound of invention (test compounds were dissolved as 10 mM solutions in dimethylsulfoxide (DMSO) and subsequently diluted) and 100 nM ATP (including $^{33}$P-ATP) in 100 µl of reaction buffer (50 mM HEPES, pH7.5; 3 mM MgCl$_2$; 3 mM MnCl$_2$; 3 µM Na-Orthovanadat; 1 mM DTT) for 80 minutes at 22° C. The reactions are stopped by adding 100 µl stopping buffer (2% H$_3$PO$_4$ for 5 minutes) and are washed 3 times by using washing buffer (200 µl 1xPBS). Relying on the incorporation of $^{33}$P into the peptide substrate, the detection is based on the adhesion of the phosphorylated peptide to the surface of scintillator-coated Flash plates (Perkin Elmer, USA; #SMP-103). This phosphorylation is measured by counting the plate for 60 sec. using a plate reader (Wallac Microbeta; Perkin Elmer, USA). By using this method the IC$_{50}$ of the PKA inhibition is determined. The analysis of the data is performed using a biostatistical program (GraphPad Prism, USA). Preferred compounds show an IC$_{50}$ of PKA inhibition above 10 µM.

Representative IC$_{50}$ values for PKA inhibition determined in the aforementioned assay follow from the following table D, in which the numbers of the compounds correspond to the numbers of the examples.

TABLE D

| PKA inhibition: | |
|---|---|
| Compounds | IC$_{50}$ (µmol/l) |
| 45, 47, 64 to 66, 68 to 73, 75 and 76 | These listed Examples do not substantially inhibit PKA |

Cellular PI3K/Akt Pathway Assay

In order to study the cellular activity of the compounds according to the invention, an ELISA-based assay has been established. The assay is based on a Sandwich ELISA kit (PathScan™ Phospho-Akt1 (Ser473); Cell Signaling, USA; #7160).

The assay detects endogenous levels of phosphorylated Akt1 protein. A phospho-Akt (Ser473) antibody (Cell Signaling, USA; #9271) has been coated onto the microwells. After incubation with cell lysates, the phosphorylated Akt protein is captured by the coated antibody. Following extensive washing, Akt1 monoclonal antibody (Cell Signaling, USA; #2967) is added to detect the captured phospho-Akt1 protein. HRP-linked anti-mouse antibody (Cell Signaling, USA; #7076) is then used to recognize the bound detection antibody. HRP substrate (=TMB; Cell Signaling, USA; #7160) is added to develop colour. The magnitude of optical density for this developed color is proportional to the quantity of phosphorylated Akt1 protein.

MCF7 cells (ATCC HTB-22) are seeded into 96 well fate bottom plates at a density of 10000 cells/well. 24 hours after seeding the cells are starved using estrogen-free medium (IMEM including 0.1% charcoal treated FCS). After 24 hours 1 µl each of the compound dilutions (test compounds were dissolved as 10 mM solutions in DMSO and subsequently diluted) are added into each well of the 96 well plates and incubated for 48 h at 37° C. in a humidified atmosphere containing 5% CO$_2$. To stimulate Akt phosphorylation, β-Heregulin (20 ng/ml) is added in parallel to the compounds. Wells containing unstimulated control cells (no β-Heregulin stimulation) are incubated with or without the diluted compound. Wells containing untreated control cells (no compound) are filled with medium containing 0.5% v:v DMSO and are with β-Heregulin or are not stimulated.

Cells are harvested under nondenaturing conditions and lysed with brief sonification in 1× cell lyses buffer (20 mM Tris (pH7.5), 150 mM NaCl, 1 mM ethylene diaminetetraacetate (EDTA), 1 mM ethylene glycolbis-(2-aminoethyl)-N,N,N',N'-tetraacetic acid (EGTA), 1% Triton X-100, 2.5 mM sodium pyrophosphate, 1 mM β-glycerolphosphate, 1 mM Na3VO4, 1 µg/ml leupeptin). The lysate is microcentrifuged for 10 minutes at 4° C. and the supernatant is transferred to a new tube. 100 µl of sample diluent (0.1% tween-20, 0.1% sodium azide in 20×PBS) are added to a microcentrifuge tube and 100 µl of cell lysate are transferred into the tube and vortexed. 100 µl of each diluted cell lysate are added to the appropriate well (phospho-Akt (Ser473) antibody coated microwells; Cell Signaling, USA; #7160) and incubated overnight at 4° C. The plates are washed 4 times with 1× wash buffer (1% tween-20, 0.33% thymol, in 20×PBS). Then 100 µl of detection antibody (Akt1 (2H10) monoclonal detection antibody; Cell Signaling, USA; #2967) are added to each well and incubated for 1 h at 37° C. The washing procedure is repeated between each step. 100 µl of HRP-linked secondary antibody (anti-mouse IgG HRP-linked antibody; Cell Signaling, USA; #7076) are added to each well and incubated for 30 minutes at 37° C. Than 100 µl of TMB substrate (0.05% 3,3',5,5' tetramethylbenzidine, 0.1% hydrogen peroxide, complex polypeptides in a buffered solution; Cell Signaling, USA; #7160) are added to each well and incubated for 30 minutes at 25° C. Finally 100 µl of STOP solution (0.05% α and β unsaturated carbonyl compound) are added to each well and the plate are shaked gently for a few seconds. The absorbance is read at 450 nm (Wallac Victor2; Perkin Elmer, USA) within 30 minutes after adding STOP solution. The analysis of the data is performed using a statistical program (Excel; Microsoft, USA).

Representative $IC_{50}$ values for Akt pathway inhibition determined in the aforementioned assay follow from the following table E, in which the number of the compound corresponds to the number of the example.

TABLE E

| Akt pathway inhibition (pAkt-ELISA): | |
| --- | --- |
| Compounds | $IC_{50}$ (µmol/l) |
| 69 | 6 |

Cellular pGSK3 Assay:

In order to study the cellular activity of the compounds according to the invention, an ELISA-based assay has been established for the phosphorylated glycogen synthetase kinase 3, GSK3. The assay is based on a solid phase sandwich ELISA that detects endogenous levels of the phosphorylated GSK3 (BioSource International, Inc.; Catalog #KHO0461). A phospho-GSK3 (Ser9) antibody has been coated onto the microwells. After incubation with cell lysates, the coated antibody captures the phosphorylated GSK3 protein. Following extensive washing, GSK3 polyclonal antibody is added to detect the captured phospho-GSK3 protein. HRP-linked anti-mouse antibody (anti-rabbit IgG-HRP) is then used to recognize the bound detection antibody. After the second incubation and washing to remove all the excess anti-rabbit IgG-HRP, a substrate solution is added, which is acted upon by the bound enzyme to produce color. The intensity of this colored product is directly proportional to the concentration of GSK-3β [pS9] present in the original specimen.

MCF7 cells (ATCC HTB-22) are seeded into 96 well plates at a density of 10000 cells/well. After 24 hours 1 µl each of the compound dilutions (test compounds were dissolved as 10 mM solutions in DMSO and subsequently diluted) are added into each well of the 96 well plates and incubated for 48 h at 37° C. in a humidified atmosphere containing 5% $CO_2$.

Cells are harvested and lysed with brief vortexing in cell extraction buffer (10 mM Tris, pH 7.4, 100 mM NaCl, 1 mM EDTA, 1 mM EGTA, 1 mM NaF, 20 mM Na4P2O7, 2 mM Na3VO4, 1% Triton X-100, 10% glycerol, 0.1% SDS, 0.5% deoxycholate, 1 mM PMSF). The lysate are centrifuged for 10 minutes at 4° C. and the supernatant transferred to a new tube. 50 µl of sample diluent (standard diluent buffer, Biosource) are added and 100 µl of cell lysate transferred into the tube and vortexed. 100 µl of each diluted cell lysate are added to the appropriate well (phospho-GSK3 (Ser9) antibody coated microwells; BioSource) and incubated for 3 h at room temperature. The plates are washed 4 times with Ix wash buffer (Biosource). 50 µl of detection antibody (GSK3 (Ser9) detection antibody; BioSource) are added to each well and incubated for 30 min. at room temperature. The washing procedure is repeated between each step. 100 µl of HRP-linked secondary antibody (anti-mouse IgG HRP-linked antibody) are added to each well and incubated for 30 minutes at room temperature. 100 µl of TMB substrate (0.05% 3,3',5,5' tetramethylbenzidine, 0.1% hydrogen peroxide, complex polypeptides in a buffered solution; Biosource) are added to each well and incubated for 30 minutes at room temperature. Finally 100 µl of Stop solution (0.05% α and β unsaturated carbonyl compound) are added to each well and the plate are shaked gently for a few seconds. The absorbance is measured at 450 nm (Wallac Victor2; Perkin Elmer, USA) within 30 minutes after adding Stop solution. The analysis of the data is performed using a statistical program (Microsoft Excel, USA) and the inhibition of pGSK3 phosphorylation is determined.

Representative $IC_{50}$ values for GSK3 inhibition determined in the aforementioned assay follow from the following table F, in which the number of the compound corresponds to the number of the example.

TABLE F

| GSK3 inhibition (pGSK3-ELISA): | |
| --- | --- |
| Compounds | $IC_{50}$ (µmol/l) |
| 69 | 10 |

Cellular Proliferation/Cytotoxicity Assay:

The anti-proliferative activity of the compounds as described herein, is evaluated using MCF7 and MDA-MB-468 (ATCC HTB-22 and HTB-132) cell lines and the Alamar Blue (Resazurin) cell viability assay (O'Brien et al. Eur J Biochem 267, 5421-5426, 2000). Resazurin is reduced to the fluorescent rescrufin by cellular dehydrogenase activity, correlating with viable, proliferating cells. Test compounds are dissolved as 10 mM solutions in DMSO and subsequently diluted. MCF7 or MDA-MB-434 cells were seeded into 96 well flat bottom plates at a density of 10000 cells/well (MCF7) or 5000 cells/well (MDA-MB-468) in a volume of 200 µl/well. 24 hours after seeding, 1 µl each of the compound dilutions are added into each well of the 96 well plates. Each compound dilution is tested as at least as duplicates. Wells containing untreated control cells were filled with 200 µl DMEM containing 0.5% v:v DMSO. The cells are then incubated with the substances for 48 hours at 37° C. in a humidified atmosphere containing 5% carbon dioxide. To determine cell viability, 20 µl of a Resazurin solution (Sigma; 90 mg/l) are added. After 4 hours incubation at 37° C. the fluorescence is measured at an extinction of 544 nm and an emission of 590 nm (Wallac Victor2; Perkin Elmer, USA). For the calculation of the cell viability the emission value from untreated cells is set as 100% viability and the emission rates of treated cells are set in relation to the values of untreated cells. Viabilities are expressed as % values. The corresponding $IC_{50}$ values of the compounds for cytotoxic activity are determined from the concentration-effect curves by means of non-linear regression. The analysis of the data is performed using a biostatistical program (GraphPad Prism, USA).

Representative $IC_{50}$ values for anti-proliferative/cytotoxic potency determined in the aforementioned assay follow from the following table G, in which the numbers of the compounds correspond to the numbers of the examples.

TABLE G

| Anti-proliferative/cytotoxic activity: | | |
|---|---|---|
| Compounds | $IC_{50}$ MCF7 (µmol/l) | $IC_{50}$ MDA468 (µmol/l) |
| 45, 47, 49, 52, 54, 63, 68, 69 and 78 | The inhibitory values of these listed Examples are ≦16.60 | The inhibitory values of these listed Examples are ≦6.05 |

The compounds of formula I which are mentioned in one or more of the tables A to G as well as their salts are a preferred subject in the present invention.

Chemosensitization Assay

The herein disclosed compounds are evaluated for the ability to sensitize cancer cells towards apoptotic stimuli. Compounds described in this invention are tested alone and in combination with chemotherapeutic and targeted cancer therapeutics to determine the effect on apoptosis induction. Cancer cells are seeded in 96 well plates at concentrations ranging from $2 \times 10^3$ to $1 \times 10^4$ cells per well in their respective growth media. 48-72 hours later, the apoptosis assay are set up as follows:

a) For combination assays with a chemotherapeutic agent like camptothecin, compounds are added at respective concentrations indicated and plates incubated at 37° C. in a $CO_2$ incubator for 18 hours. For standard combination assays uitilizing treatment with camptothecin are added at the same time at the respective concentrations indicated.

b) For combinations assays involving addition of pro-apoptotic agents like the death receptor ligand TRAIL/Apo2 L (Research Diagnostics) compounds are added for 1.5 hours prior to addition of TRAIL and plates incubated an additional 3 to 4 hours post TRAIL addition. In the case of the time course, plates are incubated for 2, 3, 4 and 6 hours with TRAIL ligand before ending the assay.

For both procedures, total final volumes do not exceed 250 µl. At the end of the incubation time, the cells are pelleted by centrifugation (200×g; 10 min. at RT) and the supernatant is discarded. The cells are resuspended and incubated using lysis buffer for 30 min. at RT (Cell Death Detection ELISA$^{PLUS}$, Roche, Cat. No. 11 774 425 001). After the centrifugation is repeated (200×g; 10 min. at RT) an aliquot of the supernatant are transferred to a streptavidin-coated well of a microplate. Followed by the incubation (2 h, RT) and binding of nucleosomes in the supernatant with two monoclonal antibodies, anti-histone (biotin-labeled) and anti-DNA (peroxidase-conjugated; Cell Death Detection ELISA$^{PLUS}$, Roche, Cat. No. 11 774 425 001). The antibody-nucleosome complexes are bound to the microplate. The immobilized antibody-histone complexes are washed three times at RT to remove cell components that are not immunoreactive. The substrate solution (ABTS; Cell Death Detection ELISA$^{PLUS}$, Roche, Cat. No. 11 774 425 001) are added and the samples were incubated for 15 min., RT. The amount of coloured product (and thus, of immobilized antibodyhistone complexes) is determined spectrophotometrically (absorbance at 405 nm). Data are expressed as percent activity of control with cisplatin used as a positive control. Apoptosis induction by 50 µM cisplatin is arbitrarily defined as 100 cisplatin units (100 CPU).

The invention claimed is:

1. A compound of formula Ia (Ia)

in which
R1 is dibenzofuran-4-yl,
R2 is hydrogen,
R3 is —U—Ar2, or —V—Har2, in which
U is a bond,
Ar2 is 3-(R31)-phenyl, 4-(R31)-phenyl, or 2-fluoro-4-(R31)-phenyl, in which
R31 is amidino, or —W—R311, in which
W is methylene, ethylene, or 1,1-dimethyl-methylene,
R311 is —N(R312)R313, in which
R312 is hydrogen, or methyl,
R313 is hydrogen,
V is a bond,
Har2 is 1,2,3,4-tetrahydroisoquinolin-7-yl, 1,2,3,4-tetrahydroisoquinolin-6-yl, or R33-substituted pyridyl, in which
R33 is aminomethyl,
or a salt thereof.

2. A compound according to claim 1, which is from formula Ia in which
R1 is dibenzofuran-4-yl,
R2 is hydrogen,
R3 is —U—Ar2, in which
U is a bond,
Ar2 is 3-(R31)-phenyl, or 4-(R31)-phenyl, in which
R31 is amidino, or —W—R311, in which
W is methylene,
R311 is —N(R312)R313, in which
R312 is hydrogen,
R313 is hydrogen,
or a salt thereof.

3. A compound according to claim 1, which is from formula Ia in which
R1 is dibenzofuran-4-yl,
R2 is hydrogen,
R3 is —V—Har2, in which
V is a bond,
Har2 is 1,2,3,4-tetrahydroisoquinolin-7-yl, or 1,2,3,4-tetrahydroisoquinolin-6-yl, 6-(R33)-pyrid-3-yl, 6-(R33)-pyrid-2-yl, 2-(R33)-pyrid-4-yl, 4-(R33)-pyrid-2-yl, or 5-(R33)-pyrid-2-yl, in which
R33 is aminomethyl;
or a salt thereof.

4. A compound according to claim 1 selected from the group consisting of
N-[4-(6-Dibenzofuran-4-yl-pyrimidin-4-ylamino)-phenyl]-4-morpholin-4-yl-benzamide, N-[4-(6-Dibenzofuran-4-yl-pyrimidin-4-ylamino)-phenyl]-4-dimethylamino-benzamide,
N-[4-(6-Dibenzofuran-4-yl-pyrimidin-4-ylamino)-phenyl]-4-(4-methyl-piperazin-1-ylmethyl)-benzamide,
N-[4-(6-Dibenzofuran-4-yl-pyrimidin-4-ylamino)-phenyl]-2-(4-dimethyl-amino-phenyl)-acetamide,
N-[4-(6-Dibenzofuran-4-yl-pyrimidin-4-ylamino)-phenyl]-2-dimethylamino-benzamide,
N-[4-(6-Dibenzofuran-4-yl-pyrimidin-4-ylamino)-phenyl]-3-pyrrolidin-1-ylbenzamide,
N-[4-(6-Dibenzofuran-4-yl-pyrimidin-4-ylamino)-phenyl]-benzamide,
4-tert-Butyl-N-[4-(6-dibenzofuran-4-yl-pyrimidin-4-ylamino)-phenyl]-benzamide,
3,4-Dichloro-N-[4-(6-dibenzofuran-4-yl-pyrimidin-4-ylamino)-phenyl]-benzamide,
N-[4-(6-Dibenzofuran-4-yl-pyrimidin-4-ylamino)-phenyl]-3-dimethylamino-benzamide,
N-[4-(6-Dibenzofuran-4-yl-pyrimidin-4-ylamino)-phenyl]-isonicotinamide,
N-[4-(6-Dibenzofuran-4-yl-pyrimidin-4-ylamino)-phenyl]-4-dimethylaminomethyl-benzamide,
N-[4-(6-Dibenzofuran-4-yl-pyrimidin-4-ylamino)-phenyl]-4-morpholin-4-ylmethyl-benzamide,
N-[4-(6-Dibenzofuran-4-yl-pyrimidin-4-ylamino)-phenyl]-4-(4-methylpiperazin-1-yl)-benzamide,
N-[4-(6-Dibenzofuran-4-yl-pyrimidin-4-ylamino)-phenyl]-6-morpholin-4-yl-nicotinamide,
N-[4-(6-Dibenzofuran-4-yl-pyrimidin-4-ylamino)-phenyl]-3-[3-methoxy-1-(2-methoxyethyl)-propyl]-benzamide,
tert-Butyl N-{4-[4-(6-dibenzofuran-4-yl-pyrimidin-4-ylamino)-phenylcarbamoyl]-benzyl}-carbamate,
tert-Butyl N-{2-[4-(6-Dibenzofuran-4-yl-pyrimidin-4-ylamino)-phenylcarbamoyl]-phenyl}-carbamate,
tert-Butyl N-{3-[4-(6-Dibenzofuran-4-yl-pyrimidin-4-ylamino)-phenylcarbamoyl]-phenyl}-carbamate,
tert-Butyl 3-{4-[4-(6-Dibenzofuran-4-yl-pyrimidin-4-ylamino)-phenylcarbamoyl]-phenyl}-piperidin-1-carboxylate,
tert-Butyl N-(4-{[4-(6-dibenzofuran-4-yl-pyrimidin-4-ylamino)-phenylcarbamoyl]-methyl}-phenyl)-carbamate,
tert-Butyl N-{3-[4-(6-Dibenzofuran-4-yl-pyrimidin-4-ylamino)-phenylcarbamoyl]-benzyl}-carbamate,
tert-Butyl N-(2-{4-[4-(6-Dibenzofurane-4-yl-pyrimidin-4-ylamino)-phenylcarbamoyl]phenyl}-ethyl)-carbamate,
tert-Butyl N-{2-[4-(6-Dibenzofuran-4-yl-pyrimidin-4-ylamino)-phenylcarbamoyl]-pyridin-4-ylmethyl}-carbamate,
tert-Butyl N-{4-[4-(6-dibenzofuran-4-yl-pyrimidin-4-ylamino)-phenylcarbamoyl]-benzyl}-methyl-carbamate,
tert-Butyl {5-[4-(6-dibenzofuran-4-yl-pyrimidin-4-ylamino)-phenylcarbamoyl]-pyridin-2-ylmethyl}-carbamate,
tert-Butyl {4-[4-(6-dibenzofuran-4-yl-pyrimidin-4-ylamino)-phenylcarbamoyl]-pyridin-2-ylmethyl}-carbamate,
tert-Butyl (4-{[4-(6-dibenzofuran-4-yl-pyrimidin-4-ylamino)-phenylcarbamoyl]-methyl}-benzyl)-carbamate,
tert-Butyl N-(1-{4-[4-(6-dibenzofuran-4-yl-pyrimidin-4-ylamino)-phenylcarbamoyl]-phenyl}-1-methyl-ethyl)-carbamate,
tert-Butyl N-(2-{3-[4-(6-dibenzofuran-4-yl-pyrimidin-4-ylamino)-phenylcarbamoyl]-phenyl}-ethyl)-carbamate,
tert-Butyl {4-[4-(6-dibenzofuran-4-yl-pyrimidin-4-ylamino)-phenylcarbamoyl]-phenyl}-(2-methoxy-ethyl)-carbamate,
tert-Butyl N-{4-[4-(6-dibenzofuran-4-yl-pyrimidin-4-ylamino)-phenylcarbamoyl]-3-fluorobenzyl}carbamate,
tert-Butyl {6-[4-(6-dibenzofuran-4-yl-pyrimidin-4-ylamino)-phenylcarbamoyl-pyridin-2-ylmethyl}-carbamate,
tert-Butyl N-{5-[4-(6-dibenzofuran-4-yl-pyrimidin-4-ylamino)-phenylcarbamoyl]-pyridin-3-ylmethyl}-carbamate,
3-Cyano-N-[4-(6-dibenzofuran-4-yl-pyrimidin-4-ylamino)-phenyl]-benzamide,
3-Carbamimidoyl-N-[4-(6-dibenzofuran-4-yl-pyrimidin-4-ylamino)-phenyl]-benzamide,
4-Cyano-N-[4-(6-dibenzofuran-4-yl-pyrimidin-4-ylamino)-phenyl]-benzamide,
4-Carbamimidoyl-N-[4-(6-dibenzofuran-4-yl-pyrimidin-4-ylamino)-phenyl]-benzamide,
4-Aminomethyl-N-[4-(6-dibenzofuran-4-yl-pyrimidin-4-ylamino)-phenyl]-benzamide,
2-Amino-N-[4-(6-dibenzofuran-4-yl-pyrimidin-4-ylamino)-phenyl]-benzamide,
3-Amino-N-[4-(6-Dibenzofuran-4-yl-pyrimidin-4-ylamino)-phenyl]-benzamide,
N-[4-(6-Dibenzofuran-4-yl-pyrimidin-4-ylamino)-phenyl]-4-piperidin-3-yl-benzamide,
2-(4-Amino-phenyl)-N-[4-(6-dibenzofuran-4-yl-pyrimidin-4-ylamino)-phenyl]-acetamide,
3-Aminomethyl-N-[4-(6-dibenzofuran-4-yl-pyrimidin-4-ylamino)-phenyl]-benzamide,
4-(2-Amino-ethyl)-N-[4-(6-dibenzofuran-4-yl-pyrimidin-4-ylamino)-phenyl]-benzamide,
4-Aminomethyl-pyridin-2-carbonsäure-[4-(6-dibenzofuran-4-yl-pyrimidin-4-ylamino)-phenyl]-amide,
N-[4-(6-Dibenzofuran-4-yl-pyrimidin-4-ylamino)-phenyl]-4-methylaminomethyl-benzamide,
6-Aminomethyl-N-[4-(6-dibenzofuran-4-yl-pyrimidin-4-ylamino)-phenyl]-nicotinamide,
2-Aminomethyl-N-[4-(6-dibenzofuran-4-yl-pyrimidin-4-ylamino)-phenyl]-isonicotinamide,
2-(4-Aminomethyl-phenyl)-N-[4-(6-dibenzofuran-4-yl-pyrimidin-4-ylamino)-phenyl]-acetamide,
1,2,3,4-Tetrahydro-isochinolin-7-carbonsäure-[4-(6-dibenzofuran-4-yl-pyrimidin-4-ylamino)-phenyl]-amide,
4-(1-Amino-1-methyl-ethyl)-N-[4-(6-dibenzofuran-4-yl-pyrimidin-4-ylamino)-phenyl]-benzamide,
3-(2-Amino-ethyl)-N-[4-(6-dibenzofuran-4-yl-pyrimidin-4-ylamino)-phenyl]-benzamide,
N-[4-(6-Dibenzofuran-4-yl-pyrimidin-4-ylamino)-phenyl]-4-(2-methoxyethylamino)benzamide,
4-Aminomethyl-N-[4-(6-dibenzofuran-4-yl-pyrimidin-4-ylamino)-phenyl]-2-fluorobenzamide,
6-Aminomethyl-pyridin-2-carbonsäure-[4-(6-dibenzofuran-4-yl-pyrimidin-4-ylamino)-phenyl]-amide,
5-Aminomethyl-N-[4-(6-dibenzofuran-4-yl-pyrimidin-4-ylamino)-phenyl]-nicotinamide,
3-Amino-N-[4-(6-dibenzofuran-4-yl-pyrimidin-4-ylamino)-phenyl]-2-(3,4-dichloro-phenyl)-propionamide,
5-Aminomethyl-pyridine-2-carboxylic acid [4-(6-dibenzofuran-4-yl-pyrimidin-4-ylamino)-phenyl]-amide, 1,2,3,4-Tetrahydro-isoquinoline-6-carboxylic acid [4-(6-dibenzofuran-4-yl-pyrimidin-4-ylamino)-phenyl]-amide;

and the salts of these compounds.

5. A compound according to claim 1 selected from the group consisting of tert-Butyl {4-[3-(6-dibenzofuran-4-yl-pyrimidin-4-ylamino)-phenylcarbamoyl]-benzyl}-carbamate, tert-Butyl N-(2-{4-[3-(6-dibenzofuran-4-yl-pyrimidin-4-ylamino)-phenylcarbamoyl]-phenyl}-ethyl)-carbamate, tert-Butyl N-{2-[3-(6-dibenzofuran-4-yl-pyrimidin-4-ylamino)-phenylcarbamoyl]-phenyl}-carbamate, tert-Butyl {3-[3-(6-dibenzofuran-4-yl-pyrimidin-4-ylamino)-phenylcarbamoyl]-phenyl}-carbamate, tert-Butyl N-{3-[3-(6-Dibenzofuran-4-yl-pyrimidin-4-ylamino)-phenylcarbamoyl]-benzyl}-carbamate, tert-Butyl N-{4-[3-(6-Dibenzofuran-4-yl-pyrimidin-4-ylamino)-phenylcarbamoyl]-phenyl}-carbamate, tert-Butyl N-{4-[3-(6-dibenzofuran-4-yl-pyrimidin-4-ylamino)-4-methyl-phenylcarbamoyl]-benzyl}-carbamate, N-[3-(6-Dibenzofuran-4-yl-pyrimidin-4-ylamino)-phenyl]-4-dimethylamino-benzamide, N-[3-(6-Dibenzofuran-4-yl-pyrimidin-4-ylamino)-phenyl]-4-dimethylaminomethyl-benzamide, N-[3-(6-Dibenzofuran-4-yl-pyrimidin-4-ylamino)-phenyl]-3-dimethylamino-benzamide, 4-Aminomethyl-N-[3-(6-dibenzofuran-4-yl-pyrimidin-4-ylamino)-phenyl]-benzamid, 4-(2-Amino-ethyl)-N-[3-(6-dibenzofuran-4-yl-pyrimidin-4-ylamino)-phenyl]-benzamide, 2-Amino-N-[3-(6-dibenzofuran-4-yl-pyrimidin-4-ylamino)-phenyl]-benzamide, 3-Amino-N-[3-(6-dibenzofuran-4-yl-pyrimidin-4-ylamino)-phenyl]-benzamide, 3-Aminomethyl-N-[3-(6-dibenzofuran-4-yl-pyrimidin-4-ylamino)-phenyl]-benzamide, 4-Amino-N-[3-(6-dibenzofuran-4-yl-pyrimidin-4-ylamino)-phenyl]-benzamide, 4-Aminomethyl-N-[3-(6-dibenzofuran-4-yl-pyrimidin-4-ylamino)-4-methyl-phenyl]-benzamide, 3-Amino-N-[3-(6-dibenzofuran-4-yl-pyrimidin-4-ylamino)-phenyl]-2-(3,4-dichlorophenyl)-propionamide;

and the salts of these compounds.

6. A pharmaceutical composition comprising one or more compounds according to claim 1 or a pharmaceutically acceptable salt thereof, together with one or more pharmaceutical excipients and/or vehicles.

7. A combination comprising one or more first active ingredient selected from a compound according to claim 1 or a pharmaceutically acceptable salt thereof, and one or more second active ingredient selected from the group consisting of chemotherapeutic anti-cancer agents and target-specific anti-cancer agents, for separate, sequential, simultaneous or chronologically staggered use in therapy to treat or ameliorate a hyperproliferative disease of benign or malignant behaviour and/or a disorder responsive to the induction of apoptosis in a mammal.

8. A method of treating breast cancer in a patient comprising administering to said patient a therapeutically effective amount of a compound according to claim 1 or a pharmaceutically acceptable salt thereof.

* * * * *